(12) United States Patent
Havranek

(10) Patent No.: US 12,414,962 B2
(45) Date of Patent: Sep. 16, 2025

(54) **METHOD FOR TREATING *C. acnes* BACTERIA-ASSOCIATED DISEASES**

(71) Applicant: ELIGO BIOSCIENCE, Paris (FR)

(72) Inventor: Jan Havranek, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

(21) Appl. No.: 18/782,965

(22) Filed: Jul. 24, 2024

(65) Prior Publication Data

US 2025/0032528 A1 Jan. 30, 2025

Related U.S. Application Data

(60) Provisional application No. 63/515,223, filed on Jul. 24, 2023.

(51) Int. Cl.
*A61K 31/7088* (2006.01)
*A61P 17/10* (2006.01)
*A61P 31/04* (2006.01)

(52) U.S. Cl.
CPC .......... *A61K 31/7088* (2013.01); *A61P 17/10* (2018.01); *A61P 31/04* (2018.01)

(58) Field of Classification Search
CPC ....... A61K 31/7088; A61P 17/10; A61P 31/04
See application file for complete search history.

(56) References Cited

U.S. PATENT DOCUMENTS

| 10,113,163 B2 | 10/2018 | Liu et al. |
| 2015/0166980 A1 | 6/2015 | Liu et al. |

FOREIGN PATENT DOCUMENTS

| WO | 2017/136738 A2 | 8/2017 |
| WO | 2017/141173 A2 | 8/2017 |
| WO | 2018/236548 A1 | 12/2018 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |

OTHER PUBLICATIONS

Abudayyeh et al. RNA targeting with CRISPR-Cas13a, Nature, 2017, 550(7675), 280-284.
Anzalone et al. Search-and-replace genome editing without double-strand breaks or donor DNA, Nature, 2019, 576 (7785), 149-157.
Barnard et al. The balance of metagenomic elements shapes the skin microbiome in acne and health. Scientific Reports, 2016, 6(39491), 1-12.
Barnard et al. Porphyrin Production and Regulation in Cutaneous Propionibacteria, mSphere, 2020, 5(1), e00793-19, 1-10.
Bhate and Williams et al. Epidemiology of acne vulgaris, British Journal of Dermatology, 2013, 168, 474-485.
Briers et al. A standardized approach for accurate quantification of murein hydrolase activity in high-throughput assays, J. Biochem. Biophys. Methods, 2007, 70, 531-533.
Bruggemann et alA Janus-Faced Bacterium: Host-Beneficial and-Detrimental Roles of Cutibacterium acnes, Frontiers in Microbiology, 2021, 12(673845), 1-22.
Chen et al. fastp: an ultra-fast all-in-one FASTQ preprocessor. Bioinformatics, 34, 2018, i884-i890.
Chen et al. Precise and programmable C:G to G:C base editing in genomic DNA. bioRxiv, 2020, 213827, 1-19.
Chen et al. Programmable C:G to G:C genome editing with CRISPR-Cas9-directed base excision repair proteins. Nature Communications, 2021, 12:1384, 1-7.
Chernomor et al., Terrace Aware Data Structure for Phylogenomic Inference from Supermatrices, Syst. Biol. 2016, 65(6), 997-1008.
Choby and Skaar. Heme Synthesis and Acquisition in Bacterial Pathogens, J Mol Biol. 2016, 428(17), 3408-3428.
Ding et al. panX: pan-genome analysis and exploration. Nucleic Acids Research, 2018, 46(1), 1-12.
Donovan et al. Lysis of staphylococcalmastitis pathogens by bacteriophage phi11endolysin, FEMS Microbiol Lett, 2006, 265, 133-139.
Edgar. Muscle: multiple sequence alignment with high accuracy and high throughput. Nucleic Acids Research, 2004, 32(5), 1792-1797.
Farzadfard et Lu. Genomically Encoded Analog Memory with Precise In vivo DNA Writing in Living Cell Populations. Science. 2014, 346(6211), 1256272, 1-18.
Fitz-Gibbon et al. Propionibacterium acnes Strain Populations in the Human Skin Microbiome Associated with Acne. Journal of Investigative Dermatology, 2013, 133, 2152-2160.
Fonfara et al. Phylogeny of Cas9 determines functional exchangeability of dual-RNA and Cas9 among orthologous type II CRISPR-Cas systems. Nucleic Acids Research, 2014, 42(4), 2577-2590.
Gaudelli et al. Programmable base editing of A•T to G•C in genomic DNA without DNA cleavage, Nature, 2017, 551 (7681), 464-471.
Grunewald et al. A dual-deaminase CRISPR base editor enables concurrent adenine and cytosine editing, Nat Biotechnol, 2020, 38(7), 861-864.
Huang et al. Circulating Antibodies to Skin Bacteria Detected by Serological Lateral Flow Immunoassays Differentially Correlated With Bacterial Abundance, Frontiers in Microbiology, 2021, 12, 709562, 1-10.
Jinek et al. A programmable dual RNA-guided DNA endonuclease in adaptive bacterial immunity. Science, 2012, 337 (6096), 816-821.
Johnson and Cummins. Cell Wall Composition and Deoxyribonucleic Acid Similarities Among the Anaerobic Coryneforms, Classical Propionibacteria, and Strains of Arachnia propionica, Journal of Bacteriology, 1972, 109(3), 1047-1066.

(Continued)

*Primary Examiner* — J. E. Angell
(74) *Attorney, Agent, or Firm* — Arrigo, Lee, Guttman & Mouta-Bellum LLP

(57) ABSTRACT

The present invention concerns a method for treating or preventing a *Cutibacterium acnes* bacteria-associated disease in a subject, said method comprising modulating, in particular reducing, in said subject, the ratio of the amount of *C. acnes* bacteria of a newly identified category called α-type to the amount of *C. acnes* bacteria of newly identified category called β-type, the α-type category efficiently defining acne-associated strains and the β-type defining non acne-associated strains.

19 Claims, 8 Drawing Sheets

Specification includes a Sequence Listing.

(56) References Cited

OTHER PUBLICATIONS

Johnson et al. Strain-Level Differences in Porphyrin Production and Regulation in Propionibacterium acnes Elucidate Disease Associations, mSphere, 2016, 1(1), e00023-15, 1-12.

Karberg et al. Group II introns as controllable gene targeting vectors for genetic manipulation of bacteria, Nature Biotechnology, 2001, 19, 1162-1167.

Kelhala et al. Isotretinoin and lymecycline treatments modify the skin microbiota in acne, Exp Dermatol., 2018, 27 (1), 30-36.

Kolar et al. Propionibacterium acnes-induced immunopathology correlates with health and disease association, JCI Insight. 2019;4(5):e124687, 1-12.

Komor et al. Programmable editing of a target base in genomic DNA without double-stranded DNA cleavage. Nature. 533(7603), 420-424.

Koonin et al. Diversity, classification and evolution of CRISPR-Cas systems. Current Opinion in Microbiology, 2017, 37, 67-78.

Kosiol and Goldman. Different Versions of the Dayhoff Rate Matrix, Molecular Biology and Evolution, 2005, 22(2), 193-199.

Kurt et al. CRISPR C-to-G base editors for inducing targeted DNA transversions in human cells, Nat Biotechnol., 39 (1), 41-46.

Laclaverie et al. Development and characterization of a 3D in vitro model mimicking acneic skin. Exp Dermatol, 2020, 30, 347-357.

Langmead and Salzberg. Fast gapped-read alignment with Bowtie 2, Nature methods 2012, 9(4), 357-360.

Lessin and Leyden, Cutibacterium acnes (formerly Propionibacterium acnes) In-Vivo Reduction Assay: A Pre-Clinical Pharmacodynamic Assay for Evaluating Antimicrobial/ Antibiotic Agents in Development for Acne Treatment Skin Microbiome Handbook: From Basic Research to Product Development, 2020, 289-302.

Li. Aligning sequence reads, clone sequences and assembly contigs with BWA-MEM. arXiv, Quantitative Biology—Genomics, 2013, 1-3.

Li et al. Targeted, random mutagenesis of plant genes with dual cytosine and adenine base editors, Nature Biotechnology, 2020, 38, 875-882.

Lomholt and Kilian. Population Genetic Analysis of Propionibacterium acnes Identifies a Subpopulation and Epidemic Clones Associated with Acne. PLOS One, 2010, 5(8), e12277, 1-10.

Mayslich et al. Cutibacterium acnes as an Opportunistic Pathogen: An Update of Its Virulence-Associated Factors, Microorganisms 2021, 9, 303, 1-21.

McCoy et al. Skin Ecology during Sebaceous Drought—How Skin Microbes Respond to Isotretinoin. Journal of Investigative Dermatology, 2019, 139, 732-735.

McDowell et al. Propionibacterium acnes Types I and II Represent Phylogenetically Distinct Groups. Journal of Clinical Microbiology, 2005, 43(1), 326-334.

McDowell et al. A new phylogenetic group of Propionibacterium acnes. Journal of Medical Microbiology, 2008, 57, 218-224.

McDowell et al. A novel multilocus sequence typing scheme for the opportunistic pathogen Propionibacterium acnes and characterization of type I cell surface associated antigens. Microbiology, 2011, 157, 1990-2003.

McDowell et al. Is Cutibacterium (previously Propionibacterium) acnes a potential pathogenic factor in the aetiology of the skin disease progressive macular hypomelanosis? JEADV, 2021, 35, 338-344.

Minh et al. IQ-TREE 2: New Models and Efficient Methods for Phylogenetic Inference in the Genomic Era. Mol. Biol. Evol. 2020, 37(5), 1530-1534.

Needleman and Wunsch. A General Method Applicable to the Search for Similarities in the Amino Acid Sequence of Two Proteins, J. Mol. Biol., 1970, 48, 443-453.

Nolan et al. Treatment response to isotretinoin correlates with specific shifts in Cutibacterium acnes strain composition within the follicular microbiome. Experimental Dermatology. 2023, 32, 955-964.

Oh et al. Biogeography and individuality shape function in the human skin metagenome. Nature, 2014, 514, 59-64.

Oprica et al. Clinical and Microbiological Comparisons of Isotretinoin vs. Tetracycline in Acne Vulgaris. Acta Derm Venereol, 2007, 87, 246-254.

Page et al. Roary: rapid large-scale prokaryote pan genome analysis. Bioinformatics, 2015, 31(22), 3691-3693.

Pearson and Lipman. Improved tools for biological sequence comparison. PNAS, 1988, 85, 2444-2448.

Ravin et al. The anti-immunity system of phage-plasmid N15:identification of the antirepressor gene and its control by a small processed RNA. Molecular Microbiology, 1999, 34(5), 980-994.

Rees and Liu. Base editing: precision chemistry on the genome and transcriptome of living cells. Nat Rev Genet, 2018, 19(12), 770-788.

Schaller et al. Induction of a chemoattractive proinflammatory cytokine response after stimulation of keratinocytes with Propionibacterium acnes and coproporphyrin III. British Journal of Dermatology, 2005, 153, 66-71.

Scholz et al. A Novel High-Resolution Single Locus Sequence Typing Scheme for Mixed Populations of Propionibacterium acnes In Vivo. PLOS One, 2014, 9(8), e104199, 1-8.

Sharon et al. Functional genetic variants revealed by massively parallel precise genome editing. Cell. Oct. 4, 2018; 175(2): 544-557.e16.

Simon et al. Retrons and their applications in genome engineering, Nucleic Acids Research, 2019, 47(21), 11007-11019.

Simonart and Dramaix. Treatment of acne with topical antibiotics: lessons from clinical studies, British Journal of Dermatology, 2005, 153, 395-403.

Smith and Waterman. Comparison of Biosequences. Advances in Applied Mathematics, 1981, 2, 482-489.

Spittaels et al. Porphyrins produced by acneic Cutibacterium acnes strains activate the inflammasome by inducing K+ leakage, iScience, 2021, 24, 102575, 1-16.

Stamatakis. RAxML version 8: a tool for phylogenetic analysis and post-analysis of large phylogenies. Bioinformatics, 2014, 30(9), 1312-1313.

Teramoto et al. Classification of Cutibacterium acnes at phylotype level by MALDI-MS proteotyping. Proc. Jpn. Acad., Ser., 2019., 95, 612-623.

Wang et al. The Anti-Inflammatory Activities of Propionibacterium acnes CAMP Factor-Targeted Acne Vaccines, Journal of Investigative Dermatology, 2018, 138, 2355-2364.

Wannier et al. Improved bacterial recombineering by parallelized protein discovery, PNAS, 2020, 117(24), 13689-13698.

Webster and Cummins. Use of Bacteriophage Typing to Distinguish Propionibacterium acnes Types I and II, Journal of Clinical Microbiology, 1978, 7(1), 84-90.

Wood, et al. Improved metagenomic analysis with Kraken 2, Genome Biology, 2019, 20(257), 1-13.

Yan et al. Cas13d Is a Compact RNA-Targeting Type VI CRISPR Effector Positively Modulated by a WYL-Domain-Containing Accessory Protein, Molecular Cell, 2018, 70, 327-339.

Zhao et al. New base editors change C to A in bacteria and C to G in mammalian cells. Nature Biotechnology, 2021. 39, 35-40.

Figure 3

METHOD FOR TREATING C. acnes BACTERIA-ASSOCIATED DISEASES

CROSS-REFERENCE TO RELATED APPLICATIONS

This application claims priority to U.S. Provisional Application 63/515,223, filed on Jul. 24, 2023, the entire disclosure of which is incorporated by reference herein.

REFERENCE TO SEQUENCE LISTING SUBMITTED

This application contains a Sequence Listing which has been submitted electronically in .XML format and is hereby incorporated by reference in its entirety. Said .XML copy, created on May 6, 2025, is named SequenceListing-1726241190261 and is 52,429 bytes in size. The sequence listing contained in this .XML file is part of the specification and is hereby incorporated by reference herein in its entirety.

TECHNICAL FIELD

The present invention relates to methods for treating *C. acnes* bacteria-associated diseases, in particular for treating acne, more particularly acne vulgaris, in a subject.

BACKGROUND

*Cutibacterium acnes* is a major commensal bacterium of the skin microbiome, representing the most abundant bacteria in the hair follicle. While having a strong role in maintaining skin health, it has also been implicated in several diseases and infections, including acne vulgaris (Bruggemann et al. (2021) Front Microbiol. 12:673845) or progressive macular hypomelanosis (McDowell et al. (2021) J. Eur. Acad. Dermatol. Venereol. 35:338-344).

Acne vulgaris is a chronic inflammatory disorder of the hair follicle, for which *C. acnes* has been described as one of the etiological factors. Indeed, previous studies have shown (i) that antimicrobial treatment efficacy correlated with *C. acnes* load reduction (Lessin et al. (2020) Skin Microbiome Handbook: From Basic Research to Product Development, Ed. Nava Dayan, p289-302), (ii) that isotretinoin, the most efficient drug available so far to treat acne, led to a reduction in *C. acnes* load (Oprica et al. (2007) Acta Derm Venerol 87:246-254; Nolan et al. (2023) Exp. Dermatol. 32:955-964; McCoy et al. (2019) J Invest. Dermatol. 139:732-735; Kelhälä et al. (2017) Exp. Dermatol. 27:30-36), (iii) that antibiotic inefficacy correlated with the presence of *C. acnes* antibiotic resistant strains (Simonart et al. (2005) British J. Dermatol. 153:395-403); (iv) that *C. acnes* triggered acne-like inflammation in different in vitro (Laclaverie et al. (2021) Exp. Dermatol. 30:347-357) and in vivo models (Kolar et al. (2019) J CI Insight 4(5):e124687), and (v) that patients suffering from acne vulgaris had anti-*C. acnes* antibodies (Wang et al. (2018)J. Invest. Dermatol. 138:2355-2364; Huang et al. (2021) Front. Microbiol. 12:709562).

Since *C. acnes* also plays an important role in maintaining skin health, it is of major importance to identify those *C. acnes* types that are involved in inflammatory disorders (e.g. acne vulgaris) and distinguish them from non-inflammatory disorders-associated *C. acnes* types.

Different studies tried to achieve such identification but with a poor outcome. In 2013, Fitz-Gibbon et al. compared the skin microbiome at the strain level and genome level of *C. acnes* between acne patients and healthy individuals. They showed a significant enrichment of specific *C. acnes* ribotypes in acne patients (namely RT4, RT5, RT8 and RT10 ribotypes) and a significant enrichment of another specific *C. acnes* ribotype in healthy subjects (namely RT6 ribotype) (Fitz-Gibbon et al. (2013) J. Invest. Dermatol. 133:2152-2160). However, not all acne patients showed a clear presence of *C. acnes* bacteria belonging to an acne-associated ribotype. Therefore, the distinction of *C. acnes* bacteria between different ribotypes did not enable the effective identification of *C. acnes* bacteria involved in acne.

Based on the whole genome sequencing of *C. acnes* clones belonging to different ribotypes, Fitz-Gibbon et al. also showed that 3 loci (referred to by the authors as loci 1, 2 and 3) were specific to ribotypes RT4 and RT5, which are enriched in acne patients (Fitz-Gibbon et al. (2013) J. Invest. Dermatol. 133:2152-2160). However, once again the presence of these loci does not enable the specific identification of acne-associated strains, since *C. acnes* strains belonging to the RT8 ribotype (which is enriched in acne patients) are not enriched in these 3 loci, and *C. acnes* strains belonging to the RT1 ribotype (abundant in both acne patients and healthy subjects) can carry loci 1, 2 and 3.

Later, the same lab performed a metagenomic profiling of acne and healthy follicular plugs and showed that the RT4, RT5 and RT8 ribotypes were more abundant and prevalent in acne patients, the RT2 and RT6 ribotypes were more abundant and prevalent in healthy subjects, and that there was an enrichment of specific genes contained in the previously identified loci 1, 2 and 3 (Barnard et al. (2016) Scientific Reports 6:39491). However, a large fraction of acne metagenomic samples did not carry loci 1, 2 and 3, and, inversely, some healthy metagenomic samples carried locus 1 or 3. This confirms that ribotypes and loci 1, 2 and 3 are not suitable to efficiently identify acne-associated strains.

Other different typing methods (including multi-locus sequence typing (MLST), single-locus sequence typing (SLST), Belfast scheme using 7 target genes, multiplex touchdown PCR, Aarhus scheme using 9 target genes, MALDI-TOF MS-based typing, and MLVA typing using the polymorphism of 13 VNTRs) have been used to try to discriminate acne-associated strains and non acne-associated strains, but the types defined using those methods are inconsistent when compared with each other, and none of them enables a clear and efficient identification of acne-associated strains (Mayslich et al. (2021) Microorganisms 9:203).

There is thus an important need for tools enabling a clear and efficient identification of acne-associated strains, so that these strains can be specifically targeted while maintaining non acne-associated strains alive and in good shape.

Some studies reported a higher production of certain porphyrins (mainly coproporphyrin III) by acne-associated strains (Johnson et al. (2016) mSphere 1(1):e00023-15; Barnard et al. (2020) mSphere 5:e00793-19). Porphyrins were considered to be of interest because they were shown, when extracted from acne-associated strains, to activate the inflammasome, offering an explanation for *C. acnes* role in inflammation (Spittaels et al. (2021) iScience 24:102575). Therefore, using the difference in porphyrin production could be a way of discriminating acne-associated strains from non acne-associated strains.

Enzymes involved in the porphyrin pathway are encoded by 8 hem genes in a locus that is conserved across *C. acnes* strains and represented on FIG. 5. Additionally, the Huiying Li team reported the presence of a putative repressor from the deoR family (also known as glpR) in the proximity of this locus in non acne-associated strains (Johnson et al. (2016) mSphere 1(1):e00023-15; Barnard et al. (2020) mSphere 5:e00793-19), and therefore speculated that this deoR gene could be of interest in the diagnosis and/or treatment of acne vulgaris (WO2017/136738). However, as highlighted by the authors, "[s]ince deorR was found to be expressed in both high- and low-level-porphyrin-producing strains, [they] sought to determine if there were differences in the deoR gene sequence that could explain variations in regulation and porphyrin production among the strains. ( . . . ) [However, they] did not identify any single nucleotide polymorphisms (SNPs) that were uniquely shared by strains from clades IB-3 and IC and that could potentially explain the increased porphyrin production in these lineages" (see Barnard et al. (2020) mS phere 5:e00793-19).

Therefore, there is still an important need for tools enabling a robust and efficient identification of acne-associated strains, so that these strains can be specifically targeted while maintaining non acne-associated strains alive and in good shape.

The present invention meets this need.

SUMMARY OF THE INVENTION

The present invention arises from the unexpected finding by the inventors that a set of 218 SNPs across the hem locus (comprising the genes hemA, hemB, hemC, hemD, hemE, hemH, hemL, and hemY) allows to classify the known *C. acnes* strain diversity in 2 groups, herein called α-type and β-type. Importantly, this new typing strictly correlates with the published porphyrin production levels, in contrast to the deoR gene, with α-type containing all *C. acnes* producing high amounts of porphyrins whereas β-type contain all the *C. acnes* producing low or no amounts of porphyrins. Moreover, after developing a method for the estimation of relative abundances of α-type and β-type *C. acnes* strains in shotgun metagenomic sequencing data, and applying it to a public data set associated to a study characterizing the skin microbiome in acne vulgaris (Barnard et al. (2016) Scientific Reports 6:39491), the present inventors demonstrated that α-type *C. acnes* strains formed significantly larger fraction of the *C. acnes* population in patients suffering from acne vulgaris than healthy subjects.

The present invention thus relates to a method for treating or preventing a *Cutibacterium acnes* bacteria-associated disease in a subject, said method comprising modulating, in particular reducing, in said subject, the ratio of the amount of α-type *C. acnes* bacteria to the amount of β-type *C. acnes* bacteria,
wherein α-type *C. acnes* bacteria are *C. acnes* bacteria (i) which comprise at least 90% of the following nucleotide variants in the hem locus:
in the hemA gene: T173, A479, T506, A614, T629, C671, T971, A989, T1085, and T1094, wherein the positions are defined with reference to sequence SEQ ID NO: 3,
in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4,
in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5,
in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6,
in the hemE gene: T241, T476, A530, T704, A728, G767, T834, A867, A872, A882, and A957, wherein the positions are defined with reference to sequence SEQ ID NO: 7,
in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G 1532, T1598, T1712, A1850, G 1901, A1926, C1931, and C1997, wherein the positions are defined with reference to sequence SEQ ID NO: 8,
in the hemL gene: T107, C197, T229, A242, C310, A338, A374, T389, G392, T442, C467, G470, C482, G518, and C641, wherein the positions are defined with reference to sequence SEQ ID NO: 9, and
in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10,
and/or
(ii) in which the nucleic acid sequence of the hem locus is at least 97% identical to the sequence SEQ ID NO: 1;
and
wherein β-type *C. acnes* bacteria are *C. acnes* bacteria which are not α-type *C. acnes* bacteria.

The present invention also relates to a method for treating or preventing a *C. acnes* bacteria-associated disease in a subject, said method comprising specifically reducing the amount of α-type *C. acnes* bacteria in said subject,
wherein α-type *C. acnes* bacteria are *C. acnes* bacteria (i) which comprise at least 90% of the following nucleotide variants in the hem locus:
in the hemA gene: T173, A479, T506, A614, T629, C671, T971, A989, T1085, and T1094, wherein the positions are defined with reference to sequence SEQ ID NO: 3,
in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4,
in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5,
in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention also relates to a method for treating or preventing a *C. acnes* bacteria-associated disease in a subject, said method comprising genetically modifying a DNA sequence in α-type *C. acnes* bacteria in said subject, to generate at least one change, preferably in the hem locus of said α-type *C. acnes* bacteria, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention also relates to a method for treating or preventing a *C. acnes* bacteria-associated disease in a subject, said method comprising increasing the amount of β-type *C. acnes* bacteria in said subject, wherein β-type *C. acnes* bacteria are *C. acnes* bacteria which are not α-type *C. acnes* bacteria, α-type *C. acnes* bacteria being *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention further concerns a composition for use in the treatment or prevention of a *C. acnes* bacteria-associated disease in a subject, said composition comprising a therapeutic or prophylactic agent inducing the modulation, preferably the reduction, in said subject, of the ratio of the amount of α-type *C. acnes* bacteria to the amount of β-type *C. acnes* bacteria, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, T787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10, and/or (ii) in which the nucleic acid sequence of the hem locus is at least 97% identical to the sequence SEQ ID NO: 1;

and wherein β-type *C. acnes* bacteria are *C. acnes* bacteria which are not α-type *C. acnes* bacteria.

The present invention also concerns a composition for use in the treatment or prevention of a *C. acnes* bacteria-associated disease in a subject, said composition comprising a therapeutic or prophylactic agent which specifically reduces the amount of α-type *C. acnes* bacteria in said subject, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, T787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G 1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention also concerns a composition for use in the treatment or prevention of a *C. acnes* bacteria-associated disease in a subject, said composition comprising a therapeutic or prophylactic agent which genetically modifies a DNA sequence in α-type *C. acnes* bacteria in said subject, to generate at least one change, preferably in the hem locus of said α-type *C. acnes* bacteria, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G 1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention further concerns a composition for use in the treatment or prevention of a *C. acnes* bacteria-associated disease in a subject, said composition comprising a therapeutic or prophylactic agent which increases the amount of β-type *C. acnes* bacteria in said subject, wherein β-type *C. acnes* bacteria are *C. acnes* bacteria which are not α-type *C. acnes* bacteria, α-type *C. acnes* bacteria being *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention also concerns a method for treating or preventing a *C. acnes* bacteria-associated disease in a subject, said method comprising specifically reducing the expression of at least one hem locus protein in α-type *C. acnes* bacteria in said subject, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

The present invention also concerns a composition for use in the treatment or prevention of a *C. acnes* bacteria-associated disease in a subject, said composition comprising a therapeutic or prophylactic agent which specifically reduces the expression of at least one hem locus protein in α-type *C. acnes* bacteria in said subject by genetically modifying a DNA sequence in α-type *C. acnes* bacteria in said subject, to generate at least one change, preferably in the hem locus of said α-type *C. acnes* bacteria, and wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

Another object of the invention concerns a pharmaceutical composition comprising a phage, recombinant phage, packaged phagemid, plasmid, DNA- or RNA-containing vesicle, extracellular vesicle, bacteria or engineered bacteria, which encodes a programmable nuclease, or a gene editing enzyme or system, designed to specifically target a α-type *C. acnes* bacteria, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G 1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1.

Another object of the invention concerns a method for determining if a subject is at risk of developing acne, in particular acne vulgaris, said method comprising the steps of:

a) determining the presence and/or amount of α-type *C. acnes* bacteria in a sample, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G 1268, G 1278, T1295, T1318, A1336, G 1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1, and b) based on the presence and/or amount determined at step a), determining if said subject is at risk of developing acne, in particular acne vulgaris.

Another object of the invention concerns a method of diagnosing acne, in particular acne vulgaris in a subject, said method comprising the steps of:

a) determining the presence and/or amount of α-type *C. acnes* bacteria in a sample, wherein α-type *C. acnes* bacteria are *C. acnes* bacteria (i) which comprise at least 90% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G 1278, T1295, T1318, A1336, G1343, C1346, G 1355, T1359 and C1395, wherein the positions are defined with reference to sequence SEQ ID NO: 10, and/or (ii) in which the nucleic acid sequence of the hem locus is at least 97% identical to the sequence SEQ ID NO: 1, and b) based on the presence and/or amount determined at step a), diagnosing acne, in particular acne vulgaris, in said subject.

DETAILED DESCRIPTION

α-type *C. acnes* bacteria and β-type *C. acnes* bacteria

*Cutibacterium acnes* (formerly *Propionibacterium acnes*) is a gram-positive rod-shaped aerotolerant bacteria, first isolated from skin in 1897. It belongs to the order Actinomycetales, is part of the Propionibacteriaceae family, and belongs to the genus *Cutibacterium*. *C. acnes* is one of the most prevalent and abundant bacteria on human skin where it can be found both on the skin surface (stratum corneum) and in the hair follicle. Inside the hair follicle, it is in direct contact with a large diversity of living cells such as keratinocytes, stem cells, sebaceous cells and immune cells, unlike on the stratum corneum where it is mostly in contact with the dead corneocyte. *C. acnes* is a commensal bacterium but has also been associated with several skin diseases such as acne vulgaris or progressive macular hypomelanosis.

*C. acnes* strains were previously classified into two main types, I and II, on the basis of their cell wall carbohydrate content and serum lectin responses (Johnson et al. (1982)J Bacteriol. 109(3):1047-66). Subclusters of these types were then identified on the basis of the R ecA and tly genes and the use of the QUBPa1 and QUBPa2 antibodies (McDowell et al. (2005) J Clin Microbiol. 43(1):326-334). An additional phylotype, type III, corresponding to strains with filamentous appendages, was then added to the classification (McDowell et al. (2008)J Medical Microbiol. 57:218-224). Multi-locus sequence typing (MLST) methods were also developed to increase typing resolution. The Belfast scheme, based on 7 target genes, differentiates type I into clades IA1, IA2, IB and IC (McDowell et al. (2011) Microbiology 157:1990-2003), while the Aarhus scheme, based on 9 target genes, differentiates type I into clades I-1a, I-1b and I-2 (Lomholt et al. (2010) PLoS ONE 5(8):e12277). SLST and whole-genome sequencing (WGS) techniques were then used to develop new methods differentiating *C. acnes* strains into SLST types (Scholz et al. (2014) P LoS ONE 9(8): e104199).

Mass spectrometry-based methods were also used to characterize *C. acnes* strains, and, when associated with profiling of ribosomal subunit proteins, in MALDI-MS prototyping, enabled the discrimination of all phylotypes mentioned above (Teramoto et al. (2019) Proc. J pn. Acad. Ser. B 95:612-623).

Based on 16S rRNA gene analysis, *C. acnes* strains were also divided in ribotypes defined and referenced in Fitz-Gibbon et al. (2013) J. Invest. Dermatol. 133:2152-2160.

However, as underlined by Mayslich et al. (Mayslich et al. (2021) Microorganisms 9:303), there is an important need of standardization among all the above nomenclatures, and, as highlighted above, none of them enables a robust and efficient distinction between acne strains and non acne-associated strains.

The inventors of the present invention identified a set of 218 SNPs across the hem locus (comprising the genes hemA, hemB, hemC, hemD, hemE, hemH, hemL, and hemY) which allows to classify the known *C. acnes* strain diversity in 2 groups, herein called α-type and β-type. Importantly, this new typing strictly correlates with the published porphyrin production levels, in contrast to the deoR gene, with α-type containing all *C. acnes* producing high amounts of porphyrins whereas β-type contains all the *C. acnes* producing low or no amounts of porphyrins. Moreover, after developing a method for the estimation of relative abundances of α-type and β-type *C. acnes* strains in shotgun metagenomic sequencing data, and applying it to a public data set associated to a study characterizing the skin microbiome in acne vulgaris (Barnard et al. (2016) Scientific Reports 6:39491), the present inventors demonstrated that α-type *C. acnes* strains formed significantly larger fraction of the *C. acnes* population in patients suffering from acne vulgaris than healthy subjects.

The inventors thereby identified α-type *C. acnes* bacteria as being *C. acnes* bacteria in which at least 90% of the marker positions defined in Table 1 below have the nucleotide variant defined as "alpha variant", the positions being defined with respect to reference gene sequence SEQ ID NO: 3 for hemA gene, SEQ ID NO:4 for hemB gene, SEQ ID NO:5 for hemC gene, SEQ ID NO: 6 for hemD gene, SEQ ID NO: 7 for hemE gene, SEQ ID NO: 8 for hemH gene, SEQ ID NO: 9 for hemL gene and SEQ ID NO: 10 for hemY gene.

Values indicated in the column entitled "reference position (0-based)" are 0-based which means that the first nucleotide in the gene sequence is indexed as 0. As will be easily understood by the skilled person, a position can alternatively be defined in "1-based" way, meaning that the first nucleotide in the gene sequence is indexed as 1. In that case, all the "0-based" defined positions would be incremented by 1. For example, the "0-based" defined position T173 in the hemA gene is identical to the "1-based" defined position T174 in the hemA gene. Values indicated in the column entitled "reference position (1-based)" are 1-based. In the present document, unless specifically indicated, values of the reference positions are 0-based.

TABLE 1

Set of reference position for alpha/beta types of the hem locus

| gene | alpha variant | beta variant | reference position (0-based) | reference position (1-based) |
|------|---------------|--------------|------------------------------|------------------------------|
| hemA | T | G | 173 | 174 |
| hemA | A | G | 479 | 480 |
| hemA | T | C | 506 | 507 |
| hemA | A | G | 614 | 615 |
| hemA | T | G | 629 | 630 |
| hemA | C | A | 671 | 672 |
| hemA | T | C | 971 | 972 |
| hemA | A | G | 989 | 990 |
| hemA | T | C | 1085 | 1086 |
| hemA | T | C | 1094 | 1095 |
| hemB | C | T | 142 | 143 |
| hemB | A | G | 155 | 156 |
| hemB | A | G | 176 | 177 |
| hemB | A | G | 183 | 184 |
| hemB | C | T | 224 | 225 |
| hemB | C | T | 245 | 246 |
| hemB | G | A | 248 | 249 |
| hemB | T | C | 281 | 282 |
| hemB | G | A | 311 | 312 |
| hemB | C | T | 314 | 315 |
| hemB | T | C | 346 | 347 |
| hemB | C | T | 374 | 375 |
| hemB | G | T | 377 | 378 |
| hemB | C | T | 452 | 453 |
| hemB | T | C | 626 | 627 |
| hemB | C | G | 683 | 684 |
| hemB | A | G | 693 | 694 |
| hemB | A | G | 720 | 721 |
| hemB | C | T | 738 | 739 |
| hemB | C | T | 794 | 795 |
| hemB | A | C | 920 | 921 |
| hemB | T | G | 944 | 945 |
| hemB | T | C | 992 | 993 |
| hemB | G | C | 1022 | 1023 |
| hemB | T | C | 1031 | 1032 |
| hemC | G | A | 77 | 78 |
| hemC | A | G | 96 | 97 |
| hemC | C | G | 149 | 150 |
| hemC | A | G | 233 | 234 |
| hemC | T | C | 236 | 237 |
| hemC | T | C | 255 | 256 |
| hemC | A | G | 257 | 258 |
| hemC | A | C | 260 | 261 |
| hemC | C | T | 317 | 318 |
| hemC | A | G | 347 | 348 |
| hemC | T | C | 425 | 426 |
| hemC | T | C | 437 | 438 |
| hemC | A | G | 464 | 465 |
| hemC | A | G | 486 | 487 |
| hemC | A | G | 487 | 488 |
| hemC | C | T | 488 | 489 |
| hemC | A | G | 524 | 525 |
| hemC | A | G | 545 | 546 |
| hemC | A | G | 590 | 591 |
| hemC | T | C | 605 | 606 |
| hemC | A | G | 644 | 645 |
| hemC | A | G | 665 | 666 |
| hemC | C | T | 710 | 711 |
| hemC | C | G | 713 | 714 |
| hemC | A | G | 737 | 738 |
| hemC | A | G | 770 | 771 |
| hemC | A | G | 776 | 777 |
| hemC | T | A | 785 | 786 |
| hemC | T | C | 802 | 803 |
| hemC | G | A | 830 | 831 |
| hemC | C | T | 842 | 843 |
| hemC | T | C | 845 | 846 |
| hemC | G | A | 855 | 856 |
| hemC | C | G | 893 | 894 |
| hemC | A | T | 896 | 897 |
| hemC | C | T | 897 | 898 |
| hemC | G | A | 902 | 903 |
| hemC | G | T | 908 | 909 |
| hemC | A | G | 941 | 942 |
| hemC | A | G | 947 | 948 |
| hemD | T | C | 11 | 12 |
| hemD | T | C | 41 | 42 |
| hemD | T | C | 50 | 51 |
| hemD | A | G | 150 | 151 |
| hemD | T | C | 155 | 156 |
| hemD | G | A | 159 | 160 |
| hemD | G | T | 176 | 177 |
| hemD | T | C | 257 | 258 |
| hemD | C | T | 266 | 267 |
| hemD | T | C | 278 | 279 |
| hemD | G | C | 323 | 324 |
| hemD | A | G | 324 | 325 |
| hemD | T | C | 362 | 363 |
| hemD | T | C | 367 | 368 |
| hemD | T | C | 374 | 375 |
| hemD | G | A | 387 | 388 |
| hemD | A | G | 398 | 399 |
| hemD | A | G | 399 | 400 |
| hemD | T | C | 407 | 408 |
| hemD | G | A | 422 | 423 |
| hemD | G | A | 425 | 426 |
| hemD | G | A | 432 | 433 |
| hemD | A | G | 446 | 447 |
| hemD | A | G | 459 | 460 |
| hemD | T | C | 464 | 465 |
| hemD | G | A | 595 | 596 |
| hemD | T | C | 617 | 618 |
| hemD | T | A | 643 | 644 |
| hemD | A | G | 644 | 645 |
| hemD | C | T | 680 | 681 |
| hemE | T | C | 241 | 242 |
| hemE | T | C | 476 | 477 |
| hemE | A | G | 530 | 531 |
| hemE | T | C | 704 | 705 |
| hemE | A | G | 728 | 729 |
| hemE | G | C | 767 | 768 |
| hemE | T | A | 834 | 835 |

TABLE 1-continued

Set of reference position for alpha/beta types of the hem locus

| gene | alpha variant | beta variant | reference position (0-based) | reference position (1-based) |
|---|---|---|---|---|
| hemE | A | G | 867 | 868 |
| hemE | A | G | 872 | 873 |
| hemE | A | C | 882 | 883 |
| hemE | A | G | 957 | 958 |
| hemH | T | C | 11 | 12 |
| hemH | T | C | 23 | 24 |
| hemH | A | G | 48 | 49 |
| hemH | T | C | 89 | 90 |
| hemH | C | T | 188 | 189 |
| hemH | G | A | 338 | 339 |
| hemH | T | C | 464 | 465 |
| hemH | T | C | 470 | 47 |
| hemH | G | A | 536 | 537 |
| hemH | T | C | 548 | 549 |
| hemH | T | C | 608 | 609 |
| hemH | G | A | 626 | 627 |
| hemH | T | C | 632 | 633 |
| hemH | T | C | 641 | 642 |
| hemH | T | C | 67 | 672 |
| hemH | T | C | 674 | 675 |
| hemH | C | T | 683 | 684 |
| hemH | C | T | 689 | 690 |
| hemH | A | T | 740 | 741 |
| hemH | G | A | 745 | 746 |
| hemH | G | A | 787 | 788 |
| hemH | A | G | 797 | 798 |
| hemH | T | C | 893 | 894 |
| hemH | A | T | 898 | 899 |
| hemH | T | C | 1034 | 1035 |
| hemH | T | C | 1039 | 1040 |
| hemH | T | C | 1046 | 1047 |
| hemH | C | G | 1071 | 1072 |
| hemH | G | A | 1095 | 1096 |
| hemH | C | T | 1109 | 1110 |
| hemH | T | C | 1153 | 1154 |
| hemH | T | C | 1358 | 1359 |
| hemH | G | C | 1496 | 1497 |
| hemH | C | T | 1511 | 1512 |
| hemH | C | T | 1527 | 1528 |
| hemH | G | A | 1532 | 1533 |
| hemH | T | C | 1598 | 1599 |
| hemH | T | C | 1712 | 1713 |
| hemH | A | G | 1850 | 1851 |
| hemH | G | C | 1901 | 1902 |
| hemH | A | G | 1926 | 1927 |
| hemH | C | T | 1931 | 1932 |
| hemH | C | T | 1997 | 1998 |
| hemL | T | C | 107 | 108 |
| hemL | C | T | 197 | 198 |
| hemL | T | A | 229 | 230 |
| hemL | A | G | 242 | 243 |
| hemL | C | A | 310 | 311 |
| hemL | A | G | 338 | 339 |
| hemL | A | G | 374 | 375 |
| hemL | T | C | 389 | 390 |
| hemL | G | T | 392 | 393 |
| hemL | T | C | 442 | 443 |
| hemL | C | T | 467 | 468 |
| hemL | G | A | 470 | 471 |
| hemL | C | T | 482 | 483 |
| hemL | G | T | 518 | 519 |
| hemL | C | G | 641 | 642 |
| hemY | A | G | 89 | 90 |
| hemY | A | G | 236 | 237 |
| hemY | A | G | 354 | 355 |
| hemY | C | T | 383 | 384 |
| hemY | C | T | 392 | 393 |
| hemY | A | G | 395 | 396 |
| hemY | T | C | 398 | 399 |
| hemY | T | C | 465 | 466 |
| hemY | T | C | 474 | 475 |
| hemY | C | T | 521 | 522 |
| hemY | T | C | 538 | 539 |
| hemY | C | T | 566 | 567 |
| hemY | A | C | 593 | 594 |
| hemY | A | C | 767 | 768 |
| hemY | T | A | 782 | 783 |
| hemY | G | A | 863 | 864 |
| hemY | G | A | 920 | 921 |
| hemY | T | A | 927 | 928 |
| hemY | A | G | 932 | 933 |
| hemY | G | A | 935 | 936 |
| hemY | C | A | 979 | 980 |
| hemY | G | C | 989 | 990 |
| hemY | C | G | 1019 | 1020 |
| hemY | T | C | 1055 | 1056 |
| hemY | G | A | 1091 | 1092 |
| hemY | T | C | 1136 | 1137 |
| hemY | G | A | 1143 | 1144 |
| hemY | G | T | 1152 | 1153 |
| hemY | T | C | 1166 | 1167 |
| hemY | T | G | 1172 | 1173 |
| hemY | A | G | 1176 | 1177 |
| hemY | T | C | 1184 | 1185 |
| hemY | C | T | 1199 | 1200 |
| hemY | C | T | 1205 | 1206 |
| hemY | G | A | 1268 | 1269 |
| hemY | G | A | 1278 | 1279 |
| hemY | T | C | 1295 | 1296 |
| hemY | T | C | 1318 | 1319 |
| hemY | A | G | 1336 | 1337 |
| hemY | G | A | 1343 | 1344 |
| hemY | C | T | 1346 | 1347 |
| hemY | G | C | 1355 | 1356 |
| hemY | T | G | 1359 | 1360 |
| hemY | C | G | 1395 | 1396 |

In the context of the invention, α-type *C. acnes* bacteria are thus preferably *C. acnes* bacteria which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G 387, A398, A399, T407, G 422, G 425, G 432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10.

Alternatively, α-type *C. acnes* bacteria may be *C. acnes* bacteria which comprise at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217 or all of the alpha nucleotide variants as defined in Table 1.

Alternatively, using "1-based" defined positions, α-type *C. acnes* bacteria may be *C. acnes* bacteria which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the following nucleotide variants in the hem locus:

in the hemA gene: T174, A480, T507, A615, T630, C672, T972, A990, T1086, and T1095, wherein the positions are defined with reference to sequence SEQ ID NO: 3, in the hemB gene: C143, A156, A177, A184, C225, C246, G249, T282, G312, C315, T347, G375, G378, C453, T627, C684, A694, A721, C739, C795, A921, T945, T993, G1023, and T1032, wherein the positions are defined with reference to sequence SEQ ID NO: 4, in the hemC gene: G78, A97, C150, A234, T237, T256, A258, A261, C318, A348, T426, T438, A465, A487, A488, C489, A525, A546, A591, T606, A645, A666, C711, C714, A738, A771, A777, T786, T803, G831, C843, T846, G856, C894, A897, C898, G903, G909, A942, and A948, wherein the positions are defined with reference to sequence SEQ ID NO: 5, in the hemD gene: T12, T42, T51, A151, T156, G160, G177, T258, C267, T279, G324, A325, T363, T368, T375, G388, A399, A400, T408, G423, G426, G433, A447, A460, T465, G596, T618, T644, A645, and C681, wherein the positions are defined with reference to sequence SEQ ID NO: 6, in the hemE gene: T242, T477, A531, T705, A729, G768, T835, A868, A873, A883, and A958, wherein the positions are defined with reference to sequence SEQ ID NO: 7, in the hemH gene: T12, T24, A49, T90, C189, G339, T465, T471, G537, T549, T609, G627, T633, T642, T672, T675, C684, C690, A741, G746, G788, A798, T894, A899, T1035, T1040, T1047, C1072, G1096, C1110, T1154, T1359, G1497, C1512, C1528, G1533, T1599, T1713, A1851, G1902, A1927, C1932, and C1998, wherein the positions are defined with reference to sequence SEQ ID NO: 8, in the hemL gene: T108, C198, T230, A243, C311, A339, A375, T390, G393, T443, C468, G471, C483, G519, and C642, wherein the positions are defined with reference to sequence SEQ ID NO: 9, and in the hemY gene: A90, A237, A355, C384, C393, A396, T399, T466, T475, C522, T539, C567, A594, A768, T783, G864, G921, T928, A933, G936, C980, G990, C1020, T1056, G1092, T1137, G1144, G1153, T1167, T1173, A1177, T1185, C1200, C1206, G1269, G1279, T1296, T1319, A1337, G1344, C1347, G1356, T1360 and C1396, wherein the positions are defined with reference to sequence SEQ ID NO: 10.

By "hem locus" is meant herein a locus included in the porphyrin biosynthesis loci of *C. acnes* bacteria and comprising 8 hem genes, namely the hemA, hemB, hemC, hemD, hemE, hemH, hemL and hemY genes.

Alternatively or in addition, in the context of the invention α-type *C. acnes* bacteria are *C. acnes* bacteria in which the nucleic acid sequence of the hem locus (which comprises the genes hemA, hemB, hemC, hemD, hemE, hemH, hemL and hemY) is at least 97% identical, in particular at least 97.1% identical, at least 97.2% identical, at least 97.3% identical, at least 97.4% identical, at least 97.5% identical, at least 97.6% identical, at least 97.7% identical, at least 97.8% identical, at least 97.9% identical, at least 98% identical, at least 98.1% identical, at least 98.2% identical, at least 98.3% identical, at least 98.4% identical, at least 98.5% identical, at least 98.6% identical, at least 98.7% identical, at least 98.8% identical, at least 98.9% identical, at least 99% identical, at least 99.1% identical, at least 99.2% identical, at least 99.3% identical, at least 99.4% identical, at least 99.5% identical, at least 99.6% identical, at least 99.7% identical, at least 99.8% identical, at least 99.9% identical, or 100% identical, to the sequence SEQ ID NO: 1.

Preferably, α-type *C. acnes* bacteria are *C. acnes* bacteria
(i) which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the alpha nucleotide variants as defined in Table 1, or which comprise at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217 or all of the alpha nucleotide variants as defined in Table 1, and
(ii) in which the nucleic acid sequence of the hem locus is at least 97% identical, in particular at least 97.1% identical, at least 97.2% identical, at least 97.3% identical, at least 97.4% identical, at least 97.5% identical, at least 97.6% identical, at least 97.7% identical, at least 97.8% identical, at least 97.9% identical, at least 98% identical, at least 98.1% identical, at least 98.2% identical, at least 98.3% identical, at least 98.4% identical, at least 98.5% identical, at least 98.6% identical, at least 98.7% identical, at least 98.8% identical, at least 98.9% identical, at least 99% identical, at least 99.1% identical, at least 99.2% identical, at least 99.3% identical, at least 99.4% identical, at least 99.5% identical, at least 99.6% identical, at least 99.7% identical, at least 99.8% identical, at least 99.9% identical, or 100% identical, to the sequence SEQ ID NO: 1.

In the context of the invention, β-type *C. acnes* bacteria are *C. acnes* bacteria which are not α-type *C. acnes* bacteria as defined above.

Preferably, β-type *C. acnes* bacteria are *C. acnes* bacteria which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the following nucleotide variants in the hem locus:

in the hemA gene: G173, G479, C506, G614, G629, A671, C971, G989, C1085, and C1094, wherein the positions are defined with reference to sequence SEQ ID NO: 3, in the hemB gene: T142, G155, G176, G183, T224, T245, A248, C281, A311, T314, C346,T374,T377,T452, C626, G683, G693, G720,T738,T794, C920, G944, C992, C1022, and C1031, wherein the positions are defined with reference to sequence SEQ ID NO: 4, in the hemC gene: A77, G96, G149, G233, C236, C255, G257, C260, T317, G347, C425, C437, G464, G486, G487, T488, G524, G545, G590, C605, G644, G665, T710, G713, G737, G770, G776, A785, C802, A830, T842, C845, A855, G893, T896, T897, A902, T908, G941, and G947, wherein the positions are defined with reference to sequence SEQ ID NO: 5, in the hemD gene: C11, C41, C50, G150, C155, A159, T176, C257, T266, C278, C323, G324, C362, C367, C374, A387, G398, G399, C407, A422, A425, A432, G446, G459, C464, A595, C617, A643, G644, and T680, wherein the positions are defined with reference to sequence SEQ ID NO: 6, in the hemE gene: C241, C476, G530, C704, C728, C767, A834, G867, G872, C882, and G957, wherein the positions are defined with reference to sequence SEQ ID NO: 7, in the hemH gene: C11, C23, G48, C89, T188, A338, C464, C470, A536, C548, C608, A626, C632, C641, C671, C674, T683, T689, T740, A745, A787, G797, C893, T898, C1034, C1039, C1046, G1071, A1095, T1109, C1153, C1358, C1496, T1511, T1527, A1532, C1598, C1712, G1850, C1901, G1926, T1931, and T1997, wherein the positions are defined with reference to sequence SEQ ID NO: 8, in the hemL gene: C107, T197, A229, G242, A310, G338, G374, C389, T392, C442, T467, A470, T482, T518, and G 641, wherein the positions are defined with reference to sequence SEQ ID NO: 9, and in the hemY gene: G89, G236, G354, T383, T392, G395, C398, C465, C474, T521, C538, T566, C593, C767, A782, A863, A920, A927, G932, A935, A979, C989, G1019, C1055, A1091, C1136, A1143, T1152, C1166, G1172, G1176, C1184, T1199, T1205, A1268, A1278, C1295, C1318, G1336, A1343, T1346, C1355, G1359 and G1395, wherein the positions are defined with reference to sequence SEQ ID NO: 10.

Alternatively, using "1-based" defined positions, β-type *C. acnes* bacteria may be *C. acnes* bacteria which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the following nucleotide variants in the hem locus in the hemA gene: G174, G480, C507, G615, G630, A672, C972, G990, C1086, and C1095, wherein the positions are defined with reference to sequence SEQ ID NO: 3, in the hemB gene: T143, G156, G177, G 184, T225, T246, A249, C282, A312, T315, C347, T375, T378, T453, C627, G684, G694, G721, T739, T795, C921, G945, C993, C1023, and C1032, wherein the positions are defined with reference to sequence SEQ ID NO: 4, in the hemC gene: A78, G97, G150, G234, C237, C256, G258, C261, T318, G348, C426, C438, G465, G487, G488, T489, G525, G546, G591, C606, G645, G666, T711, G714, G738, G771, G777, A786, C803, A831, T843, C846, A856, G894, T897, T898, A903, T909, G942, and G948, wherein the positions are defined with reference to sequence SEQ ID NO: 5, in the hemD gene: C12, C42, C51, G151, C156, A160, T177, C258, T267, C279, C324, G325, C363, C368, C375, A388, G399, G400, C408, A423, A426, A433, G447, G460, C465, A596, C618, A644, G645, and T681, wherein the positions are defined with reference to sequence SEQ ID NO: 6, in the hemE gene: C242, C477, G531, C705, G729, C768, A835, G868, G873, C883, and G958, wherein the positions are defined with reference to sequence SEQ ID NO: 7, in the hemH gene: C12, C24, G49, C90, T189, A339, C465, C471, A537, C549, C609, A627, C633, C642, C672, C675, T684, T690, T741, A746, A788, G798, C894, T899, C1035, C1040, C1047, G1072, A1096, T1110, C1154, C1359, C1497, T1512, T1528, A1533, C1599, C1713, G1851, C1902, G1927, T1932, and T1998, wherein the positions are defined with reference to sequence SEQ ID NO: 8, in the hemL gene: C108, T198, A230, G 243, A311, G 339, G375, C390, T393, C443, T468, A471, T483, T519, and G642, wherein the positions are defined with reference to sequence SEQ ID NO: 9, and in the hemY gene: G90, G237, G355, T384, T393, G396, C399, C466, C475, T522, C539, T567, C594, C768, A783, A864, A921, A928, G933, A936, A980, C990, G1020, C1056, A1092, C1137, A1144, T1153, C1167, G1173, G1177, C1185, T1200, T1206, A1269, A1279, C1296, C1319, G1337, A1344, T1347, C1356, G1360 and G1396, wherein the positions are defined with reference to sequence SEQ ID NO: 10.

Alternatively, β-type *C. acnes* bacteria may be *C. acnes* bacteria which comprise at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217 or all of the beta nucleotide variants as defined in Table 1.

Alternatively or in addition, β-type *C. acnes* bacteria are preferably *C. acnes* bacteria in which the nucleic acid sequence of the hem locus (which comprises the genes hemA, hemB, hemC, hemD, hemE, hemH, hemL, and hemY) is at least 97% identical, in particular at least 97.1% identical, at least 97.2% identical, at least 97.3% identical, at least 97.4% identical, at least 97.5% identical, at least 97.6% identical, at least 97.7% identical, at least 97.8% identical, at least 97.9% identical, at least 98% identical, at least 98.1% identical, at least 98.2% identical, at least 98.3% identical, at least 98.4% identical, at least 98.5% identical, at least 98.6% identical, at least 98.7% identical, at least 98.8% identical, at least 98.9% identical, at least 99% identical, at least 99.1% identical, at least 99.2% identical, at least 99.3% identical, at least 99.4% identical, at least 99.5% identical, at least 99.6% identical, at least 99.7% identical, at least 99.8% identical, at least 99.9% identical, or 100% identical, to the sequence SEQ ID NO: 2.

Preferably, β-type *C. acnes* bacteria are *C. acnes* bacteria
(i) which comprise at least 90%, in particular at least 90.5%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.5%, at least 99%, at least 99.5% or 100% of the beta nucleotide variants as defined in Table 1, or which comprise at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217 or all of the beta nucleotide variants as defined in Table 1, and
(ii) in which the nucleic acid sequence of the hem locus is at least 97% identical, in particular at least 97.1% identical, at least 97.2% identical, at least 97.3% identical, at least 97.4% identical, at least 97.5% identical, at least 97.6% identical, at least 97.7% identical, at least 97.8% identical, at least 97.9% identical, at least 98% identical, at least 98.1% identical, at least 98.2% identical, at least 98.3% identical, at least 98.4% identical, at least 98.5% identical, at least 98.6% identical, at least 98.7% identical, at least 98.8% identical, at least 98.9% identical, at least 99% identical, at least 99.1% identical, at least 99.2% identical, at least 99.3% identical, at least 99.4% identical, at least 99.5% identical, at least 99.6% identical, at least 99.7% identical, at least 99.8% identical, at least 99.9% identical, or 100% identical, to the sequence SEQ ID NO: 2.

As used herein, "percent identity" between two sequences, means the percentage of identical nucleotides or amino acids between the two sequences to be compared, obtained with the best alignment of said sequences. As used herein, "best alignment" or "optimal alignment", means the alignment for which the determined percentage of identity (see below) is the highest. Sequence comparison between two sequences is usually realized by comparing these sequences that have been previously aligned according to the best alignment; this comparison is realized on segments of comparison in order to identify and compare the local regions of similarity. The best sequence alignment to perform comparison can be realized, besides manually, by using the global homology algorithm developed by Smith and Waterman (Smith and Waterman (1981) Ad. App. Math. 2:482), by using the local homology algorithm developed by Needleman and Wunsch (Needleman and Wunsch (1970) J. Mol. Biol 48:443), by using the method of similarities developed by Pearson and Lipman (Pearson and Lipman (1988) Proc. Natl Acd. Sci. USA 85:2444), by using computer software using such algorithms (GAP, BESTFIT, BLAST P, BLAST N, FASTA, TFASTA, etc.,), by using the MUSCLE multiple alignment algorithms (Edgar (2004) Nucleic Acids Research 32:1792). To get the best local alignment, one can preferably use Needleman-Wunsch algorithm. The identity percentage between two sequences is determined by comparing these two sequences optimally aligned, the sequences being able to comprise additions or deletions in respect to the reference sequence in order to get the optimal alignment between these two sequences. The percentage of identity may be calculated by determining the number of identical positions between these two sequences, and dividing this number by the total number of compared positions, and by multiplying the result obtained by 100 to get the percentage of identity between these two sequences. Preferably, for purposes herein, percent identity values refers to values generated using the pairwise sequence alignment program EMBOSS Needle that creates an optimal global alignment of two sequences using the Needleman-Wunsch algorithm, wherein all search parameters are set to default values, i.e. Scoring matrix=BLOSUM62 for protein sequences and DNAfull for DNA sequences, Gap open=10, Gap extend=0.5, End gap penalty=false, End gap open=10 and End gap extend=0.5.

Method of Treatment or Prevention of *C. acnes* Bacteria-Associated Disease

The present invention concerns a method for treating or preventing a *Cutibacterium acnes* bacteria-associated disease in a subject, said method comprising modulating, in said subject, the ratio of the amount of α-type *C. acnes* bacteria to the amount of β-type *C. acnes* bacteria,
wherein
α-type *C. acnes* bacteria are as defined in the section "α-type *C. acnes* bacteria and β-type *C. acnes* bacteria" above, and
β-type *C. acnes* bacteria are as defined in the section "α-type *C. acnes* bacteria and β-type *C. acnes* bacteria" above.

The present invention also concerns a composition for use in the treatment or prevention of a *C. acnes* bacteria-associated disease in a subject, said composition comprising a therapeutic or prophylactic agent inducing the modulation, in said subject, of the ratio of the amount of α-type *C. acnes* bacteria to the amount of β-type *C. acnes* bacteria,
wherein
α-type *C. acnes* bacteria are as defined in the section "α-type *C. acnes* bacteria and β-type *C. acnes* bacteria" above, and
β-type *C. acnes* bacteria are as defined in the section "α-type *C. acnes* bacteria and β-type *C. acnes* bacteria" above.

The present invention further concerns the use of a therapeutic or prophylactic agent inducing the modulation of the ratio of the amount of α-type *C. acnes* bacteria to the amount of β-type *C. acnes* bacteria, for the manufacture of a medicament for the treatment or prevention of a *C. acnes* bacteria-associated disease,
wherein
α-type *C. acnes* bacteria are as defined in the section "α-type *C. acnes* bacteria and β-type *C. acnes* bacteria" above, and
β-type *C. acnes* bacteria are as defined in the section "α-type *C. acnes* bacteria and β-type *C. acnes* bacteria" above.

By "*C. acnes* bacteria-associated disease" is meant herein a disease, in particular a skin disease, which is caused by *C. acnes* bacteria, or is associated with *C. acnes* bacteria presence, or in which *C. acnes* bacteria play a negative role.

Examples of *C. acnes* bacteria-associated disease include, but are not limited to, acne (such as acne vulgaris, acne inversa, acne conglobata, or acne fulminans), keratitis, synovitis acne pustulosis hyperostosis osteitis (SAPHO) syndrome, endocarditis, medical implant biofilm infection, prosthetic joint infections, surgical wound infections, vascular graft infections, anaerobic arthritis, cardiovascular device-related infections (such as prosthetic valve endocarditis), ocular implant infections, breast implant illness, sciatica, conjunctivitis, shunt-associated and/or spinal hardware central nervous system infections, shunt-associated central nervous system infections, sarcoidosis, endophthalmitis, osteomyelitis, allergic alveolitis, rheumatoid arthritis, infectious arthritis, chronic juvenile arthritis, chronic destructive oligoarthritis, degenerative disc disease, dental infections, ulcerative colitis hyperpyrexia, cerebral abscess, subdural empyema, peritonitis, periodontitis, endodontic infections, chronic rhinosinusitis, folliculitis, corneal ulcer, prostate inflammation, chronic prostatitis, primary biliary cirrhosis, hidradenitis suppurativa, pulmonary angiitis, atherosclerosis, prostatic cancer, progressive macular hypomelanosis, eczema, psoriasis, seborrheic dermatitis, rosacea, lichen sclerosus, lichen planus, prurigo nodularis and lichen simplex chronicus.

In a particular embodiment, said *C. acnes* bacteria-associated disease is a *C. acnes* bacteria-associated skin disease. Examples of *C. acnes* bacteria-associated skin diseases include, but are not limited to, acne (such as acne vulgaris, acne inversa, acne conglobata or acne fulminans), surgical skin wound infections, folliculitis, eczema, psoriasis, seborrheic dermatitis, rosacea, lichen sclerosus, lichen planus, prurigo nodularis and lichen simplex chronicus.

In a particular embodiment, said *C. acnes* bacteria-associated disease is a *C. acnes* bacteria-associated inflammatory disease. Examples of *C. acnes* bacteria-associated inflammatory diseases are well-known from the skilled person, and include without limitation acne (such as acne vulgaris, acne inversa, acne conglobata, or acne fulminans), sarcoidosis, SAPHO syndrome, eczema, psoriasis, seborrheic dermatitis, rosacea, lichen sclerosus, lichen planus, prurigo nodularis and lichen simplex chronicus.

Therefore, in a preferred embodiment, said *C. acnes* bacteria-associated disease is selected from the group consisting of acne (such as acne vulgaris, acne inversa, acne conglobata, or acne fulminans), sarcoidosis, SAP HO syndrome, eczema, psoriasis, seborrheic dermatitis, rosacea, lichen sclerosus, lichen planus, prurigo nodularis and lichen simplex chronicus.

In a more preferred embodiment, said *C. acnes* bacteria-associated disease is acne, more particularly acne vulgaris.

As used in the context of the invention, acne vulgaris is a chronic, inflammatory disorder of the pilosebaceous gland. It affects almost all humans at some point of their lives with 15 to 20% suffering from moderate to severe forms of acne. Acne may be classified as mild, moderate or severe. Mild acne typically corresponds to cases wherein there are less than 20 comedones and/or less than 15 inflammatory lesions and/or a total lesion count strictly inferior to 30. Moderate acne typically corresponds to cases wherein there are between 20 and 100 comedones and/or between 15 and 50 inflammatory lesions and/or a total lesion count between 30 and 125. Severe acne typically corresponds to cases wherein there are more than 5 pseudocysts and/or more than 100 comedones and/or more than 50 inflammatory lesions.

In a particular embodiment, said *C. acnes* bacteria-associated disease is severe acne.

As used herein, the terms "treatment", "treating," and the like, refer to obtaining a desired pharmacologic or physiologic effect. The effect may be therapeutic in terms of a partial or complete cure of a disease or disorder, or a symptom of a disease or disorder, or an adverse effect attributable to a disease or disorder. "Treatment" as used herein, includes inhibiting the disease, disorder or condition, i.e., arresting its development; and relieving the disease, disorder or condition i.e., causing regression of the disease, disorder or condition.

When applied to acne, the term "treatment" for example includes the reduction of the number of acne lesions, sebum excretion, follicular keratinization, come done formation, bacterial colonization of the follicle, *C. acnes* proliferation and/or inflammation. It further encompasses for example the decrease of the severity of the disease, such as the decrease of severe acne to moderate or mild acne, or the decrease of moderate acne to mild acne.

As used herein, the term "prevention", "preventing", and the like, includes preventing or decreasing the likelihood or severity of the onset of a disease. This includes prophylactic treatment of those having an enhanced risk of developing such disease. An elevated risk represents an above-average risk that a subject would develop a disease, which can be determined, for example, through family history, detection of genes causing a predisposition to developing said disease, or treatment with antibiotics.

When applied to acne, the term "prevention" for example encompasses the fact of avoiding reaching a given state of severity of acne, for example avoiding reaching severe acne, or moderate acne, or mild acne.

In a particular embodiment of the invention, the treatment and/or prevention of the *C. acnes* bacteria-associated disease is obtained by modulating the ratio of the amount of α-type *C. acnes* bacteria, as defined in the section "α-type *C. acnes* bacteria and β-type *C. acnes* bacteria" above, to the amount of β-type *C. acnes* bacteria, as defined in the section "α-type *C. acnes* bacteria and β-type *C. acnes* bacteria" above.

By "amount" is meant herein a relative (for example with respect to the whole bacterial population, in particular skin bacterial population, of the subject, or with respect to the whole *C. acnes* population, in particular skin *C. acnes* population, of the subject) or absolute amount (or concentration), that can be determined by any suitable technique well-known from the skilled person. Examples of techniques suitable to determine the amount of a given bacterial type(s) include direct cell counting, indirect cell counting, P C R (including real-time and quantitative PCR), and shotgun metagenomic sequencing.

By "modulating of the ratio" is meant herein an increase or reduction of the ratio after the implementation of the method and/or after the administration of the therapeutic or prophylactic agent compared to the ratio in the absence of or before the implementation of the method and/or the administration of the therapeutic or prophylactic agent.

In a particular embodiment, the modulation of the ratio is a statistically significant modulation.

In preferred embodiments, the treatment and/or prevention of the *C. acnes* bacteria-associated disease, in particular of the *C. acnes* bacteria-associated inflammatory disease, is obtained by reducing the ratio of the amount of α-type *C. acnes* bacteria, as defined in the section "α-type *C. acnes* bacteria and β-type *C. acnes* bacteria" above, to the amount of β-type *C. acnes* bacteria, as defined in the section "α-type *C. acnes* bacteria and β-type *C. acnes* bacteria" above.

By "reduction of the ratio" is meant herein a reduction of the ratio after the implementation of the method and/or after the administration of the therapeutic or prophylactic agent compared to the ratio in the absence of or before the implementation of the method and/or the administration of the therapeutic or prophylactic agent.

Preferably, the reduction of the ratio is a statistically significant reduction.

In a particular embodiment, said modulation, preferably reduction, of the ratio is observed 1 day after the first implementation of the method and/or after the first administration of the therapeutic or prophylactic agent, in particular 2 days, 3 days, 4 days, 5 days, 6 days, 7 days, 2 weeks, 3 weeks, 1 month, 2 months, 3 months, 4 months, 5 months, 6 months or 1 year after the first implementation of the method and/or after the first administration of the therapeutic or prophylactic agent.

In a particular embodiment, said modulation, preferably reduction, of the ratio is maintained (not necessarily at the same level) for 1 day after the first implementation of the method and/or after the first administration of the therapeutic or prophylactic agent, in particular 2 days, 3 days, 4 days, 5 days, 6 days, 7 days, 2 weeks, 3 weeks, 1 month, 2 months, 3 months, 4 months, 5 months, 6 months or 1 year after the first implementation of the method and/or after the first administration of the therapeutic or prophylactic agent.

In a particular embodiment, said modulation, preferably reduction, of the ratio is maintained (not necessarily at the same level) for the whole period during which the method is implemented and/or the therapeutic or prophylactic agent is administered.

Preferably, said ratio is the ratio of the amount of α-type *C. acnes* bacteria, as defined in the section "α-type *C. acnes* bacteria and β-type *C. acnes* bacteria" above, on the skin of said subject to the amount of β-type *C. acnes* bacteria, as defined in the section "α-type *C. acnes* bacteria and β-type *C. acnes* bacteria" above, on said skin.

According to the present invention, the skin refers to the skin of the arms, especially the hands, the skin of the legs, especially the feet, the skin of the armpits, the skin of the neck, the skin of the chest, the skin of the back, the skin of the scalp, and/or the skin of the face. In a preferred embodiment, the skin is the skin of the face, of the neck, of the chest and/or of the back. In a still preferred embodiment, the skin is the skin of the face.

Specifically Reducing the Amount of α-Type *C. acnes* Bacteria

In a particular embodiment, the treating or preventing method of the invention comprises specifically reducing the amount of α-type *C. acnes* bacteria, as defined in the section "α-type *C. acnes* bacteria and β-type *C. acnes* bacteria" above, in the subject, in particular on the skin of the subject.

The present invention therefore concerns a method for treating or preventing a *C. acnes* bacteria-associated disease in a subject, said method comprising specifically reducing the amount of α-type *C. acnes* bacteria in said subject, wherein α-type *C. acnes* bacteria are as defined in the section "α-type *C. acnes* bacteria and β-type *C. acnes* bacteria" above. It also concerns a composition for use in the treatment or prevention of a *C. acnes* bacteria-associated disease in a subject, said composition comprising a therapeutic or prophylactic agent which specifically reduces the amount of α-type *C. acnes* bacteria in said subject, wherein α-type *C. acnes* bacteria are as defined in the section "α-type *C. acnes* bacteria and β-type *C. acnes* bacteria" above. It further concerns the use of a therapeutic or prophylactic agent which specifically reduces the amount of α-type *C. acnes* bacteria in a subject for the manufacture of a medicament for the treatment or prevention of a *C. acnes* bacteria-associated disease, wherein α-type *C. acnes* bacteria are as defined in the section "α-type *C. acnes* bacteria and β-type *C. acnes* bacteria" above.

As used herein, the term "amount" has the same meaning as disclosed in the section "Method of treatment or prevention of *C. acnes* bacteria-associated disease" above.

By "specifically reducing the amount of α-type *C. acnes* bacteria" is meant herein that the amount, in said subject, in particular on the skin of said subject, of *C. acnes* bacteria of another type than α-type, in particular of β-type *C. acnes* bacteria, is not significantly reduced, and/or the amount, in said subject, in particular on the skin of said subject, of other bacterial species is not significantly reduced. Preferably, by "specifically reducing the amount of α-type *C. acnes* bacteria" is meant herein that the amount, in said subject, in particular on the skin of said subject, of *C. acnes* bacteria of another type than α-type, in particular of β-type *C. acnes* bacteria, is not significantly reduced.

By "reduction of the amount" is meant herein a reduction of the amount after the implementation of the method and/or after the administration of the therapeutic or prophylactic agent compared to the amount in the absence of or before the implementation of the method and/or the administration of the therapeutic or prophylactic agent.

Preferably, the reduction of the amount is a statistically significant reduction.

In a particular embodiment, said reduction of the amount is observed 1 day after the first implementation of the method and/or after the first administration of the therapeutic or prophylactic agent, in particular 2 days, 3 days, 4 days, 5 days, 6 days, 7 days, 2 weeks, 3 weeks, or 1 month after the first implementation of the method and/or after the first administration of the therapeutic or prophylactic agent.

In a particular embodiment, said reduction of the amount is maintained (not necessarily at the same level) for 1 day after the first implementation of the method and/or after the first administration of the therapeutic or prophylactic agent, in particular 2 days, 3 days, 4 days, 5 days, 6 days, 7 days, 2 weeks, 3 weeks, 1 month, 2 months, 3 months, 4 months, 5 months, 6 months or 1 year after the first implementation of the method and/or after the first administration of the therapeutic or prophylactic agent.

In a particular embodiment, said reduction of the amount is maintained (not necessarily at the same level) for the whole period during which the method is implemented and/or the therapeutic or prophylactic agent is administered.

In a particular embodiment, the treating or preventing method of the invention comprises specifically killing or inhibiting the growth of α-type *C. acnes* bacteria, as defined in the section "α-type *C. acnes* bacteria and β-type *C. acnes* bacteria" above, in the subject, in particular on the skin of the subject.

The present invention therefore concerns a method for treating or preventing a *C. acnes* bacteria-associated disease in a subject, said method comprising specifically killing or inhibiting the growth of α-type *C. acnes* bacteria in said subject, wherein α-type *C. acnes* bacteria are as defined in the section "α-type *C. acnes* bacteria and β-type *C. acnes* bacteria" above. It also concerns a composition for use in the treatment or prevention of a *C. acnes* bacteria-associated disease in a subject, said composition comprising a therapeutic or prophylactic agent which specifically kills or inhibits the growth of α-type *C. acnes* bacteria in said subject, wherein α-type *C. acnes* bacteria are as defined in the section "α-type *C. acnes* bacteria and β-type *C. acnes* bacteria" above. It further concerns the use of a therapeutic or prophylactic agent which specifically kills or inhibits the growth of α-type *C. acnes* bacteria for the manufacture of a medicament for the treatment or prevention of a *C. acnes* bacteria-associated disease, wherein α-type *C. acnes* bacteria are as defined in the section "α-type *C. acnes* bacteria and β-type *C. acnes* bacteria" above.

In a particular embodiment, said α-type *C. acnes* bacteria are killed at a level corresponding to a reduction of at least 20%, at least 30%, at least 40%, at least 50%, at least 60%, at least 70%, at least 80% or at least 90%, preferably a reduction of at least 50%, at least 60%, at least 70%, at least 80% or at least 90%, of the α-type *C. acnes* bacteria population, in particular α-type *C. acnes* bacteria skin population, in the subject, compared to a non-treated population or compared to the α-type *C. acnes* bacteria population, in particular α-type *C. acnes* bacteria skin population, in the subject before the implementation of the method and/or the administration of the therapeutic or prophylactic agent.

In a preferred embodiment, said α-type *C. acnes* bacteria are killed at a level corresponding to an at least 0.1 log, at least 0.2 log, at least 0.5 log, at least 1 log, preferably at least 2 log, more preferably at least 3 log, at least 4 log or at least 5 log reduction of the α-type *C. acnes* bacteria population, in particular α-type *C. acnes* bacteria skin population, in the subject, compared to a non-treated population or compared to the α-type *C. acnes* bacteria population, in particular α-type *C. acnes* bacteria skin population, in the subject before the implementation of the method and/or the administration of the therapeutic or prophylactic agent.

As used herein, the term "log" refers to the common logarithm which is the base-10 logarithm (also indicated by $\log_{10}$).

By "specifically killing α-type *C. acnes* bacteria" is meant herein that *C. acnes* bacteria of another type than α-type, in particular β-type *C. acnes* bacteria, and/or other bacterial species, present in said subject, in particular on the skin of said subject, are not significantly killed, in particular are killed at a level at least 1 log, at least 2 log, at least 3 log or at least 4 log inferior to α-type *C. acnes* bacteria. Preferably, by "specifically killing α-type *C. acnes* bacteria" is meant herein that *C. acnes* bacteria of another type than α-type, in particular β-type *C. acnes* bacteria, present in said subject, in particular on the skin of said subject, are not significantly killed, in particular are killed at a level at least 1 log, at least 2 log, at least 3 log or at least 4 log inferior to α-type *C. acnes* bacteria. In some particular embodiments, by "specifically killing α-type *C. acnes* bacteria" is meant herein that *C. acnes* bacteria of another type than α-type, in particular β-type *C. acnes* bacteria, and/or other bacterial species, preferably β-type *C. acnes* bacteria, present in said subject, in particular on the skin of said subject, are killed at a level corresponding to a reduction of less than 20%, preferably less than 10%, of the population of *C. acnes* bacteria of another type than α-type, in particular β-type *C. acnes* bacteria, and/or other bacterial species, preferably β-type *C. acnes* bacteria, in the subject, compared to a non-treated population or compared to the population of *C. acnes* bacteria of another type than α-type, in particular β-type *C. acnes* bacteria, and/or other bacterial species, preferably β-type *C. acnes* bacteria, in the subject, preferably in the skin of the subject, before the implementation of the method and/or the administration of the therapeutic or prophylactic agent.

In a particular embodiment, the growth of said α-type *C. acnes* bacteria is inhibited at a level corresponding to an at least 20%, at least 30%, at least 40%, at least 50%, at least 60%, at least 70%, at least 80% or at least 90%, preferably an at least 50%, at least 60%, at least 70%, at least 80% or at least 90%, reduction of the α-type *C. acnes* bacteria population, in particular α-type *C. acnes* bacteria skin population, in the subject, compared to a non-treated population or compared to the α-type *C. acnes* bacteria population, in particular α-type *C. acnes* bacteria skin population, in the subject before the implementation of the method and/or the administration of the therapeutic or prophylactic agent.

In a preferred embodiment, the growth of said α-type *C. acnes* bacteria is inhibited at a level corresponding to an at least 0.1 log, at least 0.2 log, at least 0.5 log, at least 1 log, preferably at least 2 log, more preferably at least 3 log, at least 4 log or at least 5 log reduction of the α-type *C. acnes* bacteria population, in particular α-type *C. acnes* bacteria skin population, in the subject, compared to a non-treated population or compared to the α-type *C. acnes* bacteria population, in particular α-type *C. acnes* bacteria skin population, in the subject before the implementation of the method and/or the administration of the therapeutic or prophylactic agent.

By "specifically inhibiting the growth of α-type *C. acnes* bacteria" is meant herein that the growth of *C. acnes* bacteria of another type than α-type, in particular β-type *C. acnes* bacteria, and/or other bacterial species, present in said subject, in particular on the skin of said subject, is not significantly inhibited, in particular is inhibited at a level at least 1 log, at least 2 log, at least 3 log or at least 4 log inferior to α-type *C. acnes* bacteria. Preferably, by "specifically inhibiting the growth of α-type *C. acnes* bacteria" is meant herein that the growth of *C. acnes* bacteria of another type than α-type, in particular β-type *C. acnes* bacteria, present in said subject, in particular on the skin of said subject, is not significantly inhibited, in particular is inhibited at a level at least 1 log, at least 2 log, at least 3 log or at least 4 log inferior to α-type *C. acnes* bacteria. In some particular embodiments, by "specifically inhibiting the growth of α-type *C. acnes* bacteria" is meant herein that the growth of *C. acnes* bacteria of another type than α-type, in particular β-type *C. acnes* bacteria, and/or other bacterial species, preferably β-type *C. acnes* bacteria, present in said subject, in particular on the skin of said subject, is inhibited at a level corresponding to a reduction of less than 20%, preferably less than 10%, compared to a non-treated population or compared to the population of *C. acnes* bacteria of another type than α-type, in particular β-type *C. acnes* bacteria, and/or other bacterial species, preferably β-type *C. acnes* bacteria, in the subject, preferably in the skin of the subject, before the implementation of the method and/or the administration of the therapeutic or prophylactic agent.

In a particular embodiment, the treating or preventing method of the invention comprises administering to said subject a therapeutically or prophylactically effective amount of an antibacterial, phage, recombinant phage, packaged phagemid, plasmid, DNA- or RNA-containing vesicle, extracellular vesicle, bacteria or engineered bacteria, which specifically targets said α-type *C. acnes* bacteria, as defined in the section "α-type *C. acnes* bacteria and β-type *C. acnes* bacteria" above.

Similarly, in a particular embodiment of the composition for use according to the present invention or the use of a therapeutic or prophylactic agent according to the present invention, the therapeutic or prophylactic agent is an antibacterial, phage, recombinant phage, packaged phagemid, plasmid, DNA- or RNA-containing vesicle, extracellular vesicle, bacteria or engineered bacteria, which specifically targets said α-type *C. acnes* bacteria, as defined in the section "α-type *C. acnes* bacteria and β-type *C. acnes* bacteria" above.

As used herein, the term "therapeutically effective amount" refers to a nontoxic but sufficient amount of an active agent to provide the desired therapeutic effect.

As used herein, the term "prophylactically effective amount" refers to a nontoxic but sufficient amount of an active agent to provide the desired preventive effect.

By "targets said α-type *C. acnes* bacteria" is meant herein that said therapeutic or prophylactic agent is able to recognize, preferably specifically recognizes, said α-type *C. acnes* bacteria, and/or to exert, preferably specifically exert, its activity on said α-type *C. acnes* bacteria.

By "specifically targets said α-type *C. acnes* bacteria" is meant herein that said therapeutic or prophylactic agent recognizes and/or exerts its activity on said α-type *C. acnes* bacteria but does not significantly recognize and/or exert its activity on *C. acnes* bacteria of another type than α-type, in particular β-type *C. acnes* bacteria, and/or other bacterial species, present in said subject, in particular on the skin of said subject. Preferably, by "specifically targets said α-type *C. acnes* bacteria" is meant herein that said therapeutic or prophylactic agent recognizes and/or exerts its activity on said α-type *C. acnes* bacteria but does not significantly recognize and/or exert its activity on *C. acnes* bacteria of another type than α-type, in particular β-type *C. acnes* bacteria, present in said subject, in particular on the skin of said subject.

By "antibacterial" is meant herein a compound inhibiting or preventing bacterial growth, killing bacteria, or reducing the number of bacteria. Said antibacterial can typically be a small molecule, a protein, peptide or polypeptide, or a nucleic acid such as a DNA or RNA. Examples of antibacterials include antibiotics, bacteriocins and endolysins. Therefore, in a particular embodiment, said antibacterial is an antibiotic, a bacteriocin and/or an endolysin, which specifically targets said α-type *C. acnes* bacteria, as defined in the section "α-type *C. acnes* bacteria and β-type *C. acnes* bacteria" above.

By "bacteriocin" is meant herein a proteinaceous toxin produced by bacteria to kill or inhibit growth of other bacteria. Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In the context of the invention, said bacteriocin may be a wild-type bacteriocin or an engineered bacteriocin, in particular a bacteriocin mutant, variantor chimera, typically comprising modifications and/or alterations of the amino acid sequence. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, thiol- or carboxyl-groups. Such modified bacteriocin typically exhibits the lytic activity of the wild-type bacteriocin. However, said activity can be the same, higher or lower than the activity of the wild-type bacteriocin. Said activity can be about 10, 20, 30, 40, 50, 60, 70, 80, 90, 100, 110, 120, 130, 140, 150, 160, 170, 180, 190 or about 200% of the activity of the wild-type bacteriocin or even more. The activity can be measured by assays well known in the art by a person skilled in the art as e.g. the plate lysis assay or the liquid lysis assay which are e.g. described in Briers et al. (2007) *j. Biochem. Biophys Methods* 70:531-533, or Donovan et al. (2006) *FEMS Microbiol Lett.* 265:133-139. Alternatively, such modified bacteriocin can exhibit a different lytic activity compared to the wild-type bacteriocin, such as a lytic activity with a different specificity compared to the wild-type bacteriocin.

By "endolysin" or "lysin" is meant herein enzymes used by bacteriophages at the end of their replication cycle to degrade the peptidoglycan of the bacterial host from within, resulting in cell lysis and release of progeny virions. They are typically either β(1,4)-glycosylases (lysozymes), transglycosylases, amidases or endopeptidases.

In the context of the invention, said endolysin may be a wild-type endolysin or an engineered endolysin, in particular a endolysin mutant, variant or chimera, typically comprising modifications and/or alterations of the amino acid sequence. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Such modified endolysin typically exhibit the lytic activity of the wild-type endolysin. However, said activity can be the same, higher or lower than the activity of the wild-type endolysin. Said activity can be about 10, 20, 30, 40, 50, 60, 70, 80, 90, 100, 110, 120, 130, 140, 150, 160, 170, 180, 190 or about 200% of the activity of the wild-type endolysin or even more. The activity can be measured by assays well known in the art by a person skilled in the art as e.g. the plate lysis assay or the liquid lysis assay which are e.g. described in Briers et al. (2007) *J. Biochem. Biophys Methods* 70:531-533, or Donovan et al. (2006) *FEMS Microbiol Lett.* 265:133-139. Alternatively, such modified endolysin can exhibit a different lytic activity compared to the wild-type endolysin, such as a lytic activity with a different specificity compared to the wild-type endolysin.

By "phage" or "bacteriophage" is meant herein a bacterial virus. Bacteriophages are obligate intracellular parasites that multiply inside bacteria by co-opting some or all of the host biosynthetic machinery. Bacteriophages can be found inside bacteria as a prophage whose genome is integrated in the bacterial chromosome or as a phage-plasmid whose genome is part of an extrachromosomal plasmid (such phage-plasmids are for example disclosed in Ravin et al. (1999) *Molecular Microbiology* 34(5):980-994). Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

In the context of the invention, the terms "recombinant" and "engineered" are used interchangeably. By "recombinant" is meant herein a nucleic acid, protein or microorganism containing genetic materials derived from multiple different sources and/or obtained using molecular biology and/or synthetic biology tools, or being encoded by genetic materials derived from multiple different sources and/or obtained using molecular biology and/or synthetic biology tools. Therefore, in the context of the invention, a "recombinant" nucleic acid, protein or microorganism is not a wild-type nucleic acid, protein or microorganism.

As used herein, a "recombinant phage" refers to a phage, as defined above, that has been modified at the protein and/or nucleic acid level. Therefore, in the context of the invention a "recombinant phage" is not a wild-type phage or a phage obtained after natural evolution, but a phage which has been voluntarily modified, for example using molecular biology and/or synthetic biology tools.

As used herein, the term "phagemid" or "phasmid" are equivalent and refer to a vector that derives from both a plasmid and a bacteriophage genome. A phagemid typically comprises a phage packaging site and optionally an origin of replication (ori), in particular a bacterial and/or phage origin of replication. In one embodiment, the phagemid does not comprise a functional bacterial origin of replication and thus cannot replicate by itself once injected into a bacterium. Alternatively, the phagemid can comprise a plasmid origin of replication, in particular a bacterial and/or phage origin of replication.

As used herein, the term "packaged phagemid" refers to a phagemid which is encapsidated in a bacteriophage scaffold, phage-derived delivery particle or capsid. Particularly, it refers to a bacteriophage scaffold, phage delivery particle or capsid devoid of a bacteriophage genome. The packaged phagemid may be produced with a helper phage strategy, well known from the man skilled in the art. The helper phage typically comprises all the genes coding for the structural and functional proteins that are indispensable for the phagemid according to the invention to be encapsidated.

As used herein, the term "plasmid" refers to a circular nucleic acid molecule capable of autonomous replication in a host cell. Said plasmid can be a conjugative plasmid. In a particular embodiment, said plasmid is a recombinant plasmid.

As used herein, the term "DNA- or RNA-containing vesicle" refers to an artificial delivery vehicle enclosing at least one nucleic acid molecule (which can be DNA, RNA or a mixture thereof) within a core surrounded by a shell. Said DNA- or RNA-containing vesicle can be chemically-based vesicles, in particular polymer-based vesicles such as polymersomes or nonionic surfactants such as niosomes, lipid-based vesicles such as liposomes, protein-based or peptide-based vesicles, or nanoparticle-based vesicles.

As used herein, the term "extracellular vesicle" or "cell-derived nanovesicle" refers to a nanosized structure in the form of a particle, released or secreted from cells, which enclose biomolecules, such as proteins, nucleic acid molecules, lipids or organelles, in a cell membrane of a lipid layer, typically identical to the cell membrane of the cell from which the biomolecules are derived. Examples of extracellular vesicles include microvesicles, exosomes, oncosomes and apoptotic bodies. Extracellular vesicles typically have an average diameter of 30 nm to 1 μm, preferably of 100 nm to 1 μm. Extracellular vesicles can be isolated from naturally formed extracellular vesicles (for example by differential centrifugation culminating in ultrafiltration, density gradient/cushion centrifugation, and immunoaffinity-based capture) or can be obtained by artificial methods (for example by an extrusion process where cells are passed through microfluidic channels, a multi-stage filtration process, etc.).

The bacteria used in the context of the invention can be a wild-type bacteria, such as a wild-type bacteria naturally able to specifically target α-type *C. acnes* bacteria, as defined in the section "α-type *C. acnes* bacteria and β-type *C. acnes* bacteria" above, for example by naturally producing antibacterials, as defined above, that specifically target α-type *C. acnes* bacteria, or phages, as defined above, that specifically target α-type *C. acnes* bacteria. Alternatively, the bacteria used in the context of the invention are engineered (also called recombinant bacteria), for example bacteria which have been engineered to produce antibacterials as defined above, that specifically target α-type *C. acnes* bacteria, or to produce phages or engineered phages, as defined above, that specifically target α-type *C. acnes* bacteria, or to comprise phagemids or plasmids, as defined above, that specifically target α-type *C. acnes* bacteria.

As used herein, "engineered bacteria" refers to bacteria that have been modified at the protein and/or nucleic acid level. Therefore, in the context of the invention "engineered bacteria" are not a wild-type bacteria or bacteria obtained after natural evolution, but bacteria which have been voluntarily modified, for example using molecular biology and/or synthetic biology tools.

In a particular embodiment, the treating or preventing method of the invention comprises administering to said subject a therapeutically or prophylactically effective amount of a phage, recombinant phage, packaged phagemid, plasmid, DNA- or RNA-containing vesicle, extracellular vesicle, bacteria or engineered bacteria, as defined above, which specifically targets said α-type *C. acnes* bacteria, as defined in the section "α-type *C. acnes* bacteria and β-type *C. acnes* bacteria" above.

Similarly, in a particular embodiment of the composition for use according to the present invention or the use of a therapeutic or prophylactic agent according to the present invention, the therapeutic or prophylactic agent is a phage, recombinant phage, packaged phagemid, plasmid, DNA- or RNA-containing vesicle, extracellular vesicle, bacteria or engineered bacteria, as defined above, which specifically targets said α-type *C. acnes* bacteria, as defined in the section "α-type *C. acnes* bacteria and β-type *C. acnes* bacteria" above.

In a preferred embodiment, the phage, recombinant phage, packaged phagemid, plasmid, DNA- or RNA-containing vesicle, extracellular vesicle, bacteria or engineered bacteria, encodes (or comprises a nucleic acid which encodes) a programmable nuclease designed to specifically target said α-type *C. acnes* bacteria.

By "programmable nuclease" is meant herein an enzyme designed to recognize and cleave a particular nucleic acid sequence. Programmable nucleases are well-known from the skilled person and include C R IS P R-Cas systems (including C R IS P R-Cas nucleases), TALE Ns and variants thereof, zinc finger nucleases (ZFN) and variants thereof, natural, evolved or engineered meganuclease or recombinase variants, and any combination and hybrid thereof.

Therefore, in a particular embodiment, said programmable nuclease is selected from CRISPR-Cas nucleases, TALENs and variants thereof, ZFNs and variants thereof, natural, evolved or engineered meganuclease or recombinase variants, and any combination and hybrid thereof.

As used herein, the term "TALEN" or "transcription activator-like effector nuclease" refers to a recombinant protein comprising a "Transcription Activator-like effector (TALE) binding domain" and an endonuclease domain. "Transcription Activator-Like effector (TALE) binding domain" refers to a protein that contains a "repeat region" (also referred to as "repeat domain"), which contains a plurality of repeated highly conserved 33-34 amino acid sequence (referred to as a "repetitive module" and "repeat module"), with the last repetitive module at the C-terminal end being a partial or half (approximately 20 amino acids) length. The combination of repetitive modules in the repeat region binds to a specific nucleotide sequence in the target DNA and/or RNA sequence, such that the TALE N modifies the target DNA and/or RNA within or adjacent to the specific nucleotide sequence in the cell or progeny thereof.

As used herein, the term "zinc finger nuclease" or "ZFN" refers to a chimeric protein comprising a zinc finger DNA-binding domain fused to a nuclease domain from an endonuclease or exonuclease.

As used herein, the term "meganuclease" refers to an endonuclease that binds double-stranded DNA at a recognition sequence that is greater than 12 base pairs. Naturally-occurring meganucleases can be monomeric (e.g., I-SceI) ordimeric (e.g., I-CreI). The term meganuclease, as used herein, can be used to refer to monomeric meganucleases, dimeric meganucleases, or to the monomers which associate to form a dimeric meganuclease. Due to the large recognition site of meganucleases, this site generally occurs only once in any given genome.

As used herein, the term "recombinase" refers to a DNA modifying enzyme that binds, cleaves, strand exchanges, and rejoins DNA at its respective recombination sites (i.e., an enzyme capable of performing DNA recombination).

"C R IS P R-Cas system" refers to Clustered regularly interspaced short palindromic repeats and their C R IS P R-associated (Cas) proteins. These systems comprise a plurality of diverse RNA guided prokaryotic adaptive immune systems employed by these organisms to defend against foreign parasitic nucleic acids.

The CRISP R-Cas system contains two distinct elements, i.e. i) an endonuclease, in this case the C R IS P R associated nuclease (Cas or "C R IS P R associated protein") and ii) a guide RNA.

Depending on the type of C RIS P R-Cas system, the guide RNA may be in the form of a chimeric RNA which consists of the combination of a C R IS P R (crRNA) bacterial RNA and a tracrRNA (trans-activating RNA C R IS P R) (J inek et al. (2012) Science 337(6096):816-21). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR-Cas system includes two main classes depending on the nuclease mechanism of action:
Class 1 is made of multi-subunit effector complexes and includes type 1, Ill and IV;
Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D).

In a particular embodiment, the programmable nuclease is a CRISP R-Cas nuclease (also referred to herein as Cas nuclease or CRISPR enzyme). A variety of CRISPR enzymes are available for use in the context of the present invention. In some embodiments, the C R IS P R enzyme is a Type II CRISPR enzyme, a Type II-A or Type II-B CRISPR enzyme. In another embodiment, the CRISPR enzyme is a Type I CRISPR enzyme or a Type Ill CRISPR enzyme. In some embodiments, the C RIS P R enzyme catalyzes DNA cleavage. In some other embodiments, the C R IS P R enzyme catalyzes RNA cleavage.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologues or orthologues thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA(s).

The sequence encoding Cas9 (the entire protein or a fragment thereof) as used in the context of the invention can be obtained from any known Cas9 protein (Fonfara et al. (2014) Nucleic Acids Res. 42(4):2577-90; Koonin et al. (2017) CurrOpin Microbiol. 37:67-78). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

In a particular embodiment, the C RIS P R enzyme is dCas9.

The sequence encoding Cpf1 (Cas12a) (the entire protein ora fragment thereof) as used in the context of the invention can be obtained from any known Cpf1 (Cas12a) protein (Koonin et al. (2017) Curr Opin Microbiol. 37:67-78). Examples of Cpf1(Cas12a) proteins useful in the present invention include, but are not limited to, Cpf1(Cas12a) proteins of *Acidaminococcus* sp, Lachnospiraceae bacteriu and *Francisella novicida*.

The sequence encoding Cas13a (the entire protein or a fragment thereof) as used in the context of the invention can be obtained from any known Cas13a (C2c2) protein (Abudayyeh et al. (2017) Nature 550(7675):280-284). Examples of Cas13a (C2c2) proteins useful in the present invention include, but are not limited to, Cas13a (C2c2) proteins of Leptotrichia wadei (LwaCas13a).

The sequence encoding Cas13d (the entire protein or a fragment thereof) as used in the context of the invention can be obtained from any known Cas13d protein (Yan et al. (2018) Mol Cell. 70(2):327-339.e5.). Examples of Cas13d proteins useful in the present invention include, but are not limited to, Cas13d proteins of *Eubacterium siraeum* and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In one embodiment, the C R IS P R enzymes may be coupled to a guide RNA or single guide RNA (sgRNA).

Therefore, in a preferred embodiment, said phage, recombinant phage, packaged phagemid, plasmid, DNA- or RNA-containing vesicle, extracellular vesicle, bacteria engineered bacteria, further encodes a guide RNA designed to specifically target said α-type *C. acnes* bacteria.

As used herein, the term "guide RNA" refers to either a crRNA (also known as CRISPR RNA), or the combination of a crRNA and a trRNA (also known as tracrRNA). The crRNA and trRNA may be associated as a single RNA molecule (single guide RNA, sgRNA) or in two separate RNA molecules (dual guide RNA, dgRNA). The trRNA may be a naturally-occurring sequence, or a trRNA sequence with modifications or variations compared to naturally occurring sequences. For clarity, the term "guide RNA" as used herein, and unless specifically stated otherwise, may refer to an RNA molecule (comprising A, C, G, and U nucleotides) or to a DNA molecule encoding such an RNA molecule (comprising A, C, G, and T nucleotides) or complementary sequences thereof. As well-known from the skilled person, a "guide RNA" in the CRISPR-Cas system is utilized for the detection of a target nucleic acid and is responsible for recognizing a portion of the sequence possessed by the target nucleic acid. A guide RNA contains a sequence for recognizing a portion of the sequence carried by the target nucleic acid and is responsible for the specificity of detection of the target nucleic acid in the CRISPR-Cas system. The guide RNA is typically designed to match the Cas protein with which it is administered. Methods for designing and producing a guide RNA are well known.

In a particular embodiment, said guide RNA is designed to specifically target an α-type *C. acnes* bacteria-specific sequence, gene or locus.

In a particular embodiment, said guide RNA is designed to specifically target the hem locus of said α-type *C. acnes* bacteria.

In a more preferred embodiment, said guide RNA is designed to specifically target at least one of the nucleotide variants in the hem locus associated with α-type *C. acnes* bacteria, as defined in the section "α-type *C. acnes* bacteria and β-type *C. acnes* bacteria" above. Preferably, said guides RNA are selected to have at least one mismatch, preferably two mismatches, between α-type *C. acnes* bacteria and β-type *C. acnes* bacteria and/or a mismatch in the PAM site.

Therefore, in a still more particular embodiment, said guide RNA is designed to specifically target at least one of the following nucleotide variants in the hem locus:

in the hemA gene: T173, A479, T506, A614, T629, C671, T971, A989, T1085, and T1094, wherein the positions are defined with reference to sequence SEQ ID NO: 3, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5, in the hemD gene: T11, T41, T50, A150, T155, G159, G176, T257, C266, T278, G323, A324, T362, T367, T374, G 387, A398, A399, T407, G422, G425, G432, A446, A459, T464, G595, T617, T643, A644, and C680, wherein the positions are defined with reference to sequence SEQ ID NO: 6, in the hemE gene: T241, T476, A530, T704, A728, G767, T834, A867, A872, A882, and A957, wherein the positions are defined with reference to sequence SEQ ID NO: 7, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8, in the hemL gene: T107, C197, T229, A242, C310, A338, A374, T389, G392, T442, C467, G470, C482, G518, and C641, wherein the positions are defined with reference to sequence SEQ ID NO: 9, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10.

Preferably, said phage, recombinant phage, packaged phagemid, plasmid, DNA- or RNA-containing vesicle, extracellular vesicle, bacteria or engineered bacteria, encodes a plurality (at least 2, 3, 4, 5 or more) guide RNAs specifically targeting a plurality (at least 2, 3, 4, 5 or more) of the nucleotide variants in the hem locus associated with α-type *C. acnes* bacteria, as defined in the section "α-type *C. acnes* bacteria and β-type *C. acnes* bacteria" above.

In a particular embodiment, said phage, recombinant phage, packaged phagemid, plasmid, DNA- or RNA-containing vesicle, extracellular vesicle, bacteria or engineered bacteria, comprises a sequence encoding a guide RNA selected from the group consisting of SEQ ID NOs: 13 to 16.

Genetically Modifying a DNA Sequence in the α-Type *C. acnes* Bacteria

In a particular embodiment, the treating or preventing method of the invention comprises genetically modifying a DNA sequence in the α-type *C. acnes* bacteria, as defined in the section "α-type *C. acnes* bacteria and β-type *C. acnes* bacteria" above, in said subject, in particular on the skin of said subject, to generate at least one change in said α-type *C. acnes* bacteria, preferably in the hem locus of said α-type *C. acnes* bacteria.

Similarly, in a particular embodiment of the composition for use according to the present invention or the use of a therapeutic or prophylactic agent according to the present invention, the therapeutic or prophylactic agent induces the genetic modification of a DNA sequence in the α-type *C. acnes* bacteria, as defined in the section "α-type *C. acnes* bacteria and β-type *C. acnes* bacteria" above, in said subject, in particular on the skin of said subject, to generate at least one change in said α-type *C. acnes* bacteria, preferably in the hem locus of said α-type *C. acnes* bacteria.

The present invention therefore concerns a method for treating or preventing a *C. acnes* bacteria-associated disease in a subject, said method comprising genetically modifying a DNA sequence in the α-type *C. acnes* bacteria in said subject, in particular on the skin of said subject, to generate at least one change in said α-type *C. acnes* bacteria, preferably in the hem locus of said α-type *C. acnes* bacteria. It also concerns a composition for use in the treatment or prevention of a *C. acnes* bacteria-associated disease in a subject, said composition comprising a therapeutic or prophylactic agent which genetically modifies a DNA sequence in the α-type *C. acnes* bacteria in said subject, in particular on the skin of said subject, to generate at least one change in said α-type *C. acnes* bacteria, preferably in the hem locus of said α-type *C. acnes* bacteria. It further concerns the use of a therapeutic or prophylactic agent which genetically modifies a DNA sequence in the α-type *C. acnes* bacteria in a subject, in particular on the skin of said subject, to generate at least one change in said α-type *C. acnes* bacteria, preferably in the hem locus of said α-type *C. acnes* bacteria, for the manufacture of a medicament for the treatment or prevention of a *C. acnes* bacteria-associated disease.

By "genetically modifying a DNA sequence" or "genetic modification of a DNA sequence" is meant herein that at least one nucleotide of a DNA sequence is modified. Said modification can be a substitution of at least one nucleotide, an insertion of at least one nucleotide, a deletion of at least one nucleotide, or a modification of the nucleobase of at least one nucleotide (such as methylation).

In the context of the invention, said genetic modification preferably occurs in the hem locus of said α-type *C. acnes* bacteria, in other words, said genetic modification preferably generates at least one change in the hem locus of said α-type *C. acnes* bacteria.

In a particular embodiment, said genetic modification preferably generates at least one change in at least one of the following nucleotide variants in the hem locus:
  in the hemA gene: T173, A479, T506, A614, T629, C671, T971, A989, T1085, and T1094, wherein the positions are defined with reference to sequence SEQ ID NO: 3,
  in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4,
  in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5,
  in the hemD gene: T11, T41, T50, A150, T155, G159, G176, T257, C266, T278, C323, A324, T362, T367, T374, G 387, A398, A399, T407, G422, G425, G432, A446, A459, T464, G595, T617, T643, A644, and C680, wherein the positions are defined with reference to sequence SEQ ID NO: 6,
  in the hemE gene: T241, T476, A530, T704, A728, G767, T834, A867, A872, A882, and A957, wherein the positions are defined with reference to sequence SEQ ID NO: 7,
  in the hemH gene: T11, T23, A48, T89, C188, G338, T464, T470, G536, T548, T608, G626, T632, T641, T671, T674, C683, C689, A740, G745, T787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8,
  in the hemL gene: T107, C197, T229, A242, C310, A338, A374, T389, G392, T442, C467, G470, C482, G518, and C641, wherein the positions are defined with reference to sequence SEQ ID NO: 9, and
  in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10.

In a particular embodiment, said genetic modification generates at least one change in at least one of the nucleotide variants in the hem locus associated with α-type *C. acnes* bacteria into a nucleotide variant in the hem locus associated with β-type *C. acnes* bacteria, as defined in the section "α-type *C. acnes* bacteria and β-type *C. acnes* bacteria".

Therefore, in a particular embodiment, said genetic modification generates at least one, more particularly at least 2, 3, 4, 5, 6, 7, 8, 9, 10, 20, 30, 40, 50, 60, 70, 80, 90, 100, 110, 120, 130, 140, 150, 160, 170, 180, 190, 200, 210, 218 or all of the following changes in the hem locus:
  in the hemA gene: T173G, A479G, T506C, A614G, T629G, C671A, T971C, A989G, T1085C, and T1094C, wherein the positions are defined with reference to sequence SEQ ID NO: 3,
  in the hemB gene: C142T, A155G, A176G, A183G, C224T, C245T, G248A, T281C, G311A, C314T, T346C, C374T, G377T, C452T, T626C, C683G, A693G, A720G, C738T, C794T, A920C, T944G, T992C, G1022C, and T1031C, wherein the positions are defined with reference to sequence SEQ ID NO: 4,
  in the hemC gene: G77A, A96G, C149G, A233G, T236C, T255C, A257G, A260C, C317T, A347G, T425C, T437C, A464G, A486G, A487G, C488T, A524G, A545G, A590G, T605C, A644G, A665G, C710T, C713G, A737G, A770G, A776G, T785A, T802C, G830A, C842T, T845C, G855A, C893G, A896T, C897T, G902A, G908T, A941G, and A947G, wherein the positions are defined with reference to sequence SEQ ID NO: 5,
  in the hemD gene: T11C, T41C, T50C, A150G, T155C, G159A, G176T, T257C, C266T, T278C, G323C, A324G, T362C, T367C, T374C, G387A, A398G, A399G, T407C, G422A, G425A, G432A, A446G, A459G, T464C, G595A, T617C, T643A, A644G, and C680T, wherein the positions are defined with reference to sequence SEQ ID NO: 6,
  in the hemE gene: T241C, T476C, A530G, T704C, A728G, G767C, T834A, A867G, A872G, A882C, and A957G, wherein the positions are defined with reference to sequence SEQ ID NO: 7,
  in the hemH gene: T11C, T23C, A48G, T89C, C188T, G338A, T464C, T470C, G536A, T548C, T608C, G626A, T632C, T641C, T671C, T674C, C683T, C689T, A740T, G745A, T787A, A797G, T893C, A898T, T1034C, T1039C, T1046C, C1071G, G1095A, C1109T, T1153C, T1358C, G1496C, C1511T, C1527T, G1532A, T1598C, T1712C, A1850G, G1901C, A1926G, C1931T, and C1997T, wherein the positions are defined with reference to sequence SEQ ID NO: 8,
  in the hemL gene: T107C, C197T, T229A, A242G, C310A, A338G, A374G, T389C, G392T, T442C, C467T, G470A, C482T, G518T, and C641G, wherein the positions are defined with reference to sequence SEQ ID NO: 9, and
  in the hemY gene: A89G, A236G, A354G, C383T, C392T, A395G, T398C, T465C, T474C, C521T, T538C, C566T, A593C, A767C, T782A, G863A, G920A, T927A, A932G, G935A, C979A, G989C, C1019G, T1055C, G1091A, T1136C, G1143A, G1152A, T1166C, T1172G, A1176G, T1184C, C1199T, C1205T, G1268A, G1278A, T1295C, T1318C, A1336G, G1343A, C1346T, G1355C, T1359G and C1395G, wherein the positions are defined with reference to sequence SEQ ID NO: 10.

The genetic modification can be a point mutation(s), a deletion(s), insertion(s) or any combination thereof. Preferably, the genetic modification is a point modification.

The genetic modification preferably eliminates, reduces, or increases the expression of a gene. The genetic modification can be in the translated or untranslated regions of a gene. The genetic modification can be in the promoter region of a gene or within any other region involved in gene regulation.

In a particular embodiment, the genetic modification eliminates and/or reduces the expression of one or several genes of the hem locus, i.e. hemA, hemB, hemC, hemD, hemE, hemH, hemL, and/or hemY genes in the C. acnes bacteria, preferably in α-type C. acnes bacteria. In a more particular embodiment, the genetic modification(s) eliminate(s) or reduce(s) porphyrin production by the C. acnes bacteria, in particular by α-type C. acnes bacteria.

In some embodiments, the genetic modification results in the change in at least 1, 2, 3, 4, 5, 6, 7, 8, 9, 10, 11, 12, 13, 14, 15, 20, 25, 30, 35, 40, 45, 50, 100, 200, 500, etc. amino acids to a different amino acid. In some embodiments, the genetic modification introduces a stop codon. In some embodiments, the genetic modification is outside protein coding sequences, within RNA, or within regulatory sequences. In some embodiments, the genetic modification introduces one or more rare codons so the expression of the protein is affected, preferably reduced. In some embodiments, the start codon is modified so the normal start is changed or abrogated.

In a particular embodiment, said genetic modification results in the fact that the modified C. acnes bacteria does not belong anymore to the group of α-type C. acnes bacteria, as defined in the section "α-type C. acnes bacteria and β-type C. acnes bacteria" above. In a preferred embodiment, said genetic modification results in the fact that the modified C. acnes bacteria becomes a β-type C. acnes bacteria, as defined in the section "α-type C. acnes bacteria and/3-type C. acnes bacteria" above.

The therapeutic or prophylactic agent which genetically modifies a DNA sequence in the α-type C. acnes bacteria to generate at least one change in said α-type C. acnes bacteria, preferably in the hem locus of said α-type C. acnes bacteria may be a phage, recombinant phage, packaged phagemid, plasmid, DNA- or RNA-containing vesicle, extracellular vesicle, bacteria or engineered bacteria, which encodes a gene editing enzyme or system targeting said hem locus, in particular at least one of the nucleotide variants as defined above, in said α-type C. acnes bacteria.

In a particular embodiment, the treating or preventing method of the invention comprises administering to said subject a therapeutically or prophylactically effective amount of a phage, recombinant phage, packaged phagemid, plasmid, DNA- or RNA-containing vesicle, extracellular vesicle, bacteria or engineered bacteria, which encodes a gene editing enzyme or system targeting said hem locus, in particular at least one of the nucleotide variants as defined above, in said α-type C. acnes bacteria.

Similarly, in a particular embodiment of the composition for use according to the present invention or the use of a therapeutic or prophylactic agent according to the present invention, the therapeutic or prophylactic agent is a phage, recombinant phage, packaged phagemid, plasmid, DNA- or RNA-containing vesicle, extracellular vesicle, bacteria or engineered bacteria, which encodes a gene editing enzyme or system targeting and genetically modifying said hem locus, in particular at least one of the nucleotide variants as defined above, in said α-type C. acnes bacteria.

As used herein, the term "gene editing" refers to a type of genetic engineering in which DNA is inserted, deleted, modified or replaced in the genome of a living organism.

By "gene editing system" is meant herein a combination of components required for gene editing of a genome in a cell. The various components of the system, such as polypeptides, gRNA, etc., may exist independently of each other, or may exist in any combination thereof.

By "gene editing enzyme" is meant herein an enzyme enabling the gene editing of a genome in a cell. Said gene editing enzyme can typically be part of a gene editing system as defined above, and be used with another component of the system.

In a particular embodiment, the gene editing enzyme or system is a base editing enzyme or system.

Base editing (BE) refers to the ability to substitute a specific nucleotide base pair on a DNA or RNA molecule by another. In base editing technology, there is no exchange of DNA, instead an enzymatic reaction converts a nucleotide to another one leading to a mismatch at the level of dsDNA that is then corrected by the cell machinery.

In some embodiments, the base editing system comprises one or more of the following enzymes and systems:

Cytosine base editors (CBE) and Adenosine base editors (ABE), as described in Rees and Liu (2018) NatRev Genet 19:770-788.

Examples of DNA Base Editors Include

Cytosine Base Editor (CBE) that converts C:G into T:A (Komor et al. (2016) Nature 533:420-4);
Adenine Base Editor (ABE) that converts A:T into G:C (Gaudelli et al. (2017) Nature 551(7681):464-471);
Cytosine Guanine Base Editor (CGBE) that converts C:G into G:C (Chen et al. (2020) Precise and programmable C:G to G:C base editing in genomic DNA. Biorxiv; Kurt et al. (2020) CRISPR C-to-G base editors for inducing targeted DNA transversions in human cells. Nature Biotechnology);
Cytosine Adenine Base Editor (CABE) that converts C:G into A:T (Zhao et al. (2020) New base editors change C to A in bacteria and C to G in mammalian cells. Nature Biotechnology);
Adenine Cytosine Base Editor (ACBE) that converts A:T into C:G (WO2020181180);
Adenine Thymine Base Editor (ATBE) that converts A:T into T:A (WO2020181202);
Thymine Adenine Base Editor (TABE) that converts T:A into A:T (WO2020181193; WO2020181178; WO2020181195).

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an E. coli tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition;

the addition of Mu-GAM that decrease insertion-deletion rate by inhibiting Non-homologous end joining mechanism in the cell (NHEJ);

the use of nickase active Cas9 (nCas9 D10A) that, by creating nicks on the non-edited strand favors its repair and consequently the fixation of the edited base;

the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (C G B E) consist of a nickase CRISPR fused to:

A cytosine deaminase (rAPOBEC) and base excision repair proteins (e.g. rXRCC1) (Chen et al. Precise and programmable C:G to G:C base editing in genomic DNA. Biorxiv (2020); Chen et al. (2021) Nature Communications 12:1384);

A ratAPOBEC1 variant (R33A) protein and an E. coli-derived uracil DNA N-glycosylase (eUNG) (Kurt et al. (2020) CRISPR C-to-G base editors for inducing targeted DNA transversions in human cells. Nature Biotechnology).

Cytosine Adenine Base Editors (CABE) consist of a Cas9 nickase, a cytidine deaminase (e.g. AID), and a uracil-DNA glycosylase (Ung) (Zhao et al. (2020) New base editors change C to A in bacteria and C to G in mammalian cells. Nature Biotechnology).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald et al. (2020) A dual-deaminase CRISPR base editor enables concurrent adenine and cytosine editing, Nature Biotechnology; Li et al. (2020) Targeted, random mutagenesis of plant genes with dual cytosine and adenine base editors, Nature Biotechnology).

In a particular embodiment, the base editing enzyme is a fusion protein comprising a Cas9 (e.g., a Cas9 nickase) domain and a deaminase domain. In some embodiments, the base editing enzyme comprises Cas9 and a cytosine deaminase enzyme, such as APOBEC enzymes, or adenosine deaminase enzymes, such as ADAT enzymes, for example as disclosed in U.S. Patent Publ. 2015/0166980. In one embodiment, the deaminase is an ACF1/ASE deaminase. In various embodiments, the APOBEC enzyme is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the base editing enzyme comprises a Cas9 domain, a cytosine deaminase domain, and a uracil glycosylase inhibitor (UGI) domain. In one embodiment, the deaminase is an adenosine deaminase that deaminates adenosine in DNA, for example as disclosed in U.S. Pat. No. 10,113,163. In some embodiments, the base editing system further comprises an inhibitor of base repair, such as a nuclease dead inosine specific nuclease (dISN), for example as disclosed in U.S. Pat. No. 10,113,163.

In a particular embodiment, the base editing system comprises a Cytosine base editor (CBE) and/or an Adenosine base editor (ABE) as defined above.

In another particular embodiment, the gene editing enzyme or system is a prime editing enzyme or system.

Prime Editing (PE) allows introduction of insertions, deletions (indels), and multiple base-to-base conversions. Prime editing typically relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editors, as described in Anzalone et al. (2019) Nature 576:149-157, typically consist of a nCas9 fused to a reverse transcriptase used in combination with a prime editing RNA (pegRNA; a guide RNA that includes a template region for reverse transcription).

Prime editing systems typically include:

a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F), and a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include P E 1, P E 1-M1, P E 1-M 2, P E 1-M 3, P E1-M6, PE1-M15, P E1-M3inv, P E2, PE 3, PE 3b.

In various embodiments, the prime editing system comprises a fusion protein comprising a catalytically impaired Cas9 endonuclease fused to an engineered reverse transcriptase, programmed with a prime editing guide RNA (pegRNA) that both specifies the target site and encodes the desired edit, for example as described in (2019) Nature 576:149-157.

Other suitable gene editing systems or enzymes include:

Cas9 Retron precISe Parallel Editing via homologY ('CRISPEY'), a retron RNA fused to the sgRNA and expressed together with Cas9 and the retron proteins including at least the reverse transcriptase (Sharon et al. (2018) Cell 175:544-557.e16).

The SCRIBE strategy: a retron system expressed in combination with a recombinase promoting the recombination of single stranded DNA, also known as single stranded annealing proteins (SSAPs) (Farzadfard and Lu (2014) Science 346:1256272). Such recombinases include but are not limited to phage recombinases such as lambda red, recET, Sak, Sak4, and SSAPs described in Wannier et al. Improved bacterial recombineering by parallelized protein discovery. Biorxiv 2020.01.14.906594 (2020) doi:10.1101/2020.01.14.906594.

The targetron system based on group II introns described in Karberg et al. Nat Biotechnol (2001) 19:1162-7 which has been adapted to many bacterial species.

Other retron based gene targeting approaches as described in Simon et al. (2019) Nucleic Acids Res 47:11007-11019.

A bridge system based on IS1111 and IS110 insertion sequence (IS) family members and using a non-coding RNA (ncRNA) with two distinct binding loops that separately recognize the IS DNA donor and its genomic insertion target site. By bridging the donor and target DNA molecules through direct base-pairing interactions, the bispecific bridge RNA facilitates DNA recombination by the IS recombinase (Durrant et al. Nature. 2024 Jun; 630(8018):984-993; Siddiquee et al. Nat Commun 15, 5235 (2024)).

In a particular embodiment, said gene editing system or enzyme is a base editor or a prime editor, as defined above.

The present invention also concerns a method for treating or preventing a *C. acnes* bacteria-associated disease in a subject, said method comprising specifically reducing the expression of at least one hem locus protein in α-type *C. acnes* bacteria in said subject, wherein α-type *C. acnes* bacteria are *C. acnes* bacteria as defined in the section "α-type *C. acnes* bacteria and β-type *C. acnes* bacteria" above.

It also concerns a composition for use in the treatment or prevention of a *C. acnes* bacteria-associated disease in a subject, said composition comprising a therapeutic or prophylactic agent which specifically reduces the expression of at least one hem locus protein in α-type *C. acnes* bacteria in said subject by genetically modifying a DNA sequence in α-type *C. acnes* bacteria in said subject, to generate at least one change, preferably in the hem locus of said α-type *C. acnes* bacteria, and wherein α-type *C. acnes* bacteria are *C. acnes* bacteria as defined in the section "α-type *C. acnes* bacteria and β-type *C. acnes* bacteria" above.

It further concerns the use of a therapeutic or prophylactic agent for the manufacture of a medicament for the treatment or prevention of a *C. acnes* bacteria-associated disease in a subject, wherein said therapeutic or prophylactic agent specifically reduces the expression of at least one hem locus protein in α-type *C. acnes* bacteria in said subject by genetically modifying a DNA sequence in α-type *C. acnes* bacteria in said subject, to generate at least one change, preferably in the hem locus of said α-type *C. acnes* bacteria, and wherein α-type *C. acnes* bacteria are *C. acnes* bacteria as defined in the section "α-type *C. acnes* bacteria and β-type *C. acnes* bacteria" above.

The therapeutic or prophylactic agent may be as defined above.

In a particular embodiment, the therapeutic or prophylactic agent which specifically reduces the expression of at least one hem locus protein in α-type *C. acnes* bacteria in said subject by genetically modifying a DNA sequence in α-type *C. acnes* bacteria in said subject is a phage, recombinant phage, packaged phagemid, plasmid, DNA- or RNA-containing vesicle, extracellular vesicle, bacteria or engineered bacteria, which encodes a gene editing enzyme or system targeting said hem locus, in particular at least one of the nucleotide variants as defined above, in said α-type *C. acnes* bacteria.

In a particular embodiment, the treating or preventing method of the invention comprises administering to said subject a therapeutically or prophylactically effective amount of a therapeutic or prophylactic agent which specifically reduces the expression of at least one hem locus protein in α-type *C. acnes* bacteria in said subject by genetically modifying a DNA sequence in α-type *C. acnes* bacteria in said subject. Preferably, said therapeutic or prophylactic agent is a phage, recombinant phage, packaged phagemid, plasmid, DNA- or RNA-containing vesicle, extracellular vesicle, bacteria or engineered bacteria, which encodes a gene editing enzyme or system targeting said hem locus, in particular at least one of the nucleotide variants as defined above.

The genetic modification may be as defined above and may be carried out as described above.

In a particular embodiment, the genetic modification eliminates and/or reduces the expression of one or several genes of the hem locus, i.e. hemA, hemB, hemC, hemD, hemE, hemH, hemL, and/or hemY genes in α-type *C. acnes* bacteria.

In a more particular embodiment, the genetic modification(s) eliminate(s) or reduce(s) porphyrin production by α-type *C. acnes* bacteria.

By "specifically reducing the expression of at least one hem locus protein in α-type *C. acnes*" is meant herein that the expression of said at least one hem locus protein, i.e. hemA, hemB, hemC, hemD, hemE, hemH, hemL, and/or hemY proteins, in said subject, in particular on the skin of said subject, of *C. acnes* bacteria of another type than α-type, in particular of β-type *C. acnes* bacteria, and/or of other bacterial species, is not significantly reduced, preferably that the expression of said at least one hem locus protein, in said subject, in particular on the skin of said subject, of *C. acnes* bacteria of another type than α-type, in particular of β-type *C. acnes* bacteria is not significantly reduced. Preferably, the expression of said at least one hem locus protein of *C. acnes* bacteria of another type than α-type, in particular of β-type *C. acnes* bacteria, and/or of other bacterial species, is reduced by less than 20%, preferably less than 10%, compared to a non-treated population or compared to the population of *C. acnes* bacteria of another type than α-type, in particular of β-type *C. acnes* bacteria, and/or of other bacterial species, in the subject before the implementation of the method and/or the administration of the therapeutic or prophylactic agent.

The genetic modification(s) inducing the reduction of expression of at least one hem locus protein may affect or not the ratio of the amount of α-type *C. acnes* bacteria to the amount of β-type *C. acnes* bacteria, i.e. the genetic modification(s) may result or not in the fact that the modified *C. acnes* bacteria does not belong anymore to the group of α-type *C. acnes* bacteria, as defined in the section "α-type *C. acnes* bacteria and β-type *C. acnes* bacteria" above. In some particular embodiments, the ratio of the amount of α-type *C. acnes* bacteria to the amount of β-type *C. acnes* bacteria is not affected by the genetic modification(s).

Increasing the Amount of β-Type *C. acnes* Bacteria

In a particular embodiment, the treating or preventing method of the invention comprises increasing the amount of β-type *C. acnes* bacteria, as defined in the section "α-type *C. acnes* bacteria and β-type *C. acnes* bacteria" above, in said subject, in particular on the skin of said subject.

The present invention therefore concerns a method for treating or preventing a *C. acnes* bacteria-associated disease in a subject, said method comprising increasing the amount of β-type *C. acnes* bacteria in said subject, in particular on the skin of said subject. It also concerns a composition for use in the treatment or prevention of a C. acnes bacteria-associated disease in a subject, said composition comprising a therapeutic or prophylactic agent which increases the amount of β-type C. acnes bacteria in said subject, in particular on the skin of said subject. It further concerns the use of a therapeutic or prophylactic agent which increases the amount of β-type C. acnes bacteria in a subject, in particular on the skin of said subject, for the manufacture of a medicament for the treatment or prevention of a C. acnes bacteria-associated disease in said subject.

As used herein, the term "amount" has the same meaning as disclosed in the section "Method of treatment or prevention of C. acnes bacteria-associated disease" above.

In a particular embodiment, the amount of β-type C. acnes bacteria, as defined in the section "α-type C. acnes bacteria and β-type C. acnes bacteria" above, is specifically increased, in said subject, in particular on the skin of said subject.

By "specifically increase the amount of β-type C. acnes bacteria" is meant herein that the amount, in said subject, in particular on the skin of said subject, of C. acnes bacteria of another type than β-type, in particular of α-type C. acnes bacteria, is not significantly increased, and/or the amount, in said subject, in particular on the skin of said subject, of other bacterial species is not significantly increased.

By "increase of the amount" is meant herein an increase of the amount after the implementation of the method compared to the amount in the absence of or before the implementation of the method.

In a particular embodiment, the increase of the amount is a statistically significant increase.

In a particular embodiment, said increase of the amount is observed 1 day after the first implementation of the method, in particular 2 days, 3 days, 4 days, 5 days, 6 days, 7 days, 2 weeks, 3 weeks, or 1 month after the first implementation of the method.

In a particular embodiment, said increase of the amount is maintained (not necessarily at the same level) for 1 day after the first implementation of the method, in particular 2 days, 3 days, 4 days, 5 days, 6 days, 7 days, 2 weeks, 3 weeks, 1 month, 2 months, 3 months, 4 months, 5 months, 6 months or 1 year after the first implementation of the method.

In a particular embodiment, said increase of the amount is maintained (not necessarily at the same level) for the whole period during which the method is implemented.

In a particular embodiment, the treating or preventing method of the invention comprises administering β-type C. acnes bacteria, as defined in the section "α-type C. acnes bacteria and β-type C. acnes bacteria" above, in said subject, in particular on the skin of said subject.

In particular, the therapeutic or prophylactic agent which increases the amount of β-type C. acnes bacteria may be a phage, recombinant phage, packaged phagemid, plasmid, DNA- or RNA-containing vesicle, extracellular vesicle, bacteria or engineered bacteria, which encodes a gene editing enzyme or system targeting the hem locus of α-type C. acnes bacteria, in particular the alpha nucleotide variants as defined in Table 1, to generate changes in said α-type C. acnes bacteria, said changes resulting in the fact that the modified α-type C. acnes bacteria becomes β-type C. acnes bacteria.

Subject, Regimen and Administration

The subject according to the invention is an animal, preferably a mammal, even more preferably a human. However, the term "subject" can also refer to non-human animals, in particular mammals.

The human subject according to the invention may be a new-born, a child, an infant, an adolescent or an adult at any age. In a particular embodiment, the human subject is an adolescent.

In a preferred embodiment, the subject has been diagnosed with, or is at risk of developing acne, in particular acne vulgaris. In a preferred embodiment, the subject has been diagnosed with acne, in particular acne vulgaris, using the diagnostic method disclosed in the section "Risk of developing acne and diagnosis" below. In a preferred embodiment, the subject has been identified as being at risk of developing acne, in particular acne vulgaris, using the method disclosed in the section "Risk of developing acne and diagnosis" below.

In a particular embodiment, the subject has never received any treatment before the treating or preventing method of the invention.

In a particular embodiment, the subject has already received at least one line of treatment, preferably several lines of treatment, prior to the treating or preventing method of the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 times a day.

The duration of treatment according to the invention is preferably between 1 day and 1 year, more preferably between 1 week and 6 months, still more preferably between 2 weeks and 3 months, even more preferably between 3 weeks and 2 months. In a particular embodiment, the duration of the treatment is about 1 month. Alternatively, the treatment may last as long as the disease persists.

The form of the pharmaceutical compositions, the route of administration and the dose of administration of therapeutic or prophylactic agents according to the invention can be adjusted by the man skilled in the art according to the type and severity of the disease, and to the patient or subject, in particular its age, weight, sex, and general physical condition.

Particularly, the amount of therapeutic or prophylactic agent to be administered has to be determined by standard procedure well known by those of ordinary skills in the art. Physiological data of the patient or subject (e.g. age, size, and weight) and the routes of administration have to be taken into account to determine the appropriate dosage, so as a therapeutically or prophylactically effective amount will be administered to the patient or subject.

For example, the total amount of phages, engineered phages or packaged phagemids according to the invention, for each administration is typically comprised between $10^4$ and $10^{15}$ delivery vehicles.

The preferred route of administration used in the context of the invention is the topical administration.

It is envisioned that the treating or preventing method of the invention can be used in combination with other standard treatments. For example, in some embodiments, the treating or preventing method of the invention is implemented before, after, or simultaneously with administration of an additional therapeutic agent or with implementation of an additional treating or preventing method. In some embodiments, said additional therapeutic agent may be a topical antibiotic. Non-limiting examples of topical antibiotics include clindamycin, doxycycline, erythromycin, and tetracycline. In some embodiments, said additional therapeutic agent may be an oral antibiotic. Non-limiting examples of oral antibiotics include erythromycin; or a tetracycline, such as doxycycline or minocycline. Other additional therapeutic agents may comprise anti-inflammatory agents, antioxidants, acids, or a combination thereof.

In some embodiments, said additional treating or preventing method is light therapy. In some embodiments, said additional treating or preventing method is a laser treatment. In some embodiments, said additional treating or preventing method comprises treating the subject with blue light. In some embodiments, said additional treating or preventing method comprises treating the subject with red light. In some embodiments, said additional treating or preventing method comprises treating the subject with a targeted laser device. In some embodiments, said additional treating or preventing method comprises treating the subject with a laser that targets porphyrins.

A combination of additional therapeutic agent(s) and of additional treating or preventing method(s), as disclosed above, may also be used.

Pharmaceutical Composition

The present invention also concerns a pharmaceutical composition comprising a phage, recombinant phage, packaged phagemid, plasmid, DNA- or RNA-containing vesicle, extracellular vesicle, bacteria or engineered bacteria, as defined in the section "Specifically reducing the amount of α-type C. acnes bacteria" above, which encodes a programmable nuclease as defined in the section "Specifically reducing the amount of α-type C. acnes bacteria" above, or a gene editing enzyme or system as defined in the section "Genetically modifying a DNA sequence in the α-type C. acnes bacteria" above, designed to specifically target a α-type C. acnes bacteria, wherein α-type C. acnes bacteria are as defined in the section "α-type C. acnes bacteria and #-type C. acnes bacteria" above.

In a particular embodiment, said pharmaceutical composition further comprises a pharmaceutically acceptable vehicle.

By "pharmaceutically acceptable vehicle" is meant herein pharmaceutical ingredients known to be useful for preparing pharmaceutical compositions to be administered to patients in need. Such ingredients are safe and non-sensitizing under the conditions used.

Pharmaceutically acceptable vehicles are known to one of ordinary skill in the art, and include common excipients, diluents, or carriers.

In a particular embodiment, said pharmaceutical composition further comprises at least one pharmaceutical acceptable excipient and/or adjuvant.

By "pharmaceutically acceptable excipient" is meant herein a non-pharmaceutically active additive used in the manufacture of a pharmaceutical composition, which allows the pharmaceutically active ingredient to be manufactured into a pharmaceutical composition or a galenic formulation providing the necessary bioavailability of the medicament to the patient upon the administration of the pharmaceutical composition. The excipient is preferably compatible with the other ingredients of the composition and produces no adverse effect, allergic reaction or other undesirable reaction when it is administered to a human or an animal.

By "pharmaceutically acceptable adjuvant" is meant herein a substance that is non-toxic, biologically tolerable, and otherwise biologically suitable for administration to a subject, added to a pharmaceutical composition to strengthen the role of the excipient or of a therapeutically active ingredient.

In a particular embodiment, said pharmaceutical composition further comprises an additional therapeutically active agent.

By "additional therapeutically active agent" is meant herein any chemical, biochemical, organic, inorganic compound, composition, element or substance that is designated or can be used for the treatment of diseases, disorders, malfunctions, etc. of a living being or of biological material in general, and which is different from the therapeutic or prophylactic agents defined in the sections "Method of treatment or prevention of C. acnes bacteria-associated disease", "Specifically reducing the amount of α-type C. acnes bacteria", "Genetically modifying a DNA sequence in the α-type C. acnes bacteria" and/or "Increasing the amount of β-type C. acnes bacteria" above.

Said additional therapeutically active agent can be selected from the group consisting of nonsteroidal anti-inflammatory drugs (NSAIDs) analgesics; opiate agonist analgesics; salicylate analgesics; H1-blocker antihistamines; H2-blocker antihistamines; anti-infective agents; anti-anaerobic anti-infectives; antifungal antibiotic anti-infectives; macrolide antibiotic anti-infectives; miscellaneous beta-lactam antibiotic anti-infectives; penicillin antibiotic anti-infectives; quinolone antibiotic anti-infectives; tetracycline antibiotic anti-infectives; antituberculosis antimycobacterial anti-infectives; antiprotozoal anti-infectives; antimalarial antiprotozoal anti-infectives; anti-retroviral anti-infectives; antiviral anti-infective agents; alkylating antineoplastic agents; nitrosourea alkylating antineoplastic agents; antimetabolite antineoplastic agents; pyrimidine analog antimetabolite antineoplastic agents; hormonal antineoplastics; natural antineoplastics; antibiotic natural antineoplastics; vinca alkaloid natural antineoplastics; autonomic agents; anticholinergic autonomic agents; antimuscarinic anticholinergic autonomic agents; ergot alkaloid autonomic agents; cholinergic agonist parasympathomimetics; cholinesterase inhibitor parasympathomimetics; alpha-blocker sympatholytics; beta-blocker sympatholytics; adrenergic agonist sympathomimetics; cardiovascular agents; beta-blocker antianginals; calcium-channel blocker antianginals; nitrate antianginals; cardiac glycoside antiarrhythmics; class I antiarrhythmics; class II antiarrhythmics; class III antiarrhythmics; class IV antiarrhythmics; alpha-blocker antihypertensives; angiotensin-converting enzyme inhibitor (ACE inhibitor) antihypertensives; beta blocker antihypertensives; calcium-channel blocker antihypertensive agents; central-acting adrenergic antihypertensives; diuretic antihypertensive agents; peripheral vasodilator antihypertensives; antilipemics; bile acid sequestrant antilipemics; HMG-CoA reductase inhibitor antilipemics; inotropes; cardiac glycoside inotropes; thrombolytic agents or enzymes; dermatological agents; dermatological corticosteroid anti-inflammatory agents; antifungal topical antiinfectives; antiviral topical anti-infectives; topical antineoplastics; electrolytic and renal agents; loop diuretics; potassium-sparing diuretics; thiazide diuretics; uricosuric agents; enzymes such as RNase and DNase; immunosuppressive agents; antiemetics; salicylate gastrointestinal anti-inflammatory agents; gastric acid-pump inhibitor anti-ulcer agents; H2-blocker anti-ulcer agents; digestants; prokinetic agents; opiate agonist intravenous anesthetics; hematopoietic anti anemia agents; coagulation agents; anticoagulants; growth receptor inhibitors; abortifacients; antidiabetic agents; oral contraceptives; progestin contraceptives; estrogens; fertility agents; parathyroid agents; pituitary hormones; progestins; thyroid hormones; immunobiologic agents; immunoglobulins; amide local anesthetics; ester local anesthetics; musculoskeletal corticosteroid anti-inflammatory agents; musculoskeletal anti-inflammatory immunosuppressives; musculoskeletal non-steroidal anti-inflammatory drugs (NSAIDs); skeletal muscle relaxants; reverse neuromuscular blocker skeletal muscle relaxants; neurological agents; anticonvulsants; barbiturate anticonvulsants; benzodiazepine anticonvulsants; anti-Parkinson's agents; antivertigo agents; opiate agonists; opiate antagonists; beta-blocker anti-glaucoma agents; miotic anti-glaucoma agents; ophthalmic aminoglycoside antiinfectives; ophthalmic quinolone anti-infectives; ophthalmic corticosteroid anti-inflammatory agents; ophthalmic nonsteroidal anti-inflammatory drugs (NSAIDs); antipsychotics; benzodiazepine anxiolytics, sedatives and hypnotics; psychostimulants; antitussives; bronchodilators; adrenergic agonist bronchodilators; respiratory corticosteroid anti-inflammatory agents; antidotes; heavy metal antagonists/chelating agents; deterrent substance abuse agents; withdrawal substance abuse agents; minerals, such as iron, calcium, and magnesium; vitamin B compounds, such as cyanocobalamin (vitamin B12) and niacin (vitamin B3); vitamin C compounds; vitamin D compounds, such as calcitriol; vitamin A, vitamin E, and vitamin E compounds; anti-bleeding agents; anthelmintic anti-infectives; sclerosants; anabolic agents; antacids; anti-asthmatic agents; anti-cholesterolemic and anti-lipid agents; anti-diarrheals; anti-manic agents; anti-nauseants; anti-obesity agents; antipyretic and analgesic agents; antispasmodic agents; antithrombotic agents; anti-uricemic agents; anti-tussives; appetite suppressants; cerebral dilators; coronary dilators; decongestants; diagnostic agents; erythropoietic agents; expectorants; gastrointestinal sedatives; hyperglycemic agents; hypoglycemic agents; ion exchange resins; laxatives; mucolytic agents; neuromuscular drugs; peripheral vasodilators; psychotropics, stimulants; thyroid and antithyroid agents; and uterine relaxants.

In a particular embodiment, said pharmaceutical composition may further comprise a skin care agent.

By "skin care agent" is meant herein an agent that has one or more beneficial effects on the care and/or hygiene of the skin. The skin care agent can be selected from the group consisting of antioxidants, free-radical scavengers, skin protecting agents, skin conditioning agents, skin soothing agents, exfoliators, moisturizers, emollients and humectants.

By "skin conditioning agent" is meant herein an agent that can maintain the skin in a good condition. Examples of skin conditioning agents include urea, guanidine, aloe vera, glycolic acid and glycolate salts such as ammonium and quaternary alkyl ammonium, lactic acid and lactate salts such as sodium lactate, ammonium lactate and quaternary alkyl ammonium lactate, polyhydroxy alcohols such as sorbitol, glycerol, hexanetriol, tocopherol, propylene glycol, butylene glycol, hexylene glycol, polyethylene glycol, carbohydrates such as alkoxylated glucose, starches, starch derivatives, glycerin, pyrrolidone carboxylic acid (PCA), lactamide monoethanolamine, acetamide monoethanolamine, volatile silicone oils, nonvolatile silicone oils, *Helianthus annuus* seed oil, phospholipids, Salix alba (willow) bark extract, glycine soja seed extract, and mixtures thereof.

Examples of skin soothing agents include bisabolol.

As used herein, "skin protecting agents" are agents that protect the skin against chemical irritants and/or physical irritants, such as UV light, including sunscreens, anti-wrinkle and anti-skin atrophy agents.

Examples of UV blocking agents include 2-ethylhexyl p-methoxycinnamate, 2-ethylhexyl N,N-dimethyl-p-amino-benzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoyl-methane, 4-isopropy dibenzoylmethane, 3-benzylidene camphor, 3-(4-methylbenzylidene) camphor, anthanilates, ultrafine titanium dioxide, zinc oxide, iron oxide, silica, 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone and 4-N,N (2-ethylhexyl)-methylaminobenzoic acid ester of 4-(2-hydroxyethoxy)dibenzoylmethane.

Examples of anti-wrinkle and anti-skin atrophy agents include retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

Examples of antioxidants and/or free-radical scavengers include ascorbic acid, salts of ascorbic acid such as ascorbyl palmitate and sodium ascorbate, ascorbyl glucosamine, vitamin E (i.e., tocopherols such as α-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), lipoic acid, sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), butylated hydroxyanisole (BHA), indole-3-carbinol, pycnogenol, melatonin, sulforaphane, pregnenolone, lipoic acid and 4-hydroxy-5-methyl-3[2H]-furanone.

Examples of exfoliants include hydroxy carboxylic acids such as alpha hydroxy acids or beta hydroxy acids, keto acids and hydroxybenzoic acids.

Examples of moisturizers include lactic acid and other hydroxy acids and their salts, glycerol, propylene glycol, butylene glycol, sodium PCA, sodium hyaluronate, Carbowax 200, Carbowax 400 and Carbowax 800.

Examples of emollients or humectants include panthenol, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, ceramides (e.g. ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, and 1,3-bis(N-2-(hydroxyethyl) palmitoylamino)-2-hydroxypropane.

The pharmaceutical composition of the invention can be formulated under any suitable form well-known from the skilled person.

In a particular embodiment, said composition is in the form of aqueous, hydroalcoholic or oily solutions, of dispersions in the form of solutions or dispersions of the lotion or serum type, of emulsions, in particular with liquid or semi-liquid consistency of the milk type, typically obtained by dispersion of a fatty phase in an aqueous phase (O/W) or conversely (W/O), or suspensions or emulsions of soft semi-solid or solid consistency of the cream type, of cream, of aqueous or anhydrous gel, of microemulsions, of nanoemulsions, of microcapsules, of microparticles, of ionic and/or nonionic type vesicular dispersions, of stick, of aerosol spray, of pump spray, or of foam. In a particular embodiment, said composition is in the form of an emulsion, of a microemulsion or of a nanoemulsion.

The pharmaceutical composition of the invention can be in any form well-known from the skilled person, typically depending on its administration route.

For oral administration, the pharmaceutical composition can be in the form of tablets, capsules, sugar-coated pills, syrups, suspensions, solutions, powders, granules, emulsions, suspensions of microspheres or nanospheres or lipid or polymer vesicles providing controlled release.

For parenteral administration, the pharmaceutical composition can be in the form of solutions or suspensions for infusion or for injection.

For topical application, the pharmaceutical composition can be in the form of unguents, creams, milks, ointments, powders, impregnated tampons, solutions, gels, sprays, lotions or suspensions. It can also be in the form of suspensions of microspheres or nanospheres or lipid or polymer vesicles or polymer patches or hydrogels providing controlled release. This formulation for topical application can be in anhydrous form, in aqueous form or in the form of an emulsion.

Preferably, the pharmaceutical composition of the invention is for topical application.

The pharmaceutical composition according to the present invention can be prepared by mixing the essential ingredient(s), and optional ingredient(s), if necessary.

The method and means to mix the above essential and optional ingredients are not limited. Any conventional method and means can be used to mix the above essential and optional ingredients to prepare the formulation according to the present invention.

Risk of Developing Acne and Diagnosis

The present invention also relates to a method for determining if a subject is at risk of developing acne, in particular acne vulgaris, said method comprising the steps of:
a) determining the presence and/or amount of α-type *C. acnes* bacteria in a sample, in particular a skin sample, of said subject, wherein α-type *C. acnes* bacteria are as defined in the section "α-type *C. acnes* bacteria and β-type *C. acnes* bacteria" above, and
b) based on the presence and/or amount determined at step a), determining if said subject is at risk of developing acne, in particular acne vulgaris.

The present invention also relates to a method for determining if a subject is at risk of developing acne, in particular acne vulgaris, said method comprising the steps of:
a) determining the presence and/or amount of β-type *C. acnes* bacteria in a sample, in particular a skin sample, of said subject, wherein β-type *C. acnes* bacteria are as defined in the section "α-type *C. acnes* bacteria and β-type *C. acnes* bacteria" above, and
b) based on the presence and/or amount determined at step a), determining if said subject is at risk of developing acne, in particular acne vulgaris.

The present invention also relates to a method of diagnosing acne, in particular acne vulgaris, in a subject, said method comprising the steps of:
a) determining the presence and/or amount of α-type *C. acnes* bacteria in a sample, in particular a skin sample, of said subject, wherein α-type *C. acnes* bacteria are as defined in the section "α-type *C. acnes* bacteria and β-type *C. acnes* bacteria" above, and
b) based on the presence and/or amount determined at step a), diagnosing acne, in particular acne vulgaris, in said subject.

The present invention also relates to a method of diagnosing acne, in particular acne vulgaris, in a subject, said method comprising the steps of:
a) determining the presence and/or amount of β-type *C. acnes* bacteria in a sample, in particular a skin sample, of said subject, wherein β-type *C. acnes* bacteria are as defined in the section "α-type *C. acnes* bacteria and β-type *C. acnes* bacteria" above, and
b) based on the presence and/or amount determined at step a), diagnosing acne, in particular acne vulgaris, in said subject.

As used herein, the term "amount" has the same meaning as disclosed in the section "Method of treatment or prevention of *C. acnes* bacteria-associated disease" above.

In a preferred embodiment of said methods, the amount of α-type *C. acnes* bacteria or p-type *C. acnes* bacteria, is the relative abundance of α-type *C. acnes* bacteria or β-type *C. acnes* bacteria.

As used herein, the term "presence" means that the amount of said α-type *C. acnes* bacteria or β-type *C. acnes* bacteria in said sample is within the detectable range of the techniques used to detect bacteria, more particularly said α-type *C. acnes* bacteria or β-type *C. acnes* bacteria. In other words, when it is determined that said α-type *C. acnes* bacteria or β-type *C. acnes* bacteria are not present in said sample, it means that they are below the detection threshold of the technique used for this determination step.

Preferably, said sample is a skin sample.

The skin sample may be any sample taken from the skin of a subject. A skin sample may be obtained by any means known in the art including, but not limited to, swabbing the skin with a tool able to collect skin cells (e.g., a Q-tip or cotton swab), placing an adhesive or tape on the surface of the skin and removing the adhesive or tape, thereby yielding a skin sample on the adhesive or tape, or through a biopsy (e.g., a shave biopsy, a punch biopsy, an incisional biopsy, a saucerization biopsy, or an excisional biopsy). As will be understood by the skilled person, the skin sample needs to be obtained by any means which enables collecting the bacteria present on the skin of the subject, preferably in the skin follicle of the subject. Therefore, the skin sample comprises at least a part of the skin microbiome.

In some embodiments, the skin sample further includes epithelial cells, epidermal cells, dermal cells, hair/skin follicles, adipose tissue (i.e., subcutaneous fat), and/or connective tissue.

As underlined above and in the examples below, the present inventors showed that a set of 218 SNPs across the hem locus (comprising the genes hemA, hemB, hemC, hemD, hemE, hemH, hemL, and hemY) can separate the known *C. acnes* strain diversity in 2 groups, herein called α-type and β-type. Importantly, this new typing correlates with the published porphyrin production levels, more precisely than the deoR gene. Moreover, after developing a method for the estimation of relative abundances of α-type and β-type *C. acnes* strains in shotgun metagenomic sequencing data, and applying it to a public data set associated to a study characterizing the skin microbiome in acne vulgaris (Barnard et al. (2016) Scientific Reports 6:39491), the present inventors demonstrated that α-type *C. acnes* strains were significantly more abundant in patients suffering from acne vulgaris than healthy subjects.

Therefore, in the methods for determining if a subject is at risk of developing acne, in particular acne vulgaris, of the invention, the subject is determined as being at risk of developing acne, in particular acne vulgaris, when (i) the α-type C. acnes bacteria are determined to be present in said sample and/or when the amount, in particular the relative abundance (for example with respect to the whole bacterial population, in particular skin bacterial population, of the subject, or with respect to the whole C. acnes population, in particular skin C. acnes population, of the subject), of α-type C. acnes bacteria is determined to be higher than a reference value or (ii) when the β-type C. acnes bacteria are determined to be present in said sample and/or when the amount, in particular the relative abundance (for example with respect to the whole bacterial population, in particular skin bacterial population, of the subject, or with respect to the whole C. acnes population, in particular skin C. acnes population, of the subject), of β-type C. acnes bacteria is determined to be lower than a reference value. Similarly, in the diagnosis method of the invention, the subject is diagnosed as suffering from acne, in particular acne vulgaris, when (i) the α-type C. acnes bacteria are determined to be present in said sample and/or when the amount, in particular the relative abundance (for example with respect to the whole bacterial population, in particular skin bacterial population, of the subject, or with respect to the whole C. acnes population, in particular skin C. acnes population, of the subject), of α-type C. acnes bacteria is determined to be higher than a reference value or (ii) when the β-type C. acnes bacteria are determined to be present in said sample and/or when the amount, in particular the relative abundance (for example with respect to the whole bacterial population, in particular skin bacterial population, of the subject, or with respect to the whole C. acnes population, in particular skin C. acnes population, of the subject), of β-type C. acnes bacteria is determined to be lower than a reference value.

In a particular embodiment, said reference value is the amount, in particular the relative abundance (for example with respect to the whole bacterial population, in particular skin bacterial population, of the subject, or with respect to the whole C. acnes population, in particular skin C. acnes population, of the subject), of α-type C. acnes bacteria, respectively β-type C. acnes bacteria, in a corresponding sample, in particular skin sample, of a healthy subject.

By "healthy subject" is meant herein a subject who does not suffer from acne, in particular acne vulgaris, and preferably who does not suffer from a C. acnes-associated disease, in particular skin disease and/or from an inflammatory disease and/or from a skin disease and more preferably who further does not present any sign of skin discomfort such as signs associated with sensitive skin, sensitized skin, fragile skin or weakened skin, or any uncomfortable and unaesthetic manifestations of sensitized, fragile and/or weakened skin.

By "sensitive skin" is meant herein a skin which, by nature, does not tolerate aggressive agents well, especially environmental agents such as pollutants, climate factors (wind, cold, heat), emotional factors, especially stress and/or chemical agents (heavy metals, detergents, compounds contained in cosmetic compositions such as fragrances, preservatives, alcohols, pH, AHA or dermatological treatments, such as vitamin A acid) and/or aggressive conditions, including perspiration and mechanical aggression such as waxing, shaving, rubbing and even water, especially hard water. Sensitive skin is not pathological skin, unlike allergic skin. Nevertheless, it may react to aggressive agents and/or conditions by unaesthetic and/or uncomfortable cutaneous manifestations such as stinging, feeling of heat or warmth, tension, tingling, tightness and redness. Thus the "sensitive skin" character may be estimated by the subject themselves with subjective cutaneous sensations or by the dermatologist with objective cutaneous reactions.

By "sensitized skin" is meant herein a skin and/or mucosa momentarily made sensitive, as defined above, therefore nonpathological as such.

By "fragile" and/or "weakened skin" (i.e. skin made momentarily fragile), is meant herein a skin whose barrier function is weakened. This may be linked to the status of the individual; elderly people and infants have more fragile skin, for example. This state may result from chemical or physical aggression (abrasion, rubbing for example).

The uncomfortable and unaesthetic manifestations of sensitized, fragile and/or weakened skin are the same as for sensitive skin, without these manifestations and/or skin conditions being considered to involve the prevention and/or treatment of a pathology.

Unless defined otherwise, all technical and scientific terms used herein have the same meaning as commonly understood by one of ordinary skills in the art to which this invention belongs.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

Although the invention has been described in conjunction with specific embodiments thereof, many alternatives, modifications and variations will be apparent to those skilled in the art. Accordingly, it is intended to embrace all such alternatives, modifications and variations to fall within the spirit and broad scope of the appended claims.

All publications, patents and patent applications mentioned in this specification are herein incorporated in their entirety by reference into the specification, to the same extent as if such individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The following examples are given for the purpose of illustrating various embodiments of the invention and are not meant to limit the present invention in any fashion.

| BRIEF DESCRIPTION OF THE SEQUENCES | | | |
|---|---|---|---|
| SEQ ID NO: | Type | Organism | Description |
| 1 | Genomic DNA | C. acnes | hem locus sequence reference for α-type C. acnes bacteria |
| 2 | Genomic DNA | C. acnes | hem locus sequence reference for β-type C. acnes bacteria |
| 3 | Genomic DNA | C. acnes | hemA gene sequence reference |
| 4 | Genomic DNA | C. acnes | hemB gene sequence reference |
| 5 | Genomic DNA | C. acnes | hemC gene sequence reference |
| 6 | Genomic DNA | C. acnes | hemD gene sequence reference |
| 7 | Genomic DNA | C. acnes | hemE gene sequence reference |
| 8 | Genomic DNA | C. acnes | hemH gene sequence reference |
| 9 | Genomic DNA | C. acnes | hemL gene sequence reference |
| 10 | Genomic DNA | C. acnes | hemY gene sequence reference |

-continued

BRIEF DESCRIPTION OF THE SEQUENCES

| SEQ ID NO: | Type | Organism | Description |
|---|---|---|---|
| 11 | Artificial sequence | | Mad4 nuclease |
| 12 | Artificial sequence | | non-targeting gRNA |
| 13 | Artificial sequence | | IA1 gRNA |
| 14 | Artificial sequence | | HemB_1 gRNA |
| 15 | Artificial sequence | | HemL_2 gRNA |
| 16 | Artificial sequence | | HemY_2 gRNA |

BRIEF DESCRIPTION OF THE FIGURES

FIG. 2: Published porphyrin production levels along with their assigned a/R3 type and the deoR repressor presence (deoR+) or absence (deoR−).

FIG. 3: Extract of the alignment of the glpR/deoR reference DNA sequence (SEQ ID NO:17 encoding SEQ ID NO:18) with the consensus glpR/deoR DNA sequence for most strains of the SLST D cluster (SEQ ID NO:19 encoding SEQ ID NO:20). Insertion of poly-G in the SLST D variant DNA sequence leads to a frameshift and the generation of a premature stop codon at position 105 whereas GlpR/DeoR reference protein is 310 AA long.

EXAMPLES

Example 1

Figure 1:
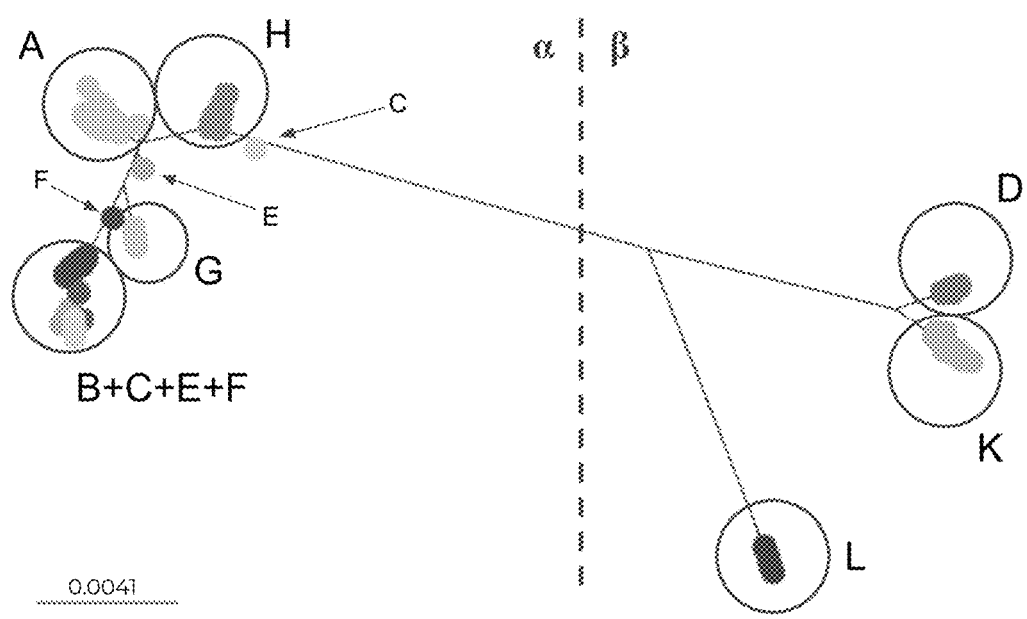
FIG. 1: Phylogenetic tree of the hem locus with annotated SLST clusters and the a/R3 typing division herein disclosed.

Heme molecule, a porphyrin ring complexed with iron, is an enzymatic cofactor and a source of iron essential for survival of bacterial pathogens (Choby et al. (2016) J. Mol. Biol. 428:3408-3428). *Cutibacterium acnes* (hereinafter *C. acnes*) is the most abundant bacteria inhabiting human skin (Fitz-Gibbon et al. (2013) J. Invest. Dermatol. 133:2152-2160, Oh et al (2014) Nature 515-59-64). It is also known to be involved in acne vulgaris, an inflammatory skin disease affecting the vast majority of adolescents and young adults (Bhate et al. (2013) British Journal of Dermatology 168:474-485). *C. acnes* has been shown to produce porphyrins that trigger inflammation (Schaller et al. (2005) British J Dermatol. 153:66-71, Spittaels et al. (2021) iScience 24:102575). Interestingly, *C. acnes* strains from different lineages vary in their porphyrin production levels (Johnson et al. (2016) mSphere 1:e00023-15, Barnard et al. (2020) mSphere 5:e00793-19), and the presence of a putative repressor gene from the deoR family has previously been hypothesized to be responsible for low levels of porphyrin production (Johnson et al. (2016) mSphere 1:e00023-15). However, such explanation is not complete, as high levels of porphyrin production were observed also for some strains which encode for deoR in their genomes (Barnard et al. (2020) mSphere 5:e00793-19). Moreover, while the lineage of the strains is usually indicative of their low/high porphyrin production, exceptions have been described in the literature (Johnson et al. (2016) mS phere 1:e00023-15).

Key enzymes involved in the porphyrin biosynthesis pathway in *C. acnes* are encoded by 8 genes (hemA, hemB, hemC, hemD, hemE, hemH, hemL, hemY). Those genes are clustered in a locus (hereafter referred to as the hem locus) that is conserved across all *C. acnes* strains.

The inventors found that a set of 218 SNPs across the hem locus genes can separate the known *C. acnes* strain diversity in two groups, α-type and β-type. While the inventors can unambiguously assign types from classical *C. acnes* typing schemes (SLST, recA) to either the α- or β-type, a and β-types are not monophyletic based on the core genome phylogeny (i.e. overall similarity of the strain genomes does not predict whether the strain will be a or P). Importantly, a/p typing strictly correlates with presence/absence with the published porphyrin production levels, with α-type strains being high producers and β-type strains low producers.

Furthermore, the inventors have developed a method for the estimation of relative abundances of a and β-type *C. acnes* strains in shotgun metagenomic sequencing data, and applied it to a public dataset associated to a study characterizing the skin microbiome in acne vulgaris (Barnard et al. (2016) Scientific Reports 6:39491). They found α-type strains to form a significantly larger fraction of the *C. acnes* population in acne vulgaris patients than in healthy volunteers. Therefore a treatment modality to specifically kill α-type *C. acnes* strains, inhibit specifically the growth of α-type *C. acnes* strains or inactivate porphyrin production in *C. acnes* α-type strains has the potential to prevent and/or cure acne vulgaris.

SLST Cluster Definition

The genomic assembly of 475 *C. acnes* strains were either sequenced by Eligo Bioscience or downloaded from public repositories. For each assembly, the single-locus sequence type (SLST) was predicted using in silico P C R amplification and sequence alignment with the primers and reference sequences described by Scholz et al. (Scholz et al. (2014) PloS ONE 9:e104199). A pangenomic analysis of the whole collection was also performed using roary (Page et al. (2015) Bioinformatics 31:3691-3693) and panX (Ding et al. (2018) Nucleic Acids Res. 46:e5), and a phylogenetic tree based on the core genome was built using RAxML (Stamatakis (2014) Bioinformatics 30:1312-1313). Based on the branch lengths of the core genome phylogenetic tree, the inventors defined a coarser typing scheme, SLST cluster, consisting in the grouping of SLST types starting with the same letter (e.g. SLST cluster A includes SLST A1, A2, etc.).

α and β-type definition

The hem locus genes were extracted from all available assemblies and a phylogenetic tree was built based on their concatenated amino acid sequences using IQ-TREE (Minh et al. (2020) Mol. Biol. Evol. 37:1530-1534) with edge-equal partition model (Chernomor et al. (2016) Syst. Biol. 65:997-1008) and revised Dayhoff matrix substitution model (Kosiol et al. (2005) Mol Biol Evol 22:193-199). In the obtained tree (FIG. 1) the inventors observed two distinct groups that do not match the core genome phylogeny —one comprising SLST clusters A, B, C, E, F, G, and H (named the α-type) and the other comprising SLST clusters D, K and L (named the β-type). Importantly, no SLST cluster was split between the types.

In order to obtain a set of marker S N P s for those types, the inventors computed a multiple sequence alignment on the nucleotide level for each gene with MUSCLE (Edgar (2004) Nucleic Acids Res 32:1792-1797) and identified positions that discriminate between the α- and the β-type, while being conserved in more than 90% of the genomes from each type. This procedure identified 218 marker positions (see Table 1 above). Based on this result, the inventors defined the α-type (and the β-type) as strains that in at least 90% of said positions have the α-characteristic (or the β-characteristic) nucleotide variants.

Analysis of Published Porphyrin Levels

Available scientific literature was searched for reported levels of porphyrin production by *C. acnes* strains. Data from two articles (Johnson et al. (2016) mSphere 1:e00023-15, Barnard et al. (2020) mSphere 5:e00793-19) were aggregated, and the strains used were typed using the available genome sequences and the SLST scheme. In cases when genomic sequences were notavailable, SLST clusters were inferred from the lineages reported by the authors.

Figure 2A:
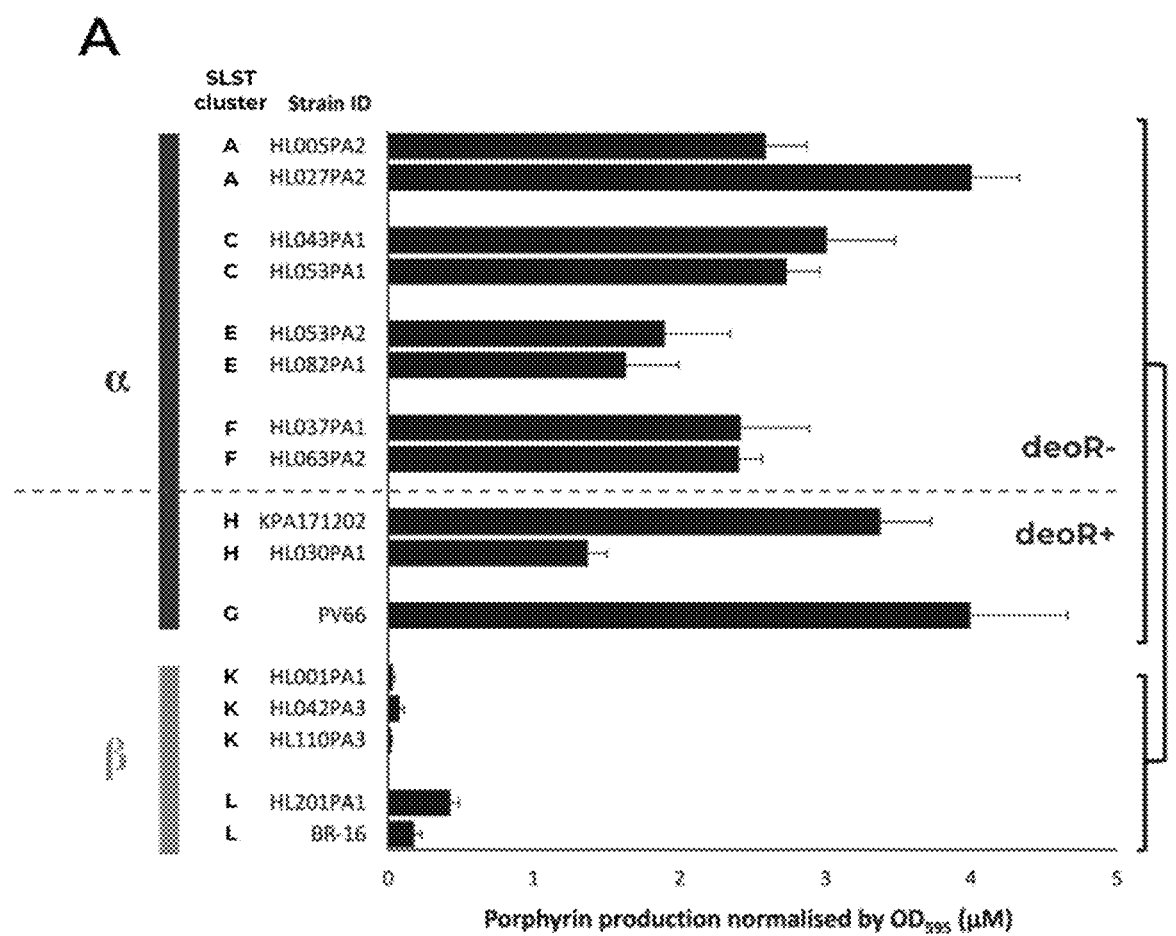
FIG. 2A: Adapted from FIG. 1 of Barnard et al. (2020) mS phere 5:e00793-19.
Figure 2B:
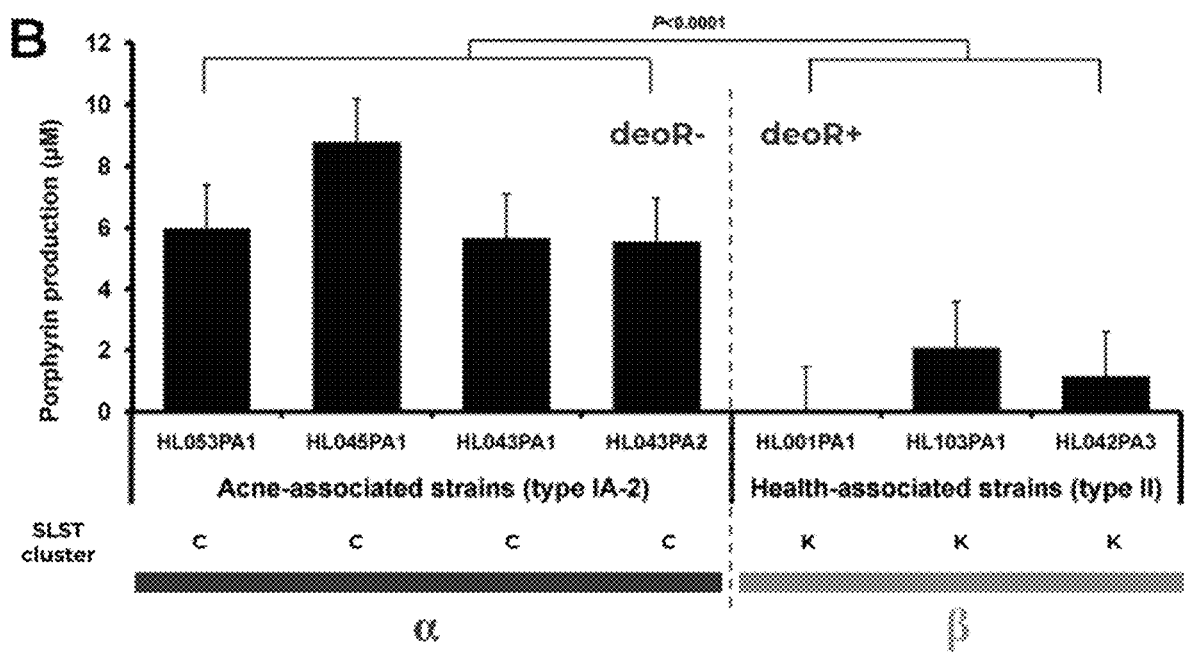
FIG. 2B: Adapted from FIG. 1 of Johnson et al. (2016) mSphere 1(1):e00023-15.
Figure 2C:
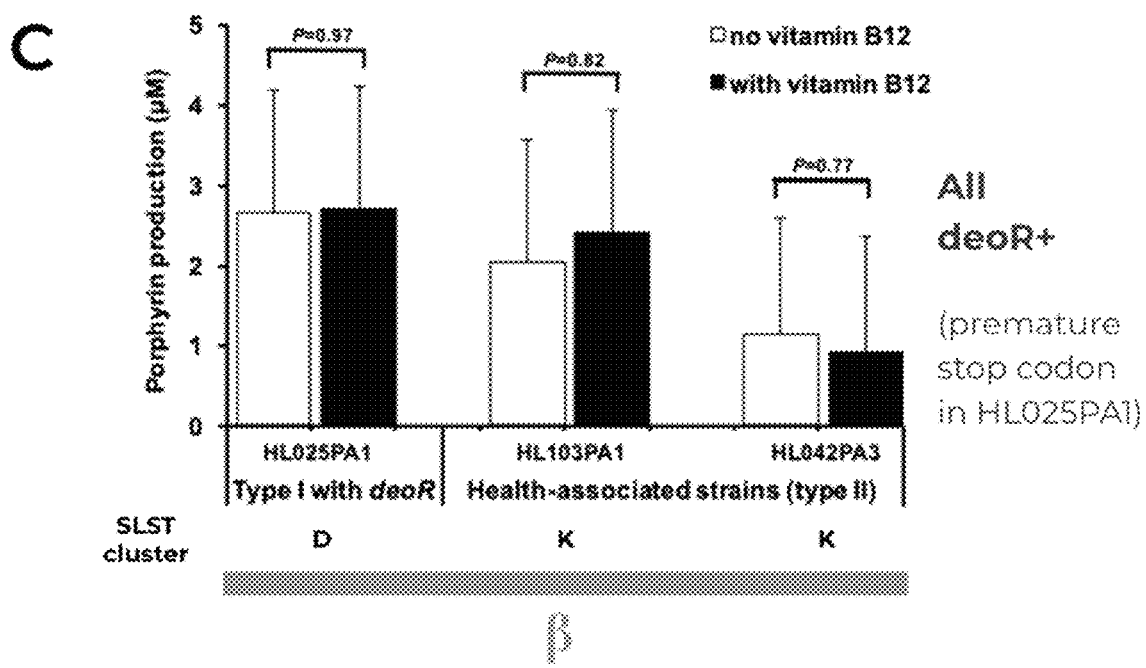
FIG. 2C: Adapted from FIG. S4 of Johnson et al. (2016) mSphere 1(1):e00023-15.
Figure 3:
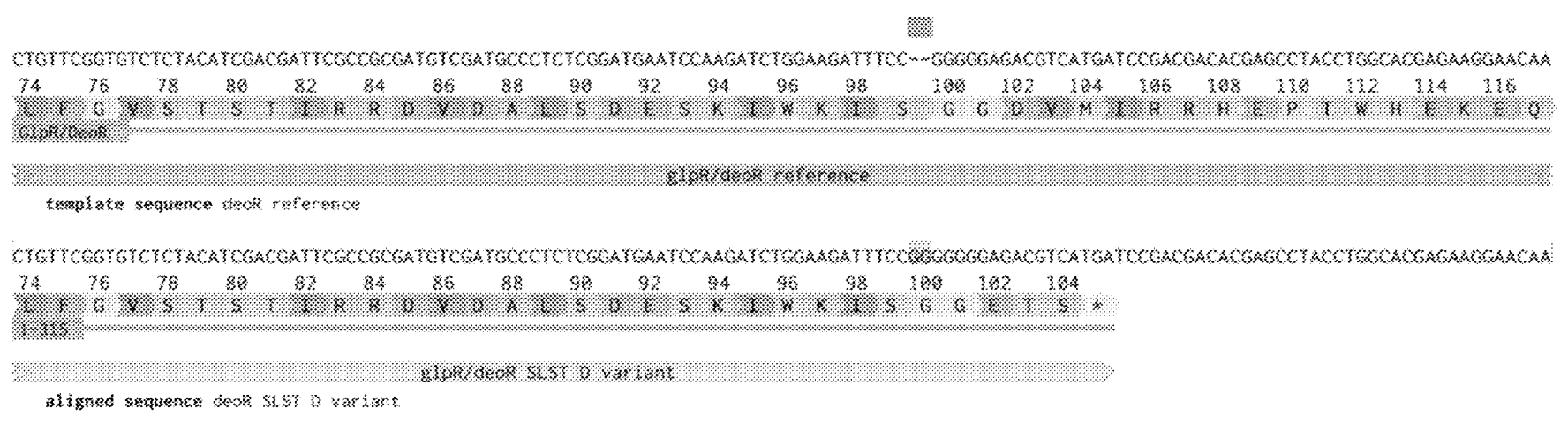

Based on the SLST clusters, the strains were assigned to either α- or β-type. The inventors observed that the strains classified as high or low porphyrin producers by the authors exactly correspond to α- and β-type strains (FIG. 2), respectively, offering a more reliable explanation of the production levels than the presence of the deoR repressor. Moreover, by multiple sequence alignment of the deoR genes the inventors found that the SLST cluster D strains bear a poly-G insertion in this gene, which results in a shifted reading frame and a nonsense mutation in the majority of the cases, HL025PA1 included (FIG. 3). It is therefore expected that deoR in SLST cluster D is not functional and cannot explain the low porphyrin production measured. Therefore, the inventors considered the SNPs in Table 1 above to be biomarkers for high porphyrin production (α-type). Inversely, β-type is associated with low porphyrin production.

Metagenomic Analysis

Metagenomic shotgun sequencing data from Barnard et al. (2016) Scientific Reports 6:39491, including follicular plugs samples from 42 acne vulgaris patients and 40 healthy volunteers, were obtained from the NCBI dbGaP resource (accession number phs001655). Raw reads were pre-processed using fastp (Chen et al. (2018) Bioinformatics 34:i884-i890) and aligned against the human reference genome and the PhiX genome using bowtie2 (Langmead et al. (2012) Nature Methods 9:357-359). The reads aligning to either the host or PhiX were removed, while those passing QC were mapped to the reference hem locus using bwa mem (Li (2013) arXiv:1303.3997) and only properly paired mappings were kept for downstream analysis.

Since the locus is always single-copy in the available *C. acnes* genomes and does not have close orthologues in other species (the closest one, in *Cutibacterium modestum*, has 86% identity at the nucleotide level), the inventors did not include other reference sequences in the alignment database. However, in order to validate their approach, they also used Kraken2 (Wood et al. (2019) Genome Biology 20:257) to remove reads assigned to other species than *C. acnes* from the dataset, observing no difference in our results.

Figure 4:
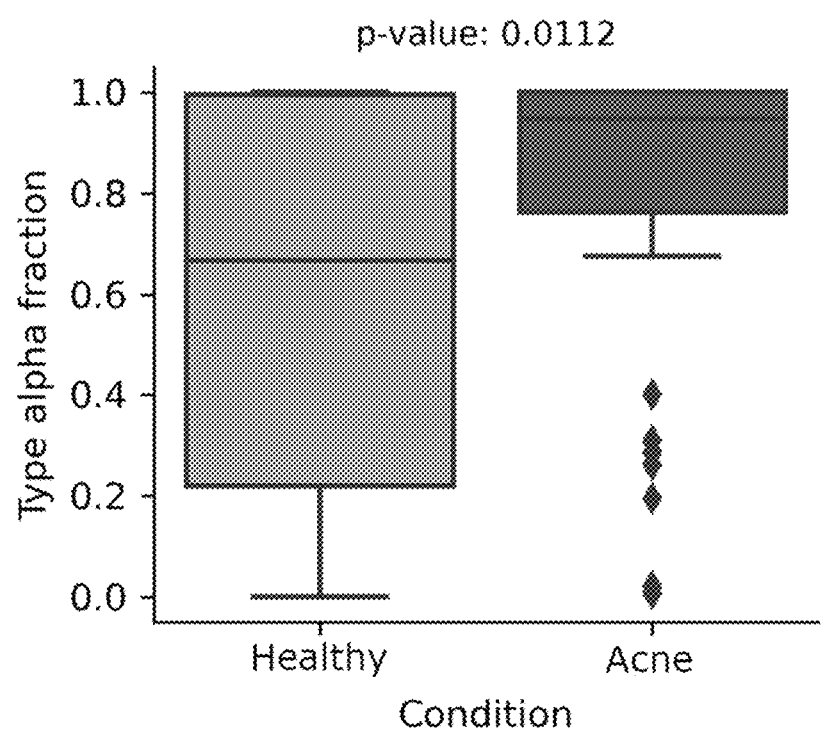
FIG. 4: Difference between ratio of *C. acnes* population classified as the α-type in healthy skin metagenomes and the skin metagenomes of patients with acne vulgaris
Figure 5:
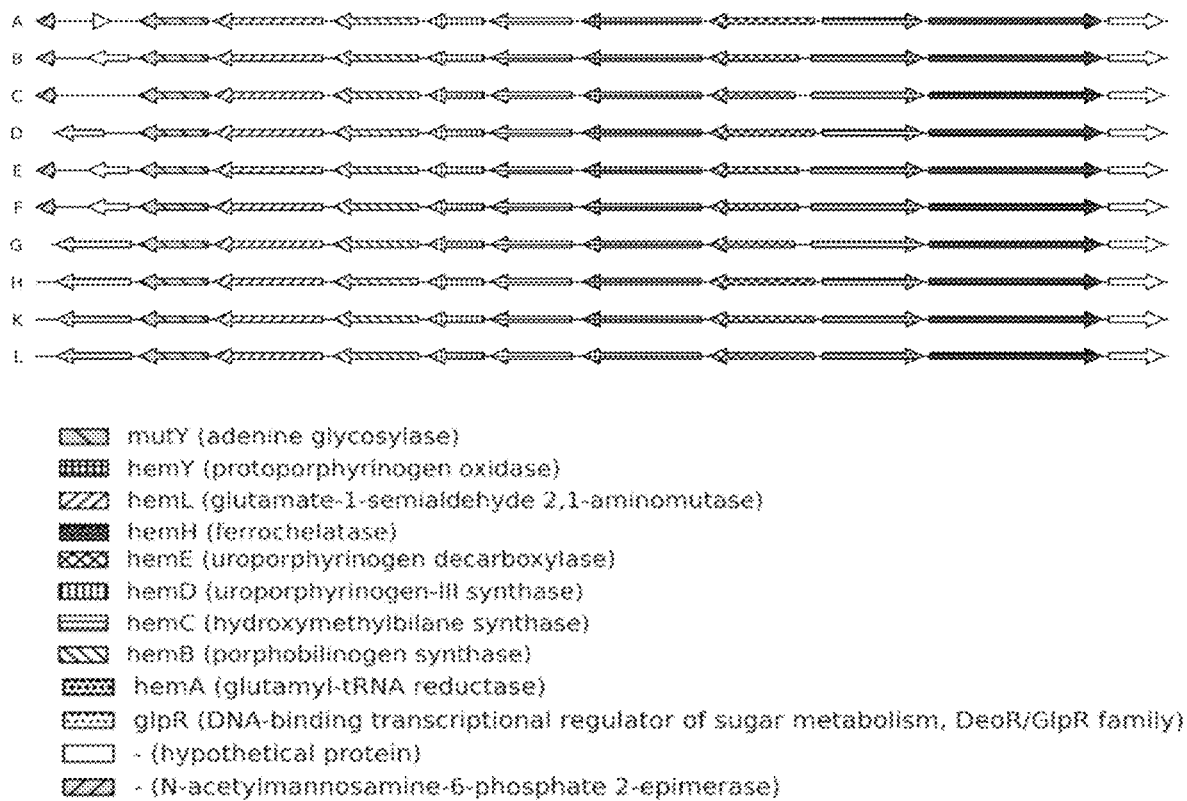
FIG. 5: The hem locus that is conserved across *C. acnes* strains and which comprises 8 hem genes: hemA, hemB, hemC, hemD, hemE, hemH, hemL and hemY. A representative from each SLST cluster is shown.

For each of the 218 discriminative positions, the fraction of α-type and β-type variants was computed from the alignment pileup. The overall relative abundance of each type within the *C. acnes* population was calculated using the median frequency of its signature SNPs across the 218 positions. Type a was found to be significantly more abundant in the *acnes* vulgaris patients than in the healthy controls (p-value 0.0112; Mann-Whitney U test) (FIG. 4).

Example 2

Figure 6A:
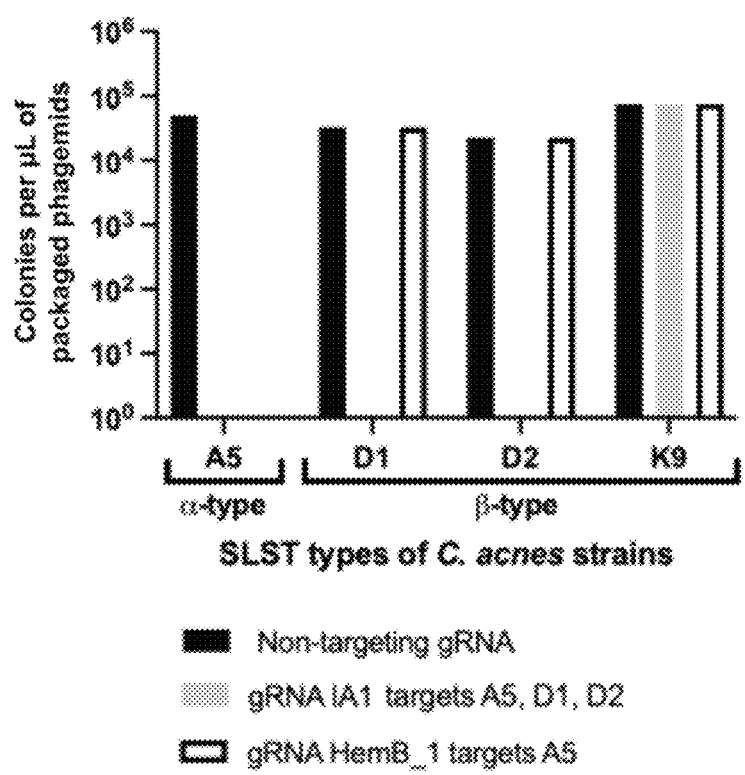
FIG. 6: Specific nuclease-mediated killing of alpha-type *C. acnes* strains. A) Specific nuclease-mediated killing of *C. acnes* phylotypes and alpha vs beta strains. Each diluted population of four *C. acnes* strains (one alpha-type strain: SLST A5; three beta-type strains: SLST D1, D2, K9) was transduced with three different packaged phagemids, each packaged with a DNA payload carrying a chloramphenicol cassette, a nuclease (SEQ ID NO: 11) expression cassette and either a non-targeting gRNA (SEQ ID NO: 12, black bars), or a gRNA that targets the strains A5, D1, D2 (SEQ ID NO: 13, grey bars), or a HemB gRNA that targets only the strain SLST A5 (SEQ ID NO: 14, white bars). Y axis: Colony-forming units (cfu) per µL of packaged phagemid on BHI+3 µg/mL chloramphenicol plates. B) Specific nuclease-mediated killing of *C. acnes* alpha strains vs beta strains. Each diluted population of four *C. acnes* strains (three alpha-type strains: 2× SLST A1, SLST A5; one beta-type strain: SLST K9) was transduced with six different packaged phagemids, each packaged with a DNA payload carrying a chloramphenicol cassette, a nuclease (SEQ ID NO: 11) expression cassette as well as a non-targeting gRNA (SEQ ID NO: 12) or a set of Hem gRNAs that target the three alpha-type strains at different positions of the hem locus: HemB_1 gRNA (SEQ ID NO: 14) targets HemB alpha nucleotide variant A155; HemL_2 gRNA (SEQ ID No.: 15) targets HemL alpha nucleotide variants C389 and T392; HemY_2 gRNA (SEQ ID No: 16) targets HemY alpha nucleotide variants T1199 and T1205. Y axis: Colony-forming units per µL of packaged phagemids on BHI+3 µg/mL chloramphenicol plates.

Specific Nuclease-Mediated Killing of *C. acnes* Phylotypes and Alpha Vs Beta Strains This example demonstrates the nuclease-mediated specific killing of *Cutibacterium acnes* phylotypes as well as alpha strains vs. beta strains. The nuclease can be programmed to target and kill specific phylotypes (in this example, phylotypes IA1 and II) that encompass both alpha and beta strains according to the definition in the section "α-type *C. acnes* bacteria and β-type *C. acnes* bacteria" above (FIG. 6A). Similarly, the nuclease can be programmed to target and kill only alpha strains while leaving beta strains intact (FIG. 6 B).

Four *C. acnes* strains (one alpha-type strain: SLST A5; three beta-type strains: SLST D1, D2, K9) were grown anaerobically overnight at 37° C. and diluted the following day to an OD600 of 0.05. Strains SLST A5, SLST D1 and SLST D2 belong to phylotype IA1. SLST K9 belongs to phylotype II. Each diluted *C. acnes* population was transduced with three different packaged phagemids, each packaged with a DNA payload carrying a chloramphenicol cassette, a Mad4 nuclease (SEQ ID NO: 11) expression cassette and either a non-targeting gRNA (SEQ ID NO: 12), or a gRNA that targets phylotypes IA1, i.e. the strains A5, D1, D2 (SEQ ID NO: 13), or a HemB gRNA (HemB_1 gRNA) that targets HemB alpha nucleotide variant A155 and thus only alpha-type *C. acnes* strains such as the strain SLST A5 (SEQ ID NO: 14) Transduced cells were serially diluted and plated on BHI agar with 3 μg ml-1 chloramphenicol post transduction and incubated in an anaerobic chamber at 37° C.

As shown in FIG. 6A, packaged phagemids programmed with a HemB_1 gRNA that targets HemB alpha nucleotide variant A155 selectively reduced the number of the alpha-type strain (SLST A5) by more than 4 logs while not affecting the growth of any of the beta-type strains (SLST D1, D2 and K9). Packaged phagemids programmed with a IA1 gRNA selectively reduced the number of colonies from the strains SLST A5, D1, D2 by more than 104 fold while not affecting the number of colonies from the strain SLST K9, as anticipated.

Specific Nuclease-Mediated Killing of C. acnes Alpha Strains Vs Beta Strains

Four C. acnes strains (three alpha-type strains: 2× SLST A1, SLST A5; one beta-type strain: SLST K9) were grown anaerobically overnight at 37° C. and diluted the following day to an OD600 of 0.05. E ach diluted C. acnes population was transduced with six different packaged phagemids, each packaged with a DNA payload carrying a chloramphenicol cassette, a Mad4 nuclease (SEQ ID NO: 11) expression cassette as well as a non-targeting gRNA (SEQ ID NO: 12) or a set of Hem gRNAs that target the three alpha-type strains at different positions of the hem locus: HemB_1 gRNA (SEQ ID NO: 14) targets HemB alpha nucleotide variant A155; HemL_2 gRNA (SEQ ID No.: 15) targets HemL alpha nucleotide variants C389 and T392; HemY_2 gRNA (SEQ ID No: 16) targets HemY alpha nucleotide variantsT1199 and T1205. Transduced cells were serially diluted and plated on BHI agar with 3 μg ml-1 chloramphenicol post transduction. Plates were incubated in an anaerobic chamber at 37° C.

Figure 6B:
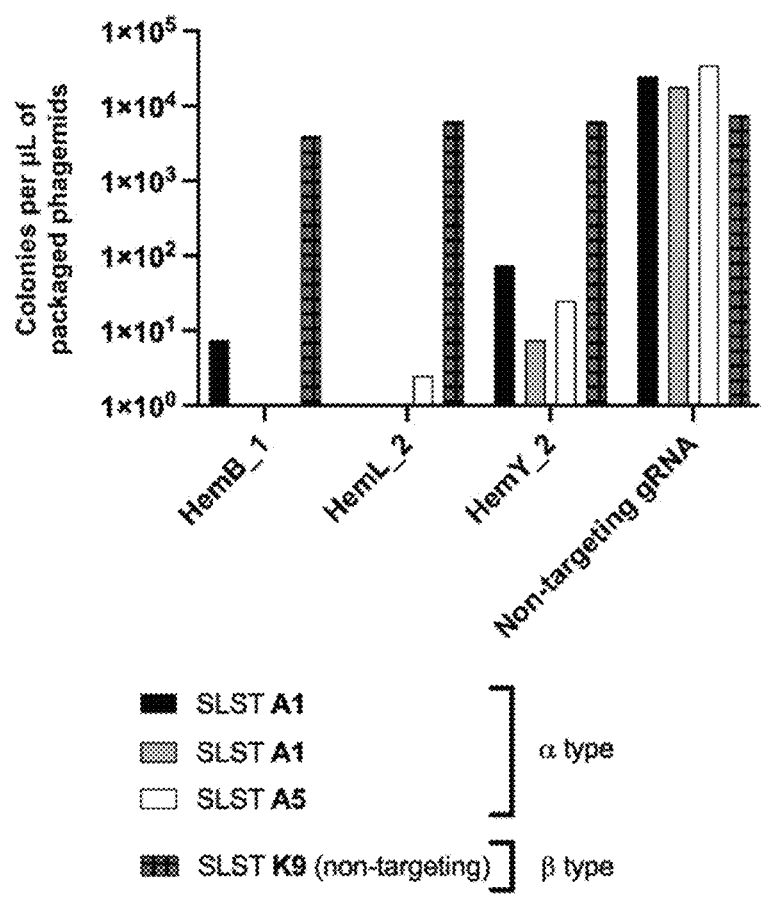

As shown in FIG. 6B, packaged phagemids programmed with a Hem gRNA that targets an alpha nucleotide variant, selectively reduced the number of the three alpha-type strains by more than 99.9% while not affecting the number of colonies from the beta-type strain.

I claim:

1. A method for treating a *Cutibacterium acnes* bacteria-associated disease in a subject, said method comprising reducing the ratio of the amount of α-type *C. acnes* bacteria to the amount of β-type *C. acnes* bacteria in the subject by administering to the subject a nucleic acid encoding a programmable nuclease, prime editor, or base editor designed to specifically target said α-type *C. acnes* bacteria at a nucleotide selected from one of the following nucleotide variants in the hem locus:

in the hemA gene: T173, A479, T506, A614, T629, C671, T971, A989, T1085, and T1094, wherein the positions are defined with reference to sequence SEQ ID NO: 3 and wherein the first nucleotide in the sequence is indexed as 0, in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4 and wherein the first nucleotide in the sequence is indexed as 0, in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, C897, G902, G908, A941, and A947, wherein the positions are defined with reference to sequence SEQ ID NO: 5 and wherein the first nucleotide in the sequence is indexed as 0, in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6 and wherein the first nucleotide in the sequence is indexed as 0, in the hemE gene: T241, T476, A530, T704, A728, G767, T834, A867, A872, A882, and A957, wherein the positions are defined with reference to sequence SEQ ID NO: 7 and wherein the first nucleotide in the sequence is indexed as 0, in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8 and wherein the first nucleotide in the sequence is indexed as 0, in the hemL gene: T107, C197, T229, A242, C310, A338, A374, T389, G392, T442, C467, G470, C482, G518, and C641, wherein the positions are defined with reference to sequence SEQ ID NO: 9 and wherein the first nucleotide in the sequence is indexed as 0, and in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10 and wherein the first nucleotide in the sequence is indexed as 0, wherein the nucleic acid sequence of the hem locus is at least 97% identical to the sequence SEQ ID NO: 1; and wherein β-type *C. acnes* bacteria are *C. acnes* bacteria which are not α-type *C. acnes* bacteria.

2. The method according to claim 1, wherein said method comprises specifically reducing the amount of α-type *C. acnes* bacteria on the skin of said subject.

3. The method according to claim 1, wherein said method comprises administering to said subject a therapeutically effective amount of a phage, recombinant phage, packaged phagemid, plasmid, DNA- or RNA-containing vesicle, or engineered bacteria comprising said nucleic acid encoding a programmable nuclease, prime editor, or a base editor designed to specifically target said α-type *C. acnes* bacteria.

4. The method according to claim 3, wherein said programmable nuclease is selected from the group consisting of CRISPR-Cas nucleases, TALENs, zinc finger nucleases, and engineered meganuclease.

5. The method according to claim 4, wherein said programmable nuclease is a CRISPR-Cas nuclease.

6. The method according to claim 5, wherein said phage, recombinant phage, packaged phagemid, plasmid, DNA- or RNA-containing vesicle, or engineered bacteria, further encodes a guide RNA designed to specifically target said α-type *C. acnes* bacteria.

7. The method according to claim 6, wherein said guide RNA is designed to specifically target the hem locus of said α-type *C. acnes* bacteria selected from the group consisting of SEQ ID Nos: 13-16.

8. The method according to claim 3, wherein said administration is a topical administration.

9. The method according to claim 1, wherein said nucleic acid encodes a base editor or a prime editor.

10. The method according to claim 1, wherein said method comprises increasing the amount of β-type *C. acnes* bacteria in said subject on the skin of said subject.

11. The method according to claim 1, wherein said *C. acnes* bacteria-associated disease is a *C. acnes* bacteria-associated inflammatory disease.

12. The method according to claim 1, wherein said *C. acnes* bacteria-associated disease is acne vulgaris.

13. A method for treating a *C. acnes* bacteria-associated disease in a subject, said method comprising specifically reducing the expression of at least one hem locus protein in α-type *C. acnes* bacteria in said subject by administering to said subject a nucleic acid encoding a programmable nuclease, prime editor, or base editor designed to specifically target said α-type *C. acnes* bacteria at a nucleotide selected from one
of the following nucleotide variants in the hem locus:
in the hemA gene: T173, A479, T506, A614, T629, C671, T971, A989, T1085, and T1094, wherein the positions are defined with reference to sequence SEQ ID NO: 3 and wherein the first nucleotide in the sequence is indexed as 0,
in the hemB gene: C142, A155, A176, A183, C224, C245, G248, T281, G311, C314, T346, C374, G377, C452, T626, C683, A693, A720, C738, C794, A920, T944, T992, G1022, and T1031, wherein the positions are defined with reference to sequence SEQ ID NO: 4 and wherein the first nucleotide in the sequence is indexed as 0,
in the hemC gene: G77, A96, C149, A233, T236, T255, A257, A260, C317, A347, T425, T437, A464, A486, A487, C488, A524, A545, A590, T605, A644, A665, C710, C713, A737, A770, A776, T785, T802, G830, C842, T845, G855, C893, A896, A897, G902, G908, A941, and A947, wherein the positions are defined with reference to sequence SEQ ID NO: 5 and wherein the first nucleotide in the sequence is indexed as 0,
in the hemD gene: T11, T41, T50, A150, T155, G159, G176, T257, C266, T278, G323, A324, T362, T367, T374, G387, A398, A399, T407, G422, G425, G432, A446, A459, T464, G595, T617, T643, A644, and C680, wherein the positions are defined with reference to sequence SEQ ID NO: 6 and wherein the first nucleotide in the sequence is indexed as 0,
in the hemE gene: T241, T476, A530, T704, A728, G767, T834, A867, A872, A882, and A957, wherein the positions are defined with reference to sequence SEQ ID NO: 7 and wherein the first nucleotide in the sequence is indexed as 0,
in the hemH gene: T11, T23, A48, T89, C188, G338, T464, T470, G536, T548, T608, G626, T632, T641, T671, T674, C683, C689, A740, G745, G787, A797, T893, A898, T1034, T1039, T1046, C1071, G1095, C1109, T1153, T1358, G1496, C1511, C1527, G1532, T1598, T1712, A1850, G1901, A1926, C1931, and C1997, wherein the positions are defined with reference to sequence SEQ ID NO: 8 and wherein the first nucleotide in the sequence is indexed as 0,
in the hemL gene: T107, C197, T229, A242, C310, A338, A374, T389, G392, T442, C467, G470, C482, G518, and C641, wherein the positions are defined with reference to sequence SEQ ID NO: 9 and wherein the first nucleotide in the sequence is indexed as 0, and
in the hemY gene: A89, A236, A354, C383, C392, A395, T398, T465, T474, C521, T538, C566, A593, A767, T782, G863, G920, T927, A932, G935, C979, G989, C1019, T1055, G1091, T1136, G1143, G1152, T1166, T1172, A1176, T1184, C1199, C1205, G1268, G1278, T1295, T1318, A1336, G1343, C1346, G1355, T1359 and C1395, wherein the positions are defined with reference to sequence SEQ ID NO: 10 and wherein the first nucleotide in the sequence is indexed as 0,
wherein the nucleic acid sequence of the hem locus is at least 97% identical to the sequence SEQ ID NO: 1.

14. The method according to claim 1, wherein the programmable nuclease recognizes nucleotide variant A144 in the hemB gene.

15. The method according to claim 1, wherein the programmable nuclease recognizes nucleotide variants C389 and T392 in the hemL gene.

16. The method according to claim 1, wherein the programmable nuclease recognizes nucleotide variants T1199 and T1205 in the hemY gene.

17. The method according to claim 1, wherein the programmable nuclease recognizes nucleotide variant A144 in the hemB gene.

18. The method according to claim 13, wherein the programmable nuclease recognizes nucleotide variants C389 and T392 in the hemL gene.

19. The method according to claim 13, wherein the programmable nuclease recognizes nucleotide variants T1199 and T1205 in the hemY gene.

* * * * *

SEQUENCE LISTING

```
Sequence total quantity: 20
SEQ ID NO: 1              moltype = DNA  length = 10225
FEATURE                   Location/Qualifiers
source                    1..10225
                          mol_type = genomic DNA
                          note = Alpha type locus reference
                          organism = Cutibacterium acnes
SEQUENCE: 1
tcaggcactg atcacctggg aagccgcctg ggcagccttc ggcagggcgg cgcggaaaac    60
ctcgaaagct tcgtcgtcgt gagcgtcgga gaggaaccag gcctcaaagc acgatggcgg   120
caggttgacc ccggcatcta gcatcgcgtg gaagaacgcg gtgtaagcct cggcattctg   180
agacttggcg ttgtcgtaat tgcgcaccgg agagtcgacg ccgaggaata cgctgaagag   240
atttccggcg ttctgcaggc ggtacgtgac gccggctgcg tcaagcgcgg atacgagctc   300
actgcgccat ttctcagagc gcgcatcgag gcgctggtac accccggcgt cggccagctg   360
cagggttttg acacccgcga cggtggccag cgggttaccg gacaaagtgc cggcctggta   420
gacggggccg gtaggagcca gcaaatccat gacctcggcg cgcccaccta gggcagccag   480
cggcatacca ccgccgatga ccttgccgaa cgtgaaaata tcgggagcga agtcctcgcc   540
ggcctgctgt tgcaaacccc agaatcccga cgggctgcac cggaatccgg tgagtacttc   600
gtcggtgatc atgagggcac cgtgctcggt tgtgaggcga cgaatcgcgg cattgaagcc   660
gggttcgggg ggaacaactc ccatattggc cgggcaggac tccacgatca ctgcagcaat   720
ctggtcgcca cgctcggaga acatcgcgtc gagggcggcg acgtcgttgt aatccaccac   780
aatagtgtcg gccgtcgagg cggctggcac accgccgaa ccggcaggc cagccgtcgc    840
cacgccggaa ccggcggcgg cgagcaggac gtcagaatgg ccgtggtagt taccggcaaa   900
cttgacgatg acgtcacgcc cagtggtgcc acgggctaaa cggaccgcag tcattgtcgc   960
ctcagtgcct gttgagacga aacgcacctt ctcgaccgga gccatccgct cgatgatggc  1020
atccgctagt tcggtttcgg tgcgggtcgg ggcgccaaag gacagccctt tcgacgcggc  1080
cacctgaacc gcagagacga cctcgggacg ggcgtgccca agcaaagccg gaccccaggt  1140
gcacaccaga tcgacgtagc gcgtgccctc ggcgtccag atccacgggc cttgggcctt  1200
ctcaatgaag cgaggaaccc cgcccaccga gccgtaagcc cgcaccgggg aatcaaccc   1260
gccgggaatg acggcctggg cggcggagaa cagttcggcg ttgaggtca tttcttcctt   1320
ccggtgtggg ggtttgtggt gagcatgatc acgacgggtc agaggtcctc gcgaaacatc  1380
tgcgccgcct cgattgccca gtaggtcaag acaagatcgg caccggcacg cacgatcgag  1440
gtcagggact ctccgatgca acgtcggcga tcgatccaac cgtttgcggc agcggcctcg  1500
agcatggcgt attctccaga gacctggtaa gcggcaaccg gtacctgcga cacctcggcg  1560
acatcggaca cacgtcgag gtagtgggag gcgggcttca ccatgaccag gtcggctccc  1620
tcggcgaggt cgagaagggt ttcgcgcagg ccttcccggc ggttcggtgg atcctgctgg  1680
taagtcttgc gatcaccctt aaggaaaac ttgacggcgt cgcggaaggg gccaaagaag  1740
gctgaagcgt acttagctga ataggccatg atggacacat cggtgaatcc ctcgcgatcc  1800
agagcatcgc gaatgacagc gatctgaccg tccatcatcc ccgacgggga gaccatgtgg  1860
gctccggcgc gcgcttggga gaccgccatc gcggcatata gcggcacagt ggagtcatta  1920
tcgacgcgac catcagggtt cagagctccg cagtgtccat gatcggtgaa ctcgtctaga  1980
caggtgtcgg cacagatcac cagatcgtcg ccgacggcct cgcgcaccgc ggagatgccg  2040
gcgttgagga tgcctttcag gtcccaggcc tgagaaccga tctcgtcttt gtgctccggg  2100
ataccaaaca ggtcaatacc accaataccg gcctcggcag cttgggtggc gagctccttg  2160
atcgactcgg tggagtgctg gaattggccg ggcaggctgg tgatctcgac gggggaatcg  2220
atccctctt tgacgaaccgc cggcagcatt aactgggcgg gggcgacgcg ggttcggcg   2280
accatccggc gcatcgcagg agtggtgcgt agtcgacgcg gacgagaaac aggacgcagc  2340
ccctcggcca atggcttgac cccagccatg cggggatcac tggcatcagg caggtacggg  2400
ttcatgatca acttccttcg cgaacggccg tcggtcaggc gaccaaggac tcaaccgcct  2460
caaggacggc ttcaggagtg ggggaggagg ccaccgcatg cgctgggtga ccgagtactt  2520
cgagtgttct tgcagtgggc ttaccgaggg cgacgagctt ctgacgacgc catcccagcg  2580
gctctaccag ctcgacgagg gcacgtccca ccgaggaggc agtgacgacg acgacccga   2640
cagacggcca cgactgggcg atgacctcag gcagtttctc gacggcagcg gtggtataga  2700
tctccaatcg gtttaccgtg cagccgacct tcgtcagccc cagcggtacg gtatcggcgg  2760
ttaactggga cgctggtagg aggatactgg cgactccacc tggccactcg gcgaccagac  2820
```

```
cagcgccgct gtgattctcg gggacgaagt cgacgtcaat cccacgtgtg cgcagcgcag    2880
cagaggtagc ggcgccgacc gcagctactt tgatgttggg attcggcaac ggggtaggga    2940
gcagtccgac ggtggtcttc gaggtgacga ccagccagtc ggcctgccac aggtcagggg    3000
cagtaagcct ctccgcatcc ggcaaggtga cggtgcgcgt cagcgctgtg tggatcactc    3060
cataaccggc ctgcttcaaa gtcgtcacga atttgtcgtg ggagtcgtca cggggaacaa    3120
caactggggg cttgacgaga tcggcaggat ttgtggtcat cgagtgcttc ctgaagcttt    3180
gagatctgca acgtcggcgg caccatcgtc cagtaactct tcggcagccg tcaccccag    3240
cgtatgcgcc gccgccagcg ctggttcgac ctccgcgggt aattcgacgc tgacctgttc    3300
ccgaacggtg cgggaaccgt cgacagcagc cactacaaca tccagggtta acacttgtag    3360
ggattttccc gaaacaggct tgagttgagc taatgctccg atggggcag cgcacccgc    3420
ctctagatgg gagagcaccg cacgttcggc ggtggcggcc agcctggttc tgcggtcgtc    3480
aatccgtgcc agcgctttgg cgagcttgcc atgacgtgaa tcagcggtcc ggcattcgac    3540
ggctagcgct ccctgagcag gggcaggcag tactaccgac gggtcgagga actcagtgac    3600
ggcgccgcta tgacctagtc gagctagtcc ggaggctgcg agcacgacgg cgtcgaggtc    3660
ctccttgcca ccgttttttgg cgtagcggcc gagtccctttg acgcgaccca gccgggtgtc    3720
gacatttcca cggatatcga cgatcgtcag gtccggtcta accgccaaca actgtgcggc    3780
ccgacgtggc gagcccgtcc cgacgctagc ttcttgcggg aggtcgtgaa gggtgagccc    3840
atcgcgggcc accaaagcgt cacgcgggtc cgctcgagct ggaacggcac cgatcgccag    3900
tcctaacgga cgtcctgtcg gtagatcttt gaaggagtgg acggcaatgt cggcttctcc    3960
ctcgaggagg gccgcacgga tcgccgaggc gaacacccg attcctccca tggccgctaa    4020
cgaggccgtc gaggtgtccc cgtgagtagt gatcgtcgtc agattgacgt ccagcccctc    4080
cgacctgagc agccccgcaa ccatctctga ttgagtagtg gccagagtgc tggcacgggt    4140
tcccagacgg atcgcagaca tattgcctat tgtggcactc agtaccgacg ccgattccag    4200
cctgcaatca gacaagttga cggacagttc ggcgggcctg cggcaccaga gcggcaatgc    4260
ccgaacccga tgcccacgac cccactaagc cgatccgtcc ctgtcagac tggttcaata    4320
cctctagctg gcggtgcaga ccatcgcgcc atgctcggtc gtcggtgcga    4380
gggaacctgt ccagtgaatg atctgggagt ctacgacctg ctccgccgag aggtccacgc    4440
cgagtaggac ggaagcgtcc gttagagcct gatcgacgct caaagcgaca ttcgcttcac    4500
cagatcgacc ataggaaacc cgtagcaagt ggagaccttc gggacacgat tctctcaagc    4560
tgggccactt cgccgacatg tgagtaagtg ccttggcagt aacggtggtc gttccgggag    4620
ccaccagcat gccgtttccg cgtgggctcg agtccagcgc gggtgcctgc aaggcgagat    4680
tgacgtggcc gatcggcgcg cccggtgcca actcggggcc aacggtgtcg atgacattgc    4740
tgagcagttt tgtggcaggt ccagccgaac aggccacgac gacccgaggg gtcaggaagg    4800
aacgaatctc gccgtcggtg acgggggggca aagatggatc cggattgcgg gaggtaccag    4860
cggtctccac tagccactga tctccgtggc gggttagccc tgctagcc actcgggtca    4920
tggtcgtcgc gccggcctgt tctgcctgac gacgcagctc ggccggcatg atgaacatgc    4980
caccggctac cgacgcgact gcaggccccg ctggcatccg tgagcggcac agcgcaactc    5040
ccgctgctag cgatccggtg gcctgggtgg cggccctcag accgggggag acgacgtcga    5100
ctgacagtag atgtgggtcg gcggcgttga ttccccccgg gatcggggtg acgagacgcc    5160
gcaatacctc tgaccccatc cgggaggcaa cgagcgtacc caggtcgcga gggagatcct    5220
caggcatggg tgcgcgatca agttcggcgg cgcgggcagc ctcttccgct cccagggcga    5280
tgatgacgac tgggtccgac aagttcgccg ggatgccaag aatggcatta tcgggcatcg    5340
cgaagcaggc gtcatcgaag tacacccaag acggggcgat ggtcggcttc tcaaccgtca    5400
atcccaactc ggtggccagt tcagcggtgt ctggtagacg gaccgcccac ccctcggccc    5460
cgatgtcgta gctgattccg gccagcgtcg acctggcaat cagcccgccg gtgtaccgc    5520
gggattcgac aagtaccggg tgcagacctt cctgggtgaa ctgccaggcg ccacgaggc    5580
cagccatgcc cccgccaatg acgacggcgt cgacgtcgtc cggatcagaa atgttcatcg    5640
tcgctactcg gctcacaggg agtgcaccag ctccaccagc cgtgtcaaga cgttgggtcc    5700
ggtgttggag ggcacaccgt gacccagatt gacgacgtgt ccaggggcct gacgtcctgc    5760
cgcgacgata tcgcgggtgg cggactccag cggttcccat ccggcaaaga gcaaggcggg    5820
atcgatgttg ccctgaaccg gcatctccat cccggagacc ataagagtgg cgcaggcctc    5880
atcaaggcta gtccggtggt cgacaccaag tactgggtac cgtgacgcag tagctgccac    5940
ctgcgcaaac tcagatagca gatgggtggc attgatgcca aagtgaacca ccgggatgtt    6000
cggatcgacg gtagccagag cccgctgaga gaaaggtgcg acgctggctc tataatcgct    6060
tgcgctcagc gacccagccc aggaatcaaa gagctgaag gcacgcgcc cgccgcgcag    6120
ctgagcagcc aggaaggcag catccaagtc ggcaacccac tccatcagcc ttgcccaggt    6180
ctgtgggtct gagtgcatca tcgctcgggc agacagatgg tcgcgggaag ggccgccctc    6240
gacgaggtag gcgcgatag taaacggggc accgcgaaa ccgatgagcg gtgtggcgtc    6300
gcctaactcg gtgatcgcca ggcgtggcagc ctcctcgata accgaggggt cctcgacatg    6360
acgtcgagta atgcggtcaa cgtcggaggc agtgcggacg ggttcgtcga gaacgggccc    6420
gactcctggc tcaatgcgca cctctgcccc cgccagagct agcggcacca tgatgtcgga    6480
gtagagaacg gccccgtcga cgtggtgcg gcgcacaggt tggcaggtaa tctcggcggc    6540
gagctcaggg ttgaggcaag actcgagcat cgtggtgccc tctcgggctt cgcggtactc    6600
cggtagcgaa cggcctgcct ggcgcataaa ccacaccggg gcaggtag ggcggtcgtc    6660
agtcatggct tgcagaagcg gtgaatctgc catgaaggta gtggtctcag tcatcacccc    6720
gattgtgccc taccacgtgc agatgccgcc cacaggacgg ttattgggcg agttatgagc    6780
ttagtatgta ctgggggttcg tcgttacagc atggttgaat aaggcttcgt gggattgtgt    6840
gtcttgaccg tggatcatgc cgagcagggg cttggcgtcg tttccgaggc ggccgcgcag    6900
gttgacggac ttggcctggc attgaccgat catcccccaga tccgggtcgc cctttgtgctg    6960
tcaacgtgca accgggtgtg cctgatcgtt gaaacctccc ctgaagccgt cgcgcaaggg    7020
ttcgacgagg ccgcgttacg caggtgcatt gccgatcacg gagcaaacgt gttagctgaa    7080
tctgcccagc tcgtctgtga aacgacgcc gtttggcgtt tgttccgtgt ggctgcgggc    7140
atggagtcga tggttttgg ggaacgtgag gtcgccggac agatgaagcg tgctctcagt    7200
gaggcgcgcc gtgaacgac cgtctcctac accattggtc acgtcgttga ggaagctctc    7260
aagacgtcac gtcatgtcgc taccgagact gcgttggctg ctgagggacg caccgttgtc    7320
gcggtcgggc ttgaccctcgt tgcccagcgg atggacttgg atggcgctcg ggtgctcgtt    7380
atggggactg gctcctatgc cggtgcgtcg tgcgcccagc tgagttctcg gggagtcgcc    7440
gagattcaag tccattcagc ttccggacgt gccgccggat tcgctcgacg ccaccgggtc    7500
agtgaggctc tcgacatcga cgccgcgctg gcacaagctg atcttgtcgt cacctgccgt    7560
```

```
gggtcgggag ttcctgcgtt gtctgctgag gctgctcggc gcgcggtcga cgctcgaagg  7620
ggccgcgatc tcatggtgct cgatttagca atcagcgggg acgttgagga gcctgtcccc  7680
gctggggtag aggtcatcga ccttgagacg atccggcagg ctgttccgc ctctgcggaa   7740
gctgagcggg ccgccgccga acacatcatc gctacgggag tccgtcactt tgccgtagac  7800
ctcgaacgtc gtcggatggc cccggctgtc gtcgctctgc gcgacgtcat ttcagatctc  7860
gttactgctg aactggagcg tctgcccgaa gaaggctcgg tccctgtcta tgaggtagcg  7920
gcgtctcttc gacgactcgc tgcatctatg gcgcacatcc cgtcggctcg agccaggatg  7980
gcctctgagc agggcttggg cgatcgctgg cttaactcat tgtcggatgt attggggatt  8040
gacgtggata tcgcggcacc cgtcatcgac atgtccagct tcgccaatgc tgactgcatg  8100
acgtgtccgg ttaccggcct gcgggtgagg gaccttgcca cagatgcggc ccccgaggtg  8160
aggagaggac atcgtgaccg ctaatcccta cgctgctccc acggaccgt tggcccctta   8220
tagcgccgtg cttgtcgttt cttttggcgg tccgcgttcc cctgaagagg tcatgccttt  8280
tctgagaagg gtctcccacg gtcgcatccc tgaagaacgc ttggctgatg tcgcccgaca  8340
ctatgaccgt ttcggcggtg tcagcccgat taacgatgcg aggacgtttt tcgtcaacgc  8400
gattgggaat gaactgcgcc gtcacggagt acgagttcca gtgctgttag ggaaccgcaa  8460
cggcacccc ttccttgagg aagcgctgac tgacatgcac gcgcacgggg tgcgtcgggt   8520
gttagcggtt gtcacctctg cctacgccag ttactccggg tgccgtcagt atcgcgagga  8580
gatcgcgact gccctggctc acgccggtat caccgatatg caggtcgaca aggtacctcc  8640
ctttaacgag gcgccgggat tcattcgcgc taacgcggaa gctctgatgc aggcgtttat  8700
gcggatccg cctactcctc ttgaggctac ccgcgtcgtt ttcgtcactc actccatccc   8760
tgactctatg caggacgcat ctggcgctgg gcagccgggg acggattaca tttctcagca  8820
caaggcggtt tgtgagaggg tcgctggtca ggtgcgcgac gtcttcggga atatgccgca  8880
gtgggacttg gcctattgct cgaggtcggg gcgacccagc gacccgtggc ttgaaccgga  8940
cattatcgat cacctccgca gtcttcccga acagggcgtg caatctgttg tcgtcgctcc  9000
aattggcttc gttgctgacc acatggaggt cgttaatgac cttgattacg aggccgccga  9060
ggcagctaag gagtccgggc tcgccttcac gcgggcgggc accgctggca cccatcccga  9120
ctttatcgct gatctcgccg ggctcatctt gtcccaggcc gcggcggctc gtggtgaggg  9180
tggcaatcta acgtcgtggc cggctccttg cgtcgccggt tgttgccgac gctaccggga  9240
cgctcaggac attccagccg tctccggtgg tgatgtcgag tccgtagctg ccggtgccga  9300
tgtagtcgat gctgaaccag gaggtgtgga ttttgtgcga agcggctcag cgagtgccga  9360
cgatcgcccg gggccagagg cggtcgaact ggagactcct ccttccccct acaacccgtt  9420
gactaaggag gcccccatgt ctgatcattc gagtgctgat tcggtgattg agggaccacg  9480
cgacgacgaa gttcccgccg gctcctacac cgcaccgacc gatccccgcg ataccccggt  9540
cattcccgag gaggtcaacg cctccagcaa gtgggcgatg tactcggtat tccgcgtcgc  9600
gaccgcgctt cctgccgagg atgacgagcg tcgccgcctt gttgagggct ccgacgagtg  9660
ggcgggacag tccggtgtcg acacccgagg atggtacgac ctgtcgggcc tgcgcgctaa  9720
cgccgacctg ctggtgtggt gggttagcga cgatccggcg gtgctgcagg atgcctacca  9780
tcgtttccgc gcatctgggc tggggcgcca cctggaaccg gtgtggtcga acgtaggagt  9840
tcatcgtcct gcggagttca acaagtctca cctgccctca tgctttgccg gcatcgcccc  9900
gaggcgttgg gctgcgttct accccttcat tcgctccaag gagtggtacc tccttccggc  9960
ggctgatcgt tcccgcatgc tgcgcgaaca cggcatcgtc ggcgcggcca gctccgacgt 10020
caaagcgtcg acgttggcgg cattcgcgct cggggactac gagtggattc tcgcgttgga 10080
gggtgacgac ctcgcccgta ttgtcgatgt catgaaggac cttcgttacg ttgaagcccg 10140
tcgttatgtc gacgtggata cccccttctt caccggcgag cgcgtttctc cggtggtgtg 10200
ggccgaccgt cagatgagag cctga                                      10225

SEQ ID NO: 2           moltype = DNA  length = 10224
FEATURE                Location/Qualifiers
source                 1..10224
                       mol_type = genomic DNA
                       note = Beta type locus reference
                       organism = Cutibacterium acnes
SEQUENCE: 2
tcaggctctc atctggcggt cggcccacac caccggagaa acgcgctcgc cggtaaagaa   60
ggggtgtatcc acgtcgacat aacgacgggc ttcaacgtaa cgaaggtcct tcatgacatc  120
aacaacacgg gcgaggtcgt caccctccaa ggcgagaatc cactcgtagt ccccgagcgc  180
gaatgccgcc aacgtcgacg ccttgacgtc ggagctggct gcgccaacga taccgtgttc  240
gcgcagcatg cgggaacgat cagccgccgg aaggaggtac cactccttgg agcgaatgaa  300
ggggtaaaac gcagcccaac gcctcggggc gatgccggcg aagcatgagg gcaggtgaga  360
cttgttgaac tccgcaggac gatgaactcc tacgttcgac cacaccggtt caaggtggcg  420
ccccagccca gatgcgcgga aacgatggta ggcgtcctgc agcaccgccg gatcgtcgct  480
aacccaccac accagcaggt cggcgttagc gcgcaggcct gacaagtcgt accatccacg  540
agtgtcgaca ccggagtgtc ccgcccactc gtcggaaccc tcaacaaggc ggcgacgctc  600
gtcatcctcg gcaggaagcg cggtcgcgac gcggaataca catcg cccattttgct      660
ggaggcgttg acctcctcgg gaatgaccgg ggtgtcgcgg gatcggtcg gtgcggtgta   720
ggagccggcg ggaacttcgt cgtcgcgtgg tccctcaatc accgaatcag cactcgaatg   780
gtcagacatg ggggtctcct tagtcaacgg gttgtagggg gaaggaggag tctccagttc   840
gaccgcctct ggccccgggc gatcgactgc actcgctgag ccgctgggca caaaaaccgc   900
acctcctggt tcagcatcga ctacatcggc accggcagct acagactcga catcactacg   960
ggagacggtt ggaatgtcct cagcgtccgg gtacgtcgg caacagccag cggcgcaggg    1020
agccggccac gacgttagat tgccaccctc accacgagcc gccgcggcct gggacaagat   1080
gagcccggcg agatcagcga taaggcggg atgggtgcca gcggtcgccg cccgcgtgaa    1140
ggcgagcccg gacaccttgg ctgcctcggc ggcctcgtaa tcaaggtcat taacgacctc   1200
catgtggtca gcaacgaagc caattggagc gacgacaaca gactgcacgc cctgctcggg   1260
aagattgcgc aggtgatcga taatgtccgg ttcaagccac gggtcgttgg gacgcccga    1320
cctcgagcag taggccaagt cccactgcgg catattcccg aaaacctgac gcacctggcc   1380
ggcgaccttc tcacaaaccg ctttgtgctg ggaaatgtag tccgttcccg gctgcccagc   1440
gccgatgcg tcctgcatag agtcagggat ggagtgagtg acgaaaacga cgcgggtagc   1500
ttcgagagga gtaggtggga tccgcataaa cgcctgcatc agagcttccg cgttagcgcg  1560
```

```
aatgaatccc ggcgcctcgt tgaaggggggg taccttgtcg acctgcatat cggtgatacc  1620
gacgtgagcc agagcagtcg cgatctcctc gcgatactga cggcaccegg agtaactgge  1680
gtaggcagag gtgacaaccg ctaacacccg acgtacccg tgcgcgtgca tgtcagtcag  1740
cgcttcctca aggaaggggg taccgttacg gttccctaac agcactggaa ctcgtactcc  1800
gtgacggcgc agttcattcc caatcgcgtt gacgaaaacg tccgtcgcat cgttaatcgg  1860
gctaacaccg ccgaaacggt catagtgccg ggcgacatca gccaagcgtt cttcagggat  1920
gcgaccgtgg gagaccttc tcagaaaagg catgacctct tcgggggaac gcggaccgcc  1980
aaaagaaacg acaagcacgg cgccataagg ggccaacggg tccgtggggg cagcgtaggg  2040
gttagcggtc acgatgtcct ctcctcacct cggggtgccg catctgcggc aaggtcctcc  2100
acccgcaggc cggtaaccgg acacgtcatg cagtcagcat tggcgaagct ggacatgtca  2160
atgacgggtg ccgcgatgtc cacgtcgatc cccaatacat ccgacaatga gttaagccag  2220
cgatcgccca agccctgctc agaggccatc ctggctcgag ccgacgggat gtgcgccata  2280
gacgcagcga gccgtcgaag ggacgccgct acctcatcga cagggaccga gccttcttcg  2340
ggcagacgct ccagttcagc agtaacgaga tctgaaatga cgtcgcgcag agcgacgaca  2400
gccgggggcca tccgacgacg ttcgaggtct acggcaaagt gacggactcc cgtagcgatg  2460
atgtgttcgg cggcggcccg ctcagcttcc gcagaggcgg gaacagcctg ccggatcgtc  2520
tcaaggtcga tgacctctac cccagcgggg acaggctcct caacgtcccc actgattgct  2580
aaatcgagca ccatgagatc tcggcccctt cgagcatcga ccgcgcgcgg agcagcctca  2640
gccgacaacg caggaacccc cgacccacgg caggtgacga caagatcagc ttgtgccagc  2700
acggcgtcga tgtcgagagc ctcactgacc cggtggcgtc gagcaaatcc ggcggcacgt  2760
ccggaggctg aatggacttg aatctcggcg accccccgag aactcagctg ggcgcacgac  2820
gcaccggcat aggagccagt ccccataacg agcacccgag cgcatccaa gcccatccgc  2880
tgggcaacga gatcaagccc gaccgcgaca acgtgcgtc cctcagcagc caacgcagtc  2940
tcggtagcga catgacgtga cgtcttgaga gcttcctcaa cgacgtgacc aatggtgtag  3000
gagacggtct gttcacggcg cgcctcactg agagcacgct tcatctgtcc ggcgacctca  3060
cgttcccccaa aaaccatcga ctccatgccc gcagccaccg gaacaaaacg ccaaacggct  3120
tcgttctcac agacgagctg ggcagattcg gctaacacgt ttgctccgtg atcggcaatg  3180
cacctgcgta acgcggcctc gtcgaaccct tgccgcacgg cttcagggga ggtttcaacg  3240
atcaggcaca cccggttgca cgttgacagc acaagggcgc cccggatctg gggatgatcg  3300
gtcaatgcca ggcaagtcc gtcaacctgca gcggccgcc cggaaacgac gccaagccca  3360
tgctcggcat gatccacggt caagacacac aatcccacga agcgttattc aaccatgctg  3420
taacgacgaa ccccagtaca tacgaagctc ataactcgcc caataatcgt cccatgggcg  3480
gcatccgcac gtggtgggc acaatcgggg tgatgactga gaccactacc ttcacggcag  3540
attcaccgct tctgcaagcc atgactgggc accgccctac cgtcgccccg gtgtggttta  3600
tgcgccaagc aggccgttcg ctaccggagt ccgagagggc ccgagaaggc accacgatgc  3660
tcgagtcttg cctcaaccct gagctcgccc ccgagattac ctgccaacct gtgcgccgcc  3720
accacgtcga cggggccgtt ctctactccg acatcatggt gccgctagcc ctggcggggg  3780
cagaggtgcg cattgagcca ggagtcgggc ccgttctcga cgagcccgtc cgcactgcct  3840
ccgacgttga ccgcattact cgacgtcatg tcgaggaccc ctcggctatc gaggaggctg  3900
cacgcctggc gatcaccgag ttaggcgacg tcacaccgct catcggtttc gcgggtgccc  3960
cgtttactat cgccgcctac ctcgtcgagg gcggcccctc ccgcgaccat ctgtctgccc  4020
gggcgatgat gcactcagac ccacagacct gggcaaggct catggagtgg gttgccgact  4080
tggatgctgc cttcctggct gctcagctgc gcggcggggc gcgtgccatc cagctcttg  4140
attcctgggc tgggtcgctg ggcgcgagcg attatcgagc cagcgtcgca ccgttctctc  4200
agcgggctct ggctaccgtc gatccgaaca tcccggtggt tcactttggc gtcaatgcca  4260
cccatctgct gtctgagttt gcgcaggtgg cagctactgc gtcacggtac ccagtacttg  4320
gtgtcgacca ccggattagc ctcgatgagg cctgcgccac tcttatggtc tccgggatgg  4380
agatgccggt tcagggcaac atcgatcccg ccttgctctt cgccggatgg gaaccgctgg  4440
aaaccgccac ccgcgatatc gtcacggcag gacgtcaggc cctggacac gtcgtcaatc  4500
tgggtcacgg cgtgccctcc aacaccgacc ccaacgtctt gacacggctg gtggagctgg  4560
tgcactccct gtgaaccgag tagcgacaat gaacattcct gatccgcagc acgtcgacgc  4620
cgtcgtcatt ggcgggggca tggctggcct cgtggccgcc tggcagttca cccaggaggg  4680
tctgcacccg gtacttgtcg aatcccgcgg gtacactggt gggctgattg ccaggtcgac  4740
gctgccggaa gtcagctacg acatcggggc cgaggggtgg gcggtccgtc taccagacac  4800
cgctgaactg gccaccgagt tgggggttgac ggttgagaag ccgaccatcg ccccgtcttg  4860
ggtgtactgc gatgacgcct cgttcgcgat gcccgataat gccattcttg gcatcccggc  4920
gaatttgtcg gacccagccg tcgtcatcgc tctgggagcg gaaaaggctg ctcgcgccgc  4980
tgagctcgat cgcgcgccca tgcctgagga tcttcctcgc gacctgggta cgctcgtggc  5040
ctcccggatg ggtccagaag tactgcgacg tctcgtcacc ccaatcgccg ggggaatcca  5100
cgccgccgat ccacatctac tgtcagccga cgtcgtctcc cccggtctga gggctgccgc  5160
ccaggccacc ggatcgctag ccgcgggagt tgcgctgtgc cgctcacgga tgccagcggg  5220
gccccgcagtc gcgtcggtag ccggtggcat gttcatcatg ccggccgagc tgcgtcgtca  5280
ggcagaacag gccggcgcga cgaccatgac ccgagtagga gctcgcggac taacccgcca  5340
cgaagatcag tggctcgtgg agaccgctgg aacctctcgc cattgcc  5400
ccccgtcacc aacggcgaga gtcgttcct cctgaccccct cgggtcgtcg tagcctgttc  5460
ggctggacct gccacaaaac tgctcagcaa tgtcatcgag accgttggac ccagatggc  5520
gccaggcgcg ccgatcggcc acgtcaatct cgccttgcag gcacccgagc tagactccag  5580
cccacgcgga aacggcatgc tggtggcgcc cggaacgacc accgttactg ccaaggcact  5640
tacccacatg tcggcgaagt ggcccagctt gagagaatca tgtcccgaag gtctccactt  5700
gctacgggtt tccttatggtc gatcggtga aacgaatgtc tcttttgagca tcgaccaggc  5760
gctagcggac gcctccgtcc tactcggtgt cgatctctcg gcggagcagg tcgtagactc  5820
ccagatcatt cactggacag gttccctcgc accgacaact ccagaccc gagcatggcg  5880
cgacggtctg caccgccagc tagaggcatt gaaccagtct ggacggggggc gaattggctt  5940
agtcgggcg tgggcatcgg gttcgggcat tgccgctcg gtggcgaac 6000
tgtccgtcaa cttgtctgat ggcagactga atcggcgtcg gtactgagtg ccacaatagg  6060
caatatgtct gcgatcgtc tgggaacccg tgccagcact ctggctacta ctcaatcaga  6120
gatggttgcg aggctgctca gatcggaggg gctggacgtc gatctgacga cgatcactac  6180
tcacggggac acctcgacgg cctcgttagc ggcgatggga ggaatcgggg tcttcgcctc  6240
ggcgatccgt gcgaccctcc tcaagggaga agccgacatt gccgtccact cattcaagga  6300
```

```
cctaccgaca ggacgtccgc tgggcctggc gatcggtgcc gttccagctc gagcagaccc  6360
gcgtgacgct ttggtggccc gtgatgggcc caccttcac gacctcccgc aggaagctag  6420
cgtcggaacg ggctcgccac gtcgggccgc acagttgttg gcggtcagac cagacctgac  6480
gatcgtcgac atccgtggaa acgtcgacac ccggctgggt cgtgtcaagg gactcggcca  6540
ctacgccaaa ggtggtggca aggaggacct cgacgcctgc gtgctcgcgg cctctggact  6600
agctcgactg ggtcatagcg gcaccgtcac tgagttcctc gacccgtcgg tagtgctgcc  6660
tgccctgcc cagggagcgc tagccgtcga atgccggacc gctgattcgc gtcatggcaa  6720
gctcgccaag gcgttggcac ggattgacga ccgcagaacc aggctggccg ccactgcgga  6780
acgtgcggtg ctctcccatc tggaggcggg gtgcgctgcc cccatcggag cattggctca  6840
gctcaagcca gtttcgggaa gttccccaca agtgttaact ctggatgttg tcgtagctac  6900
tgtcgatggc tcccgcatca ttcgggaaca ggtcagcgtc gaattacccg cggaggtgga  6960
ttcagcactg gctgctgcgc atacgctggg ggtgacggct gccgaggagt tgctggacga  7020
tggtgccgcc gacgttgcag atctcaaagc ttcaggaagc actcgatgac cacaaaccct  7080
gccgatctcg tcaagccccc ggttgtcgtt ccccgcacga actcccacga caattcgtg  7140
acgactttga agcaggccgg ttatggagtg atccacacag cgctcgacgcg caccgtcacc  7200
ttgccggacg cagaggggct cactaccccct gacctgtggc atgccgactg gctggtcgtc  7260
acctcgaaga ccaccgtcgg actgctccct accccgttgc cgaatcccaa catcaaagta  7320
gccgcggtcg gtgtcgctac ctccgctgcg ctgcgcacaa gtgggattga cgtcgacttc  7380
gtccccgacg atcacagcgg cgctggtctg gtcgccgagt ggccaggcgg aaccgccagc  7440
atcctcctac caacgtccca gttggccgcc gacaccgtac cgctgggact aacgaagatc  7500
ggctgcacgg tgaaccgatt ggaggtctac accaccgctg ccgtcgagaa actacctgag  7560
gtcatcgccc agtcgtggcc gtctgtcggg gtcgggcgtc tcactgcctc ctcggtggga  7620
cgtgccctcg tcgagctggt ggagccgctg ggatgcgtc atcagaagct cgtcgccctc  7680
ggcaagccca ctgcaagaac actcgaggag ctcggtcacc cagcgcatgc ggtggcctcc  7740
tccccctactc ctgaagccgt ccttgaggcg gttgagtcct tggtcgcctg accgacggcc  7800
gttcgcgaag gaagttgatc atgaacccgt acctgcctga tgccagtgat ccccgcatgg  7860
ctggggtcaa gccattgccc gaggggctgc gtcctgtttc tcgtccgcgt cgactacgca  7920
ccactcctgc gatgcgccga atggtcgccg aaacccgcgt cgtccccgcc cagttgatac  7980
tgccggcgtt cgtcaagggg ggggtcgatt ccccgtcga gatcaccagc ctgcccggcc  8040
aatttcagca ctccaccgag tcgattaaag agctcgccac ccaagctgcc gaggccgtca  8100
tcggtggtat tgacctgttt ggtatcccgg aacataaaga cgagatcggt tctcaggcct  8160
gggacccgaa aggcatcctc aacgccggca tctctgctgt gcgcgaggcc gtcggcgacg  8220
atctggtgat ctgtgccgac acctgtctag acgagttcac cgaacatgga cattgcggag  8280
ctctgacccc tgatggtcgc gtcgataatg actccaccgt gccgctatat gccgcgatgg  8340
cggtctccca agcgcgcgcc ggagcccaca tggtctcccc gtcggggatg atggacggtc  8400
agatcgctgt cattgcgat gctctggatc gcgaggatt caccgacgtg tccatcatgg  8460
cctattcagc taagtacgct tcagccttct ttggcccctt ccgggacgcc gtagactgtt  8520
cccttaaggg tgatcgcaaa gcttaccagc aggatccatc gaaccgccgg gaaggcctac  8580
gcgaaaacct tctcgacctc gccgagggag ccgatctggt catgggaacg cgccctccc  8640
actacctcga cgtgttgtcc gatgtcgccg aggtgtcgca ggtaccggtt gccgcttacc  8700
aggtctctgg agaatacgcc atgtcgagg ccgctgccgc caacgttgg atcgatcgcc  8760
gacggtgcat cggagagtcc ctgacctcga tcgtgcgtgc cggtgccgat ctcgttttga  8820
cctactgggc aatcgaagcg gcccagatgt tccgcgagga cctctgaccc gtggtgatca  8880
tgctcaccac aaaccccaca ccggaaggaa gacatgacct ccaacgccga actgttctct  8940
gccgccagg ccgtcattcc cggcggggtt gattccccgg tgcgggctta cggctcggta  9000
ggcggggttc cgcgcttcat cgagaaggcc caagcccgt ggatctggga cgccgaaggc  9060
acgcgctacg tcgatctggt gtgcacctgg ggcccgcgtc tgcttgggca tgcccgtccc  9120
gaggtcgtct ctgcggttca ggaggccgcg tcgaaggggc tgtccttttgg cgccccgacc  9180
cgcaccgaaa ccgaactagc ggatgccatc atcgagcgga tggatccggt cgagaaggtg  9240
cgtttcgtct cgacaggcac tgaggcgaca atgactgcgg tccgtttggc ccgtggcgcc  9300
accggtcgtg acgtcatcgt caagtttgcc ggtaattacc acggccattc tgacgccctg  9360
ctcgccgccg ccggttccgg tgtagcgacg gctggtctac ccggttcggc cggtgtgcca  9420
gccgcctcga ctgccgacac tattgtggtg gattacaacg acgtcgccgc cctcgacgcg  9480
gtgttctccg agcgtggcga ccagattgct gcagtgatcg tggagtcctg cccggccaat  9540
atgggagttg ttccgcccga gcccggcttc aatgccgcga ttcgtcgcct cacaaccgag  9600
cacgcgccc tcatgatcac cgacgaagta ctcaccggat tccggtgcag ccctgcggga  9660
ttctggggtt tgcaacagca ggccggcgag gacttcgcgc ccgacatttt caccttcggc  9720
aaggtcgtgg gcggaggcat gccgctggct gccctgggtg ggcacgccga tgtcatggac  9780
ttgctggctc ctaccggccc cgtctaccag gccgcacttt tgtccggtaa cccgctgggc  9840
accgtcgcgg gtgtcaaaac cctacagctg gccgacgccg aggtgtatca gcgcctcgat  9900
gtccgctccg agaaatggcg caatgagctc gaatccgcac ttgacgcagc cggcgtcacg  9960
taccgcctgc agaacgccgg aaatttcttc agccgtattc tcggcgtcga ctccccggtg 10020
cgcaattacg acaacgccaa gtctcagaat gccgaggctt acaccgcgtt cttccacgcg 10080
atgctagatg ccggggtcaa cctgccgcca tcgtgctttg aggcctggtt cctctcggac 10140
gctcacgacg acgaagcttt cgaggttttc cgcgccgccc tgccagggc tgcccaggcg 10200
gctgcccagg tgatcagtgc ctga                                        10224
```

SEQ ID NO: 3          moltype = DNA   length = 1224
FEATURE               Location/Qualifiers
source                1..1224
                      mol_type = genomic DNA
                      note = hemA reference
                      organism = Cutibacterium acnes
SEQUENCE: 3
```
gtgctgtcaa cgtgcaaccg ggtgtgcctg atcgttgaaa cctcccctga agccgtcgcg   60
caagggttcg acgaggccgc gttacgcagg tgcattgccg atcacggagc aaacgtgtta  120
gccgaatctg cccagctcgt ctgtgagaac gacgccgttt ggcgtttgtt ccgggtggct  180
gcgggcatgg agtcgatggt ttttggggaa cgtgaggtcg ccggacagat gaagcgtgct  240
ctcagtgagg cgcgccgtga acagaccgtc tcctacacca ttggtcacgt cgttgaggaa  300
```

-continued

```
gctctcaaga cgtcacgtca tgtcgctacc gagactgcgt tggctgctga gggacgcacc    360
gttgtcgcgg tcgggcttga tctcgttgcc cagcggatgg gcttggatgg cgctcgggtg    420
ctcgttatgg ggactggctc ctatgccggt gcgtcgtgcg cccagctgag ttctcggggg    480
gtcgccgaga ttcaagtcca ttcagcctcc ggacgtgccg ccggatttgc tcgacgccac    540
cgggtcagtg aggctctcga catcgacgcc gtgctggcac aagctgatct tgtcgtcacc    600
tgccgtgggt cggggggttcc tgcgttgtcg gctgaggctg ctcggcgcgc ggtcgatgct    660
cgaaggggcc gagatctcat ggtgctcgat ttagcaatca gtggggacgt tgaggagcct    720
gtccccgctg gggtagaggt catcgacctt gagacgatcc ggcaggctgt tcccgcctct    780
gcggaagctg agcgggccgc cgccgaacac atcatcgcca cgggagtccg tcactttgcc    840
gtagacctcg aacgtcgtcg gatggccccg gctgtcgtcg ctctgcgcga cgtcatttca    900
gatctcgtta ctgctgaact ggagcgtctg cccgaagaag ctcggtccc tgtcgatgag    960
gtagcggcgt cccttcgacg gctcgctgcg tctatggcgc acatcccgtc ggctcgagcc    1020
aggatggcct ctgagcaggg cttgggcgat cgctggctta actcattgtc ggatgtattg    1080
gggatcgacg tggacatcgc ggcacccgtc attgacatgt ccagcttcgc caatgctgac    1140
tgcatgacgt gtccggttac cggcctgcgg gtggaggacc ttgccgcaga tgcggcaccc    1200
cgaggtgagg agaggacatc gtga                                            1224

SEQ ID NO: 4            moltype = DNA   length = 1047
FEATURE                 Location/Qualifiers
source                  1..1047
                        mol_type = genomic DNA
                        note = hemB reference
                        organism = Cutibacterium acnes
SEQUENCE: 4
atgaaccccgt acctgcctga tgccagtgat ccccgcatgg ctgggtcaa gccattgccc     60
gaggggctgc gtcctgtttc tcgtccgcgt cgactacgca ccactcctgc gatgcgccga    120
atggtcgccg aaaccccgcgt cgtccccgcc cagttgatac tgccggcgtt cgtcaagggg    180
ggggtcgatt ccccgtcga gatcaccagc ctgcccggcc aatttcagca ctccaccgag    240
tcgattaaag agctcgccac ccaagctgcc gaggccggta tcggtggtat tgaccctgttt    300
ggtatcccgg aacataaaga cgagatcggt tctcaggcct gggacccgaa aggcatcctc    360
aacgccggca tctctgctgt gcgcgaggcc gtcggcgacg atctggtgat ctgtgccgac    420
acctgtctag acgagttcac cgaacatgga cattgcggag ctctgacccc tgatggtcgc    480
gtcgataatg actccaccgt gccgctatat gccgcgatgg cggtctcca gcgcgcgcc    540
ggagcccaca tggtctcccc gtcggggatg atggacggtc agatcgctgt cattcgcgat    600
gctctggatc gcgagggatt caccgacgtg tccatcatgg cctattcagc taagtacgct    660
tcagccttct ttggcccctt ccgggacgcc gtagactgtt cccttaaggg tgatcgcaaa    720
gcttaccagc aggatccatc gaaccgccgg aaggcctac gcgaaaccct tctcgacctc    780
gccgaggag ccgatctggt catggtgaag cccgcctccc actacctcga cgtgttgtcc    840
gatgtccgcg aggtgtcgca ggtaccggtt gccgcttacc aggtctctgg agaatacgcc    900
atgctcgagg ccgctgccgc caacggttgg atcgatcgcc gacggtgcat cggagagtcc    960
ctgacctcga tcgtcgtgc cggtgccgat ctcgttttga cctactgggc aatcgaagcg    1020
gcccagatgt tccgcgagga cctctga                                        1047

SEQ ID NO: 5            moltype = DNA   length = 1005
FEATURE                 Location/Qualifiers
source                  1..1005
                        mol_type = genomic DNA
                        note = hemC reference
                        organism = Cutibacterium acnes
SEQUENCE: 5
atgtctgcga tccgtctggg aacccgtgcc agcactctgg ctactactca atcagagatg     60
gttgcgaggc tgctcagatc ggaggggctg gacgtcgatc tgacgacgat cactactcac    120
ggggacacct cgacggcctc gttagcggcg atgggaggaa tcggggtctt cgcctcggcg    180
atccgtgcga ccctcctcaa gggagaagcc gacattgccg tccactcatt caaggaccta    240
ccgacaggac gtccgcttggg cctggcgatc ggtgccgttc cagctcgagc gacccgcgt    300
gacgctttgg tggccgtgga tgggctcacc cttcacgacc tcccgcagga agctagcgt    360
ggaacgggct cgccacgtcg ggccgcacag ttgttggcgg tcagaccaga cctgacgatc    420
gtcgacatcc gtgaaacgt cgacacccgg ctgggtcgtg tcaagggact cggccactac    480
gccaaaggtg gtgcaagga ggacctcgac gccgtcgtgc tcgcggcctc tggactagct    540
cgactgggtc atagcggcac cgtcactgag ttcctccaca cgtcggtagt gctgcctgcc    600
cctgcccagg gagcgctagc cgtcgaatgc cggaccgctg attcgcgtca tggcaagctc    660
gccaaggcgt tggcacggat tgacgaccgc agaaccaggc tggccgccac tgcggaacgt    720
gcggtgctct cccatctgga ggcggggtgc gctgcccccca tcgagcatt ggctcagctc    780
aagccagttt cgggaagttc cccacaagtg ttaactctgg atgttgtcgt agctactgtc    840
gatggctccc gcatcattcg ggaacaggtc agcgtcgaat acccgcgga ggtggattca    900
gcactgctg ctgcgcatac gctggggtg acggctgccg aggagttgct ggacgatggt    960
gccgccgacg ttgcagatct caaagcttca ggaagcactc gatga                    1005

SEQ ID NO: 6            moltype = DNA   length = 726
FEATURE                 Location/Qualifiers
source                  1..726
                        mol_type = genomic DNA
                        note = hemD reference
                        organism = Cutibacterium acnes
SEQUENCE: 6
atgaccacaa accctgccga tctcgtcaag ccccggttg tcgttccccg cgacgactcc     60
cacgacaaat tcgtgacgac tttgaagcag gccggttatg gagtgatcca cacagcgctg    120
acgcgcaccc tcaccttgcc ggacgcagag ggctcacta cccctgacct gtggcatgcc    180
gactggctgg tcgtcaccctc gaagaccacc gtcggactgc tccctacccc gttgccgaat    240
```

```
cccaacatca aagtagccgc ggtcggtgtc gctacctccg ctgcgctgcg cacacgtggg  300
attgacgtcg acttcgtccc cgacgatcac agcggcgctg gtctggtcgc cgagtggcca  360
ggcggaaccg ccagcatcct cctaccaacg tcccagttgg ccgccgacac cgtaccgctg  420
ggactaacga agatcggctg cacggtgaac cgattggagg tctacaccac cgctgccgtc  480
gagaaactac ctgaggtcat cgcccagtcg tggccgtcgt tcggggtcgg tccgtcact   540
gcctcctcgg tgggacgtgc cctcgtcgag ctggtggagc cgctgggatg gcgtcatcag  600
aagctcgtcg ccctcggcaa gcccactgca agaacactcg aggagctcgg tcacccagcg  660
catgcggtgg cctcctcccc tactcctgaa gccgtccttg aggcggttga gtccttggtc  720
gcctga                                                             726

SEQ ID NO: 7          moltype = DNA  length = 1281
FEATURE               Location/Qualifiers
source                1..1281
                      mol_type = genomic DNA
                      note = hemE reference
                      organism = Cutibacterium acnes
SEQUENCE: 7
atgatcggtc aatgccaggc caagtccgtc aacctgcgcg gccgcctcgg aaacgacgcc   60
aagcccctgc tcggcatgat ccacggtcaa gacacacaat cccacgaagc gttattcaac  120
catgctgtaa cgacgaaccc cagtacatac gaagctcata actcgcccaa taatcgtccc  180
atgggcggca tccgcacgtg gtggggcaca atcggggtga tgactgagac cactaccttc  240
acggcagatt caccgcttct gcaagccatg actgggaccg ctgccccggtg              300
tggtttatgc gccaagcagg ccgttcgcta ccggagtacc gcgaagcccg agagggcacc  360
acgatgctcg agtcttgcct caaccctgag ctcgccgccg agattacctg ccaacctgtg  420
cgccgccacc acgtcgacgg ggccgttctc tactccgaca tcatggtgcc gctagccctg  480
gcggggggcag aggtgcgcat tgagccagga gtcgggcccg ttctcgacga gcccgtccgc  540
actgcctccg acgttgaccg cattactcga cgtcatgtcg aggaccctc ggctatcgag  600
gaggctgcac gcctggcgat caccgagtta ggcgacgtca caccgctcat cggtttcgcg  660
ggtgccccgt ttactatcgc cgcctacctc gtcgagggcg gccctcccg cgaccatctg  720
tctgcccggg cgatgatgca ctcagaccca cagacctggg caaggctcat ggagtgggtt  780
gccgacttgg atgctgcctt cctggctgct cagctgcgcg gcggggcgcg tgccatccag  840
ctctttgatt cctgggctgg gtcgctgggc gcgagcgatt atcgagccag cgtcgcaccg  900
ttctctcagc gggctctggc taccgtcgat ccgaacatcc cggtggttca ctttggcgtc  960
aatgccaccc atctgctgtc tgagtttgcg caggtggcag ctactgcgtc acggtaccca 1020
gtacttggtg tcgaccaccg gattagcctc gatgaggcct gcgccactct tatggtctcc 1080
gggatggaga tgccggttca gggcaacatc gatcccgcct tgctcttcgc cggatgggaa 1140
ccgctggaaa ccgccacccg cgatatcgtc acggcaggac gtcaggcccc tggacacgtc 1200
gtcaatctgg tcacggcgt gccctccaac accgaccca acgtcttgac acggctggtg  1260
gagctggtgc actccctgtg a                                            1281

SEQ ID NO: 8          moltype = DNA  length = 2052
FEATURE               Location/Qualifiers
source                1..2052
                      mol_type = genomic DNA
                      note = hemH reference
                      organism = Cutibacterium acnes
SEQUENCE: 8
gtgaccgcta accctacgc tgcccccacg gacccgttgg cccccttatgg cgccgtgctt   60
gtcgtttctt ttggcggtcc gcgttccccc gaagaggtca tgccttttct gagaagggtc  120
tcccacggtc gcatccctga agaacgcttg gctgatgtcg cccggcacta tgaccgtttc  180
ggcggtgtta gccgattaa cgatgcgacg gacgttttcg tcaacgcgat tgggaatgaa  240
ctgcgccgtc acggagtacg agttccagtg ctgttaggga accgtaacgg tacccccttc  300
cttgaggaag cgctgactga catgcacgcg cacgggggta cgtcgggtgtt agcggttgtc  360
acctctgcct acgccagtta ctccgggtgc cgtcagtatc gcgaggagat cgcgactgct  420
ctggctcacg tcggtatcac cgatatgcag gtcgacaagg tacccccctt caacgaggcg  480
ccgggattca ttcgcgctaa gcgcgaagct ctgatgcagg cgtttatgcg gatcccacct  540
actcctctcg aagctacccg cgtcgtttc gtcactcact ccatccctga ctctatgcag  600
gacgcatccg gcgctgggca gccgggaacg gactacattt cccagcacaa gcggtttgt   660
gagaaggtcg ccggccaggt gcgtcaaggtt tcgggaata tgccgcagtg ggacttggcc  720
tactgctcga ggtcgggggcg tcccaacgac ccgtggcttg aaccggacat tatcgatcac  780
ctccgcaatc ttcccgagca gggcgtgcag tctgttgtcg tcgctccaat tggcttcgtt  840
gctgaccaca tggaggtcgt taatgacctt gattacgagg ccgccgaggc agccaaggtg  900
tccgggctcg ccttcacgcg ggcggcgacc gctggcaccc atcccgcctt tatcgctgat  960
ctcgccgggc tcatcttgtc ccaggccgcg gcggctcgtg gtgagggtgg caatctaacg 1020
tcgtggccgg ctccctgcgc cgctggctgt tgccgacgt acccgacgc tcgaggacatt 1080
ccaaccgtct ccggtagtga tgtcgagtct gtagctgccg gtgccgatgt agtcgatgct 1140
gaaccaggag gtgcggtttt tgtgcccagc ggctcagcga gtgcagtcga tcgcccgggg 1200
ccagaggcgg tcgaactgga gactcctcct tcccccctaca acccgttgac taaggagacc 1260
cccatgtctg accattgag tgctgattcg gtgattgagg gaccacgcga cgacgaagtt 1320
cccgccggct cctacaccgc accgaccgat cccgcgaca cccggtcat tcccgaggag 1380
gtcaacgcct ccagcaaatg ggcgatgtac tcggtattcc gcgtcgcgac cgcgcttcct 1440
gccgaggatg acgagcgtcg ccgccttgtt gagggttccg acgagtgggc gggacactcc 1500
ggtgtcgaca ctcgtggatg gtacgacttg tcaggcctgc gcgctaacgc cgacctgctg 1560
gtgtgtgggg ttagcgacga tcggccggtg ctgcaggacg cctaccatcg tttccgcgca 1620
tctgggctgg ggcgccacct tgaaccggtg tggtcgaacg taggagttca tcgtcctgcg 1680
gagttcaaca agtctcacct gccctcatgc ttcgccggca tcgccccgag gcgttgggct 1740
gcgttttacc ccttcattcg ctccaaggag tggtacctcc ttccggcggc tgatcgttcc 1800
cgcatgctgc gcgaacacgg tatcgttggc gcagccagct ccgacgtcaa ggcgtcgacg 1860
ttggcggcat tcgcgctcgg ggactacgag tggattctcc ccttggaggg tgacgacctc 1920
```

```
gcccgtgttg ttgatgtcat gaaggacctt cgttacgttg aagcccgtcg ttatgtcgac   1980
gtggatacc  ccttctttac cggcgagcgc gtttctccgg tggtgtgggc cgaccgccag   2040
atgagagcct ga                                                       2052

SEQ ID NO: 9              moltype = DNA  length = 1311
FEATURE                   Location/Qualifiers
source                    1..1311
                          mol_type = genomic DNA
                          note = hemL reference
                          organism = Cutibacterium acnes
SEQUENCE: 9
atgacctcca acgccgaact gttctctgcc gcccaggccg tcattccggg cggggttgat    60
tccccggtgc gggcttacgg ctcggtaggc ggggttccgc gcttcatcga aggcccaa    120
ggcccgtgga tctgggacgc cgaaggcacg cgctacgtcg atctggtgtg cacctgggg   180
ccggctctgc ttgggcatgc ccgtcccgag gtcgtctctg cggttcagga ggccgcgtcg  240
aagggctgt  cctttggcgc cccgacccgc accgaaaccg aactagcgga tgccatcatc   300
gagcggatgg atccggtcga aaggtgcgt ttcgtctcga caggcactga ggcgacaatg   360
actgcggtcc gtttggcccg tggcgccacc ggtcgtgacg tcatcgtcaa gtttgccggt   420
aattaccacg gccattctga cgccctgctc gccgccgccg gttccggtgt agcgacggct   480
ggtctacccg gttcggccgg tgtgccagcc gcctcgactg ccgacactat tgtggtggat   540
tacaacgacg tcgccgccct cgacgcgtg tttctccgagc gtggcgacca gattgctgca   600
gtgatcgtgg agtcctgccc ggccaatatg ggagttgttc cgcccgagcc cggcttcaat   660
gccgcgattc gtcgcctcac aaccgagcac ggcgccctca tgatcaccga cgaagtactc  720
accggattcc ggtgcagccc gtcgggattc tggggtttgc aacagcaggc cggcgaggac   780
ttcgcgccc  acattttcac cttcggcaag gtcgtgggcg aggcatgcc gctggctgcc    840
ctgggtgggc acgccgatgt catggacttg ctgttcctca ccggccccgt ctaccaggcc   900
ggcacttttg tccggtaacc gctgccacc gtcgcgggtg tcaaaaccct acagctggcc    960
gacgccgagg tgtatcagcg cctcgatgtc cgctccgaga atggcgcaa tgagctcgaa   1020
tccgcacttg acgcagccgg cgtcacgtac cgcctgcaga acgccggaaa tttcttcagc  1080
gtattcctcg gcgtcgactc cccggtgcgc aattacgaca ccgccaagtc tcagaatgcc  1140
gaggcttaca ccgcgttctt ccacgcgatg ctagatgccg ggtcaacct  gccgccatcg  1200
tgctttgagg cctggttcct ctcggacgct cacgacgacg aagctttcga ggttttccgc  1260
gccgccctgc cgagggctgc ccaggcggct gcccaggtga tcagtgcctg a           1311

SEQ ID NO: 10             moltype = DNA  length = 1431
FEATURE                   Location/Qualifiers
source                    1..1431
                          mol_type = genomic DNA
                          note = hemY reference
                          organism = Cutibacterium acnes
SEQUENCE: 10
atgaacattt ctgatccgca gcacgtcgac gccgtcgtca ttggcggggg catggctggc    60
ctcgtggccg cctggcagtt cacccaggag ggtctgcacc tgtacttgt cgaatccgct   120
gggtacactg gtgggctgat tgccaggtcg acgctggccg gagtcagcta cgacatcggg   180
gccgaggggt gggcggtccg tctaccagac accgctgaac tggccaccga gttggggttg   240
acggttgaga agccgaccat cgccccgtct tgggtgtact cgatgacgc ctgcttgcg    300
atgcccgata atgccattct tggcatcccg gcgaatttgt cggacccagc cgtcgtcatc   360
gctctgggag cggaaaaggc tgctcgcgcc gctgagctcg atcgcgcgcc catgcctgag   420
gatcttcctc gcgacctggg tacgctcgtg gcctcccgga tgggtccaga agtactgcga   480
cgtctcgtca ccccaatcgc cggggaatc cacgccgccg atccacatct actgtcagcc    540
gacgtcgtct ccccggtct  gagggctgcc gcccaggcca ccgatcgct agccgcggc    600
gttgcgctgt gccgctcacg gatgccagcg gggcccgcag tcgcgtcggt agccggtggc   660
atgttcatca tgccggccga gctcgtcgt caggcagaac aggccggcgc gacgaccatg   720
acccgagtag gagctcgcgg actaacccgc acgaagatc agtggctcgt ggagaccgct   780
ggaacctctc gcaatccgga tccatctttg ccccccgtca ccaacggcga gagtcgtttc   840
ttcctgaccc ctcgggtcgt cgtagcctgt tcggctggac ctgccacaaa actgctcagc   900
aatgtcatcg agaccgttgg acccgagatg gcgccaggcg cgccgatcgg ccacgtcaat   960
ctcgccttgc aggcacccga gctagactcc agcccacgcg aaacggcat gctggtggcc  1020
cccggaacga ccaccgttac tgccaaggca cttacccaca tgtcggcgaa gtggcccagc  1080
ttgagagaat catgtcccga aggtctccac ttgctacggg tttcctatgg tcgatccggt  1140
gaaacgaatg tctcttttga g  catcgaccag gcgctagcgg acgcctccgt ccctactcggt 1200
gtcgatctct cggcggagca ggtcgtagac tcccagatca ttcactggac aggttccctc  1260
gcaccgcaca ctccacagac ccgagcatgg cgcgacggtc tgcaccgcca gctagaggca  1320
ttgaaccagt ctgacggggg gcgaattggc ttagtcgggg cgtgggcatc gggttcggcc  1380
attgccgctc tggtggcgca ggcccgccga actgtccgtc aacttgtctg a           1431

SEQ ID NO: 11             moltype = AA   length = 1298
FEATURE                   Location/Qualifiers
source                    1..1298
                          mol_type = protein
                          organism = synthetic construct
SEQUENCE: 11
MTKTFDSEFF NLYSLQKTVR FELKPVGETA SFVEDFKNEG LKRVVSEDER RAVDYQKVKE    60
IIDDYHRDFI EESLNYFPEQ VSKDALEQAF HLYQKLKAAK VEEREKALKE WEALQKKLRE   120
KVVKCFSDSN KARFSRIDKK ELIKEDLINW LVAQNREDDI PTVETFNNFT TYFTGFHENR   180
KNIYSKDDHA TAISFRLIHE NLPKFFDNVI SFNKLKEGFP ELKFDKVKED LEVDYDLKHA   240
FEIEYFVNFV TQAGIDQYNY LLGGKTLEDG TKKQGMNEQI NLFKQQQTRD KARQIPKLIP   300
LFKQILSERT ESQSFIPKQF ESDQELFDSL QKLHNNCQDK FTVLQQAILG LAEADLKKVF   360
IKTSDLNALS NTIFGNYSVF SDALNLYKES LKTKKAQEAF EKLPAHSIHD LIQYLEQFNS   420
```

```
SLDAEKQQST DTVLNYFIKT DELYSRFIKS TSEAFTQVQP LFELEALSSK RRPPESEDEG    480
AKGQEGFEQI KRIKAYLDTL MEAVHFAKPL YLVKGRKMIE GLDKDQSFYE AFEMAYQELE    540
SLIIPIYNKA RSYLSRKPFK ADKFKINFDN NTLLSGWDAN KETANASILF KKDGLYYLGI    600
MPKGKTFLFD YFVSSEDSEK LKQRRQKTAE EALAQDGESY FEKIRYKLLP GASKMLPKVF    660
FSNKNIGFYN PSDDILRIRN TASHTKNGTP QKGHSKVEFN LNDCHKMIDF FKSSIQKHPE    720
WGSFGFTFSD TSDFEDMSAF YREVENQGYV ISFDKIKETY IQSQVEQGNL YLFQIYNKDF    780
SPYSKGKPNL HTLYWKALFE EANLNNVVAK LNGEAEIFFR RHSIKASDKV VHPANQAIDN    840
KNPHTEKTQS TFEYDLVKDK RYTQDKFFFH VPISLNFKAQ GVSKFNDKVN GFLKGNPDVN    900
IIGIDRGERH LLYFTVVNQK GEILVQESLN TLMSDKGHVN DYQQKLDKKE QERDAARKSW    960
TTVENIKELK EGYLSHVVHK LAHLIIKYNA IVCLEDLNFG FKRGRFKVEK QVYQKFEKAL   1020
IDKLNYLVFK EKELGEVGHY LTAYQLTAPF ESFKKLGKQS GILFYVPADY TSKIDPTTGF   1080
VNFLDLRYQS VEKAKQLLSD FNAIRFNSVQ NYFEFEIDYK KLTPKRKVGT QSKWVICTYG   1140
DVRYQNRRNQ KGHWETEEVN VTEKLKALFA SDSKTTTVID YANDDNLIDV ILEQDKASFF   1200
KELLWLLKLT MTLRHSKIKS EDDFILSPVK NEQGEFYDSR KAGEVWPKDA DANGAYHIAL   1260
KGLWNLQQIN QWEKGKTLNL AIKNQDWFSF IQEKPYQE                          1298

SEQ ID NO: 12           moltype = DNA   length = 20
FEATURE                 Location/Qualifiers
source                  1..20
                        mol_type = other DNA
                        organism = synthetic construct
SEQUENCE: 12
agaagagctt tcgctcttca                                                 20

SEQ ID NO: 13           moltype = DNA   length = 20
FEATURE                 Location/Qualifiers
source                  1..20
                        mol_type = other DNA
                        organism = synthetic construct
SEQUENCE: 13
ttctcaaact cgttgcgggt                                                 20

SEQ ID NO: 14           moltype = DNA   length = 20
FEATURE                 Location/Qualifiers
source                  1..20
                        mol_type = other DNA
                        organism = synthetic construct
SEQUENCE: 14
acgaacgccg gcagcattaa                                                 20

SEQ ID NO: 15           moltype = DNA   length = 20
FEATURE                 Location/Qualifiers
source                  1..20
                        mol_type = other DNA
                        organism = synthetic construct
SEQUENCE: 15
acgatgacgt cacgcccagt                                                 20

SEQ ID NO: 16           moltype = DNA   length = 20
FEATURE                 Location/Qualifiers
source                  1..20
                        mol_type = other DNA
                        organism = synthetic construct
SEQUENCE: 16
cgtcctactc ggcgtggacc                                                 20

SEQ ID NO: 17           moltype = DNA   length = 132
FEATURE                 Location/Qualifiers
source                  1..132
                        mol_type = genomic DNA
                        organism = Cutibacterium acnes
SEQUENCE: 17
ctgttcggtg tctctacatc gacgattcgc cgcgatgtcg atgccctctc ggatgaatcc     60
aagatctgga agatttccgg gggagacgtc atgatccgac gacacgagcc tacctggcac    120
gagaaggaac aa                                                        132

SEQ ID NO: 18           moltype = AA   length = 44
FEATURE                 Location/Qualifiers
source                  1..44
                        mol_type = protein
                        organism = Cutibacterium acnes
SEQUENCE: 18
LFGVSTSTIR RDVDALSDES KIWKISGGDV MIRRHEPTWH EKEQ                       44

SEQ ID NO: 19           moltype = DNA   length = 134
FEATURE                 Location/Qualifiers
source                  1..134
                        mol_type = genomic DNA
                        organism = Cutibacterium acnes
```

-continued

```
SEQUENCE: 19
ctgttcggtg tctctacatc gacgattcgc cgcgatgtcg atgccctctc ggatgaatcc  60
aagatctgga agatttccgg gggggagacg tcatgatccg acgacacgag cctacctggc  120
acgagaagga acaa                                                    134

SEQ ID NO: 20         moltype = AA  length = 31
FEATURE               Location/Qualifiers
source                1..31
                      mol_type = protein
                      organism = Cutibacterium acnes
SEQUENCE: 20
LFGVSTSTIR RDVDALSDES KIWKISGGET S                                 31
```